United States Patent
Thomas et al.

(10) Patent No.: US 7,820,408 B2
(45) Date of Patent: Oct. 26, 2010

(54) METHODS OF IMPROVING THE INTRODUCTION OF DNA INTO BACTERIAL CELLS

(75) Inventors: Michael Thomas, Davis, CA (US); Michael Rey, Davis, CA (US)

(73) Assignee: Novozymes, Inc., Davis, CA (US)

( * ) Notice: Subject to any disclaimer, the term of this patent is extended or adjusted under 35 U.S.C. 154(b) by 0 days.

(21) Appl. No.: 12/516,438

(22) PCT Filed: Nov. 29, 2007

(86) PCT No.: PCT/US2007/085840

§ 371 (c)(1), (2), (4) Date: Jun. 4, 2009

(87) PCT Pub. No.: WO2008/067423

PCT Pub. Date: Jun. 5, 2008

(65) Prior Publication Data

US 2010/0055739 A1 Mar. 4, 2010

Related U.S. Application Data

(60) Provisional application No. 60/861,896, filed on Nov. 29, 2006.

(51) Int. Cl.
*C12N 9/10* (2006.01)
*C12N 15/00* (2006.01)
*C12P 21/06* (2006.01)

(52) U.S. Cl. ...................... 435/69.1; 435/193; 435/440; 435/485

(58) Field of Classification Search ........................ None
See application file for complete search history.

(56) References Cited

FOREIGN PATENT DOCUMENTS

EP    0 618 295 A1    6/1987

OTHER PUBLICATIONS

Briggs et al., Characterization of a Restriction Endonuclease, PhaI, from *Pasteurella haemilytica* Serotype A1 and Protection of Heterologous DNA by a Cloned PhaI Methyltransferase Gene, 1994, *Applied and Environmental Microbiology* 60: 2006-2010.
Accetto et al., Type II restriction modification systems of *Prevotella bryantii* TC1-1 and *Prevotella ruminicola* 23 strains and their effect on the efficiency of DNA introduction via electroporation, 2005, *FEMS Microbiology Letters* 247: 177-183.
Smith et al., Finding sequence motifs in groups of functionally related proteins, 1990, *Proceedings of the National Academy of Sciences USA* 87: 826-830.
Chmuzh et al., The Fsp4HI Restriction-Modification System: Gene Cloning, Comparison of Protein Structures, and Biochemical Properties of Recombinant DNA Methyltransferase M.Fsp4HI, Molecular Biology, 2007, vol. 41, No. 1, pp. 37-43.
Geis et al., Sequence analysis and characterization of plasmids from *Streptococcus thermophilis*, Plasmid, 50, 2003, 53-69.
Lubys et al., Cloning and analysis of the plasmid-borne genes encoding the Bsp6I restriction and modification enzymes, Gene, 157, 1995, 25-29.
Pingoud and Jeltsch, Structure and function of type II restriction endonucleases, 2001, *Nucleic Acids Research* 29: 3705-3727.
Kumar et al., The DNA (cytosine-5) methyltransferases, Nucleic Acids Research, 22, 1994, 1-10.
Roberts et al., REBASE-restriction enzymes and DNA methyltransferases, Nucleic Acids Research, 33, 2005, 230-232.

*Primary Examiner*—Nashaat T Nashed
(74) *Attorney, Agent, or Firm*—Robert L. Starnes; Eric Fechter

(57) ABSTRACT

The present invention relates to methods of improving the introduction of DNA into bacterial host cells.

11 Claims, 22 Drawing Sheets

```
  M  T  Y  R  V  G  S  M  F  A  G  I  G  G  T  C  L  G  F  I
TTGACTTATCGAGTAGGTAGTATGTTTGCTGGGATAGGTGGAACTTGTTTAGGGTTTATC        60

Q  A  G  A  R  I  V  W  A  N  E  I  D  K  N  A  C  I  T  Y
CAAGCTGGCGCTAGGATTGTCTGGGCAAATGAAATAGACAAAAATGCTTGTATTACTTAT       120

R  N  Y  F  G  D  A  Y  L  Q  E  G  D  I  N  L  I  D  K  N
AGAAATTATTTTGGGGATGCTTACTTACAAGAGGGTGACATTAACCTAATAGATAAAAAC       180

S  I  P  E  L  D  I  L  I  G  G  F  P  C  Q  A  F  S  I  A
TCCATACCTGAACTGGACATTTTGATTGGAGGTTTTCCTTGCCAAGCCTTCTCTATAGCT       240

G  Y  R  K  G  F  E  D  E  R  G  N  V  F  F  Q  I  L  E  V
GGCTATCGTAAAGGGTTTGAAGATGAAAGGGGAAACGTGTTCTTTCAAATATTAGAGGTA       300

L  E  A  Q  R  N  V  Y  G  H  L  P  Q  A  I  M  L  E  N  V
TTGGAAGCACAAAGAAATGTTTATGGACACTTACCCCAAGCAATAATGCTTGAGAATGTA       360

K  N  L  F  T  H  D  R  G  N  T  Y  R  V  I  K  E  A  L  E
AAGAACTTATTTACACATGATAGAGGTAATACGTACAGAGTAATAAAAGAGGCTTTGGAA       420

A  F  G  Y  T  V  K  A  E  V  L  N  S  M  E  Y  G  N  V  P
GCCTTTGGTTATACCGTAAAAGCTGAGGTTCTTAATTCAATGGAATACGGTAACGTGCCA       480

Q  N  R  E  R  I  Y  I  V  G  F  Q  D  E  S  Q  A  E  R  F
CAAAACAGAGAGCGGATTTATATTGTAGGTTTTCAAGATGAGAGCCAAGCTGAAAGGTTT       540
```

Fig. 1A

```
      S   F   P   D   P   I   P   L   T   N   Q   L   N   D   V   I   D   R   T   R
    AGCTTTCCAGACCCAATTCCTTTAACAAATCAACTTAATGATGTAATTGACCGAACTCGG            600

R   V   D   K   R   Y   Y   Y   D   E   T   S   Q   Y   Y   D   M   L   R   E
    AGAGTTGATAAAAGATATTATTATGATGAAACCTCTCAATATTATGATATGTTGCGAGAA            660

A   M   D   S   T   D   T   T   Y   Q   I   R   R   I   Y   V   R   E   N   R
    GCCATGGACAGTACAGATACAACTTATCAAATAAGACGTATATATGTTCGAGAAAATAGA            720

S   N   V   C   P   T   L   T   A   N   M   G   T   G   G   H   N   V   P   I
    AGCAATGTTTGTCCTACACTGACAGCGAATATGGGAACTGGAGGGCATAATGTTCCTATT            780

V   L   D   F   E   N   N   I   R   K   L   T   P   E   E   C   L   L   L   Q
    GTATTAGACTTTGAAAATAATATAAGAAAACTAACACCAGAAGAATGCTTACTATTGCAA            840

G   F   P   A   D   Y   H   F   P   E   G   M   A   N   T   H   K   Y   K   Q
    GGTTTCCCAGCTGACTATCATTTTCCAGAAGGCATGGCAAACACTCACAAATATAAACAA            900

A   G   N   S   V   T   V   P   V   I   R   R   I   A   T   N   I   I   S   V
    GCTGGTAACTCTGTTACGGTGCCAGTTATAAGAAGAATTGCCACTAATATTATTAGCGTA            960

L   N   I   G   M   N   I   N   Q   E   H   E   Y   A   I   A   E   *
    TTGAACATTGGAATGAATATAAATCAAGAACATGAATATGCAATAGCTGAATAA                  1014
```

Fig. 1B

```
      M  F  Y  T  N  Q  P  A  I  N  C  T  T  Y  K  Q  M  L  R  S
ATGTTCTATACTAATCAACCAGCCATCAACTGCACTACATACAAACAAATGCTCCGCTCA        60

T  G  S  L  S  N  L  F  S  E  S  D  S  P  Y  L  V  S  R  N
ACTGGTTCGCTATCCAATTTGTTCTCTGAAAGTGACTCGCCTTATTTGGTCTCAAGGAAT        120

V  E  N  A  F  C  E  A  F  G  A  E  N  L  G  R  S  D  C  S
GTGGAAAATGCTTTTTGTGAAGCATTTGGAGCTGAAAACTTGGGGAGGTCAGACTGTTCT        180

A  D  A  S  L  N  R  V  G  I  G  I  K  T  F  L  H  G  N  G
GCTGACGCTTCATTAAATCGTGTCGGAATTGGTATTAAGACTTTTCTTCATGGTAATGGT        240

H  T  L  Q  K  V  A  E  F  N  K  D  S  D  L  Y  R  G  K  S
CATACTCTTCAAAAAGTAGCTGAATTCAATAAAGACTCAGACTTGTATCGTGGGAAATCT        300

P  K  E  L  I  N  T  V  A  S  L  R  N  E  R  I  E  F  T  K
CCAAAAGAGCTAATAAACACGGTTGCTTCTCTCCGTAACGAGAGAATTGAATTTACTAAA        360

R  T  Y  G  I  D  S  M  I  Y  H  C  V  T  R  K  P  G  K  I
AGAACATATGGTATTGATTCAATGATATACCACTGTGTAACAAGAAAGCCAGGGAAAATT        420

L  I  F  E  E  P  M  D  L  V  E  I  S  S  I  T  N  V  K  V
CTTATTTTTGAAGAGCCAATGGACTTGGTTGAAATCTCCTCAATTACAAATGTGAAAGTA        480

S  N  N  R  N  T  I  T  F  E  D  G  L  H  E  Y  S  F  N  V
AGTAACAACAGAAATACAATCACCTTTGAAGACGGTCTACACGAATACAGCTTTAATGTC        540

T  K  S  T  L  Y  K  R  F  I  T  D  K  P  I  E  E  I  N  V
ACTAAGAGCACCCTTTATAAGCGTTTTATCACTGATAAACCTATTGAAGAAATTAATGTT        600
```

Fig 2A

```
  E   I   L   E   N   P   Y   H   E   L   A   K   L   F   G   F   E   I   P   K
GAAATCTTAGAAAATCCTTATCATGAATTGGCTAAACTATTTGGCTTTGAAATTCCAAAA               660

I   P   A   P   T   V   N   P   F   E   N   L   E   H   V   I   L   P   L   F
ATTCCAGCACCAACTGTCAATCCTTTTGAAAACCTTGAGCACGTTATTCTTCCACTCTTT               720

S   D   R   G   S   K   R   H   V   P   E   K   S   G   L   N   Q   W   N   A
TCAGACCGTGGCTCAAAGCGTCATGTACCAGAAAAAAGCGGTCTAAACCAATGGAATGCT               780

L   G   R   P   R   N   P   N   E   I   Y   I   P   I   P   K   W   I   H   N
TTAGGTCGACCACGAAACCCTAACGAGATTTATATACCAATTCCAAAATGGATTCATAAT               840

V   F   P   T   F   F   P   A   R   D   K   P   F   Q   L   R   L   P   D   K
GTATTCCCAACATTTTTCCCAGCTCGTGATAAACCTTTTCAGTTACGCTTGCCAGACAAA               900

S   L   L   S   A   K   V   C   Q   D   N   S   K   A   L   M   S   N   P   N
TCGCTTTTATCAGCCAAGGTATGCCAAGACAATAGTAAAGCACTTATGTCTAATCCAAAT               960

S   A   L   G   E   W   L   L   R   Q   V   M   N   L   E   E   K   E   L   L
AGTGCTCTTGGAGAATGGCTACTAAGACAAGTTATGAACTTAGAGGAAAAAGAACTTCTA               1020

T   Y   E   M   L   E   R   L   N   I   D   S   V   I   V   Y   K   H   S   E
ACCTATGAAATGCTGGAAAGACTAAATATTGACTCAGTAATTGTTTATAAACACAGCGAA               1080

Q   H   Y   S   I   D   F   C   E   M   G   S   Y   D   E   F   E   N   E   N
CAACATTACTCCATTGATTTTGTGAAATGGGTTCTTATGATGAATTTGAAAATGAAAAC               1140

K   *
AAATAA                                                                     1146
```

Fig 2B

```
TCATGTTCCCATATTCTTTTAATGTTCCAATCCTTTTCCTCGTAATATTTATTAACTTCC      60
TTATCTCTTTTTTATTCTTTCGAGTTTTTTCTCCCAATATTCCGTATTACTTTTTGGT      120
ATATTCCCGTGTTTTCACACGCATGCCAGAAACAAGAATCAATGAATATGACTATTTTA     180
TATTTCTGTATTACTATATCTGGACTACCGTATAATTCTTAACATTTTTTCGGAATCTT     240
ATTCCACGGTGCCATAGTTCTTTAGTAACCTTATCTTCTAATTTGAACGAGATTTGATT     300
GCCTGCATGTTTTCTTTCTTTGTCTTTTGAAACCGTGTCAGTCATAGAAGAGTCCTCC      360
AAAGCCACAATAATTGTATTCTATAAACGAGGAAGCAAGCCCTCAAGCTTACCCCCTCTT    420
AGTTCCTTTTTGCCTACTTATTATTTGTTTTCATTTCAAATTCATCATAAGAACCCA      480
TTTCACAAAAATCAATGGAGTAATGTGTTCGCTGTTATAGGTTAGAAGTTCTTTTTCCTCTAAGTTCATAACTT  540
TATTTAGTCTTTCCAGCATTCATTCTTCCAAGAGTTAGAAGTTCATAGTGCTTTACTATTGT  600
GTCTTAGTAGCCATTTCTCCAAGAGTCACTATTGGACATAAGTGCTTTACTATTGT     660
CTTGGCATACCTTGGCTGATAAAAGCGATTGTCTGGCAAGCGTAACTGAAAAGGTTTAT     720
CACGAGCTGGGAAAAATGTGGAATACATTATGAATCCATTTGGTTTAGACGCTTTTTCTG    780
TCTCGTTAGGGTTTCGTGGTCGAGCCACGGTCTGAATTTCAAAGCCAAATAGTTAGCCA    840
GTACATGACGCTTGAGCCACGGTGGTGCTGGAATTTCAAAGCCAAATAGTTAGCCA      900
CAAAAGGATTGACAGTTGGTGCTGGAATTTCAAAGCCAAATAGTTAGCCA       960
ATTCATGATAAGGATTTTCTAAGATTTCAACATTAATTCTTCAATAGGTTTATCAGTGA    1020
TAAACGCTTATAAAGGGTGCTCTTAGTGACATTAAAGCTGTATTCGTGTAGACCGTCTT    1080
```

Fig. 3A

```
CAAAGGTGATTGTATTCTGTTGTTACTTACTTTCACATTGTAATTGAGGAGATTTCAA      1140
CCAAGTCCATTGGCTCTTCAAAAATAAGAATTTCCCTGGCTTTCTTGTTACACAGTGGT      1200
ATATCATTGAATCAATACCATATGTTCTTTTAGTAAATTCAATTCTCTCGTTACGGAGAG    1260
AAGCAACCGTGTTTATTAGCTCTCTTTTGGAGATTTCCCACGATACAAGTCTGAGTCTTTAT  1320
TGAATTCAGCTACTTTTTGAAGAGTATGACCATTACCATGAGAAAAGTCTTAATACCAA     1380
TTCCGACACGATTTAATGAAGCGTCAGCAGAACAGTCTGACCTCCCCAAGTTTTCAGCTC    1440
CAAATGCTTCACAAAAAGCATTTCCACATTCCTTGAGACCAAATAAGGCGAGTCACTTT     1500
CAGAGAACAAATTGGATAGCGAACCAGTTGAGCGGAGCATTTGTTTGTATGTAGTGCAGT    1560
TGATGGCTGGTTGATTAGTAGTATAGAACATTATTTTCCTCCTCTTTTATGCTTGTCATTTC  1620
TTCTTTCAGACCCAAAGGTAGTCAGCTGATACGTTCAATGTTTCAGCTATTCTTTTGAA     1680
AGTGTCCAATGATGGAGTTCTATTTCACTTTCATATAGTGACCAAGTGCTTCTAGTGAC     1740
CCCGACTTTTTCAGCGATTGGCTGGGTAATAACCTACGAGCTTCTCTTGCATTTTGAAT     1800
ACGATTTCCAAGGAAAGTATCATTTTGCACCTCCAAGATTGTTGTTTTCAGAGTATC       1860
ACCAGAACCCCCGAAATAGTCCAAAGTTAGCTACAACAGCAAACAAATAATTAATCCAGCT   1920
TTGTTACTCTTAGCAACTTGTTACTAAAATTGATAAAGTTATTCATTTAATCCAGCT       1980
CTTATGCTAAAATTGCATTAGCGGACAAGCTTAATGTTTGCAAGGAGGTATAATTTTGAC    2040
TTATCGAGTAGTAGTATGTTTGCTGGGATAGGTGGAACTTGTTTAGGGTTTATCCAAGC     2100
TGGCGCTAGGATTGTCTGGGCAAATGAAATAGACAAAAATGCTTGTATTACTTATAGAAA    2160
TTATTTTGGGGATGCTTACTTACAAGAGAGGGTGACATTAACCTAATAGATAAAACTCCAT  2220
ACCTGAACTGGACATTTGATTGGAGGTTTCCTTGCCAAGCCTTCTCTATAGCTGGCTA      2280
```

Fig. 3B

```
TCGTAAAGGGTTTGAAGATGAAAGGGAAACGTGTCTTTCAAATATTAGAGGTATTGGA    2340
AGCACAAAGAAATGTTTATGGACACTTACCCCAAGCAATAATGCTTGAGAATGTAAAGAA  2400
CTTATTTACACATGATAGAGGTAATACGTACAGAGTAATAAAAGAGGCTTTGGAAGCCTT  2460
TGGTTATACCGTAAAAGCTGAGGTTCTTAATTCAATGGAATACGGTAACGTGCCACAAAA  2520
CAGAGAGCGGATTTATATTGTAGGTTTTCAAGATGAGAGCCAAGCTGAAAGGTTTAGCTT  2580
TCCAGACCCAATTCCTTAACAAATCAACTTAATGATGTAATTGACCGAACTCGGAGAGT   2640
TGATAAAGATATTATTATGAAACCTCTCAATATTATGATATGTTGCGAGAAGCCAT      2700
GGACAGTACAGATACAACTTATCAAATAAGACGTATATATGTTCGAGAAAATAGAAGCAA  2760
TGTTTGTCCTACACTGACAGCGAATGGGAACTGGAGGGCATAATGTTCCTATTGTATT    2820
AGACTTTGAAAATAATAAGAAAACTAACACCAGAAGAATGCTTACTATTGCAAGGTTT    2880
CCCAGCTGACTATCATTTTCCAGAAGGCATGGCAAACACTCACAAATATAAACAAGCTGG  2940
TAACTCTGTTACGGTGCCAGTTATAAGAAGAACATGAATATGCAATAGCTGAATAA      3000
CATTGGAATGAATATAAATCAAGAACATGAATATGCAATAGCTGAATAA             3049
```

Fig. 3C

SEQUENCE LISTING

<160> NUMBER OF SEQ ID NOS: 19

<210> SEQ ID NO 1
<211> LENGTH: 1014
<212> TYPE: DNA
<213> ORGANISM: Bacillus licheniformis

<400> SEQUENCE: 1

```
ttgacttatc gagtaggtag tatgtttgct gggataggtg gaacttgttt agggtttatc      60
caagctggcg ctaggattgt ctgggcaaat gaaatagaca aaaatgcttg tattacttat     120
agaaattatt tgggatgc ttacttacaa gagggtgaca ttaacctaat agataaaaac      180
tccatacctg aactggacat tttgattgga ggttttcctt gccaagcctt ctctatagct     240
ggctatcgta aagggtttga agatgaaagg ggaaacgtgt tctttcaaat attagaggta     300
ttggaagcac aaagaaatgt ttatgacac ttaccccaag caataatgct tgagaatgta     360
aagaacttat ttacacatga tagaggtaat acgtacagag taataaaaga ggctttggaa     420
gcctttggtt ataccgtaaa agctgaggtt cttaattcaa tggaatacgg taacgtgcca     480
caaaacagag agcggattta tattgtaggt tttcaagatg agagccaagc tgaaaggttt     540
agcttttccag acccaattcc tttaacaaat caacttaatg atgtaattga ccgaactcgg     600
agagttgata aaagatatta ttatgatgaa acctctcaat attatgatat gttgcgagaa     660
gccatggaca gtacagatac aacttatcaa ataagacgta tatatgttcg agaaaataga     720
agcaatgttt gtcctacact gacagcgaat atgggaactg gagggcataa tgttcctatt     780
gtattagact ttgaaaataa tataagaaaa ctaacaccag aagaatgctt actattgcaa     840
ggtttcccag ctgactatca ttttccagaa ggcatggcaa acactcacaa atataaacaa     900
gctggtaact ctgttacggt gccagttata agaagaattg ccactaatat tattagcgta     960
ttgaacattg gaatgaatat aaatcaagaa catgaatatg caatagctga ataa          1014
```

<210> SEQ ID NO 2
<211> LENGTH: 337
<212> TYPE: PRT
<213> ORGANISM: Bacillus licheniformis

<400> SEQUENCE: 2

Met Thr Tyr Arg Val Gly Ser Met Phe Ala Gly Ile Gly Gly Thr Cys
1               5                   10                  15

Leu Gly Phe Ile Gln Ala Gly Ala Arg Ile Val Trp Ala Asn Glu Ile
            20                  25                  30

Asp Lys Asn Ala Cys Ile Thr Tyr Arg Asn Tyr Phe Gly Asp Ala Tyr
        35                  40                  45

Leu Gln Glu Gly Asp Ile Asn Leu Ile Asp Lys Asn Ser Ile Pro Glu
    50                  55                  60

Leu Asp Ile Leu Ile Gly Gly Phe Pro Cys Gln Ala Phe Ser Ile Ala

```
                65                  70                  75                  80
Gly Tyr Arg Lys Gly Phe Glu Asp Glu Arg Gly Asn Val Phe Phe Gln
                85                  90                  95

Ile Leu Glu Val Leu Glu Ala Gln Arg Asn Val Tyr Gly His Leu Pro
            100                 105                 110

Gln Ala Ile Met Leu Glu Asn Val Lys Asn Leu Phe Thr His Asp Arg
            115                 120                 125

Gly Asn Thr Tyr Arg Val Ile Lys Glu Ala Leu Glu Ala Phe Gly Tyr
        130                 135                 140

Thr Val Lys Ala Glu Val Leu Asn Ser Met Glu Tyr Gly Asn Val Pro
145                 150                 155                 160

Gln Asn Arg Glu Arg Ile Tyr Ile Val Gly Phe Gln Asp Glu Ser Gln
                165                 170                 175

Ala Glu Arg Phe Ser Phe Pro Asp Pro Ile Pro Leu Thr Asn Gln Leu
            180                 185                 190

Asn Asp Val Ile Asp Arg Thr Arg Arg Val Asp Lys Arg Tyr Tyr Tyr
            195                 200                 205

Asp Glu Thr Ser Gln Tyr Tyr Asp Met Leu Arg Glu Ala Met Asp Ser
        210                 215                 220

Thr Asp Thr Thr Tyr Gln Ile Arg Arg Ile Tyr Val Arg Glu Asn Arg
225                 230                 235                 240

Ser Asn Val Cys Pro Thr Leu Thr Ala Asn Met Gly Thr Gly Gly His
                245                 250                 255

Asn Val Pro Ile Val Leu Asp Phe Glu Asn Asn Ile Arg Lys Leu Thr
            260                 265                 270

Pro Glu Glu Cys Leu Leu Leu Gln Gly Phe Pro Ala Asp Tyr His Phe
            275                 280                 285

Pro Glu Gly Met Ala Asn Thr His Lys Tyr Lys Gln Ala Gly Asn Ser
        290                 295                 300

Val Thr Val Pro Val Ile Arg Arg Ile Ala Thr Asn Ile Ile Ser Val
305                 310                 315                 320

Leu Asn Ile Gly Met Asn Ile Asn Gln Glu His Glu Tyr Ala Ile Ala
                325                 330                 335

Glu

<210> SEQ ID NO 3
<211> LENGTH: 1146
<212> TYPE: DNA
<213> ORGANISM: Bacillus licheniformis

<400> SEQUENCE: 3
atgttctata ctaatcaacc agccatcaac tgcactacat acaaacaaat gctccgctca    60
actggttcgc tatccaattt gttctctgaa agtgactcgc ttatttggt ctcaaggaat    120 gtggaaaatg cttttgtga agcatttgga gctgaaaact ggggaggtc agactgttct    180 gctgacgctt cattaaatcg tgtcggaatt ggtattaaga cttttcttca tggtaatggt    240
catactcttc aaaagtagc tgaattcaat aaagactcag acttgtatcg tgggaaatct    300
ccaaaagagc taataaacac ggttgcttct ctccgtaacg agagaattga atttactaaa    360
agaacatatg gtattgattc aatgatatac cactgtgtaa caagaaagcc agggaaaatt    420
cttatttttg aagagccaat ggacttggtt gaaatctcct caattacaaa tgtgaaagta    480
agtaacaaca gaaatacaat cacctttgaa gacggtctac acgaatacag ctttaatgtc    540
actaagagca cccttttataa gcgttttatc actgataaac ctattgaaga aattaatgtt    600
```

-continued

```
gaaatcttag aaaatcctta tcatgaattg ctaaactat ttggctttga aattccaaaa    660
attccagcac caactgtcaa tccttttgaa aaccttgagc acgttattct tccactcttt    720
tcagaccgtg gctcaaagcg tcatgtacca gaaaaaagcg gtctaaacca atggaatgct    780
ttaggtcgac cacgaaaccc taacgagatt tatataccaa ttccaaaatg gattcataat    840
gtattcccaa cattttttccc agctcgtgat aaaccttttc agttacgctt gccagacaaa    900
tcgcttttat cagccaaggt atgccaagac aatagtaaag cacttatgtc taatccaaat    960
agtgctcttg gagaatggct actaagacaa gttatgaact tagaggaaaa agaacttcta   1020
acctatgaaa tgctggaaag actaaatatt gactcagtaa ttgtttataa acacagcgaa   1080
caacattact ccattgattt ttgtgaaatg ggttcttatg atgaatttga aaatgaaaac   1140
aaataa                                                             1146
```

<210> SEQ ID NO 4
<211> LENGTH: 381
<212> TYPE: PRT
<213> ORGANISM: Bacillus licheniformis

<400> SEQUENCE: 4

```
Met Phe Tyr Thr Asn Gln Pro Ala Ile Asn Cys Thr Thr Tyr Lys Gln
1               5                   10                  15

Met Leu Arg Ser Thr Gly Ser Leu Ser Asn Leu Phe Ser Glu Ser Asp
            20                  25                  30

Ser Pro Tyr Leu Val Ser Arg Asn Val Glu Asn Ala Phe Cys Glu Ala
        35                  40                  45

Phe Gly Ala Glu Asn Leu Gly Arg Ser Asp Cys Ser Ala Asp Ala Ser
    50                  55                  60

Leu Asn Arg Val Gly Ile Gly Ile Lys Thr Phe Leu His Gly Asn Gly
65                  70                  75                  80

His Thr Leu Gln Lys Val Ala Glu Phe Asn Lys Asp Ser Asp Leu Tyr
                85                  90                  95

Arg Gly Lys Ser Pro Lys Glu Leu Ile Asn Thr Val Ala Ser Leu Arg
            100                 105                 110

Asn Glu Arg Ile Glu Phe Thr Lys Arg Thr Tyr Gly Ile Asp Ser Met
        115                 120                 125

Ile Tyr His Cys Val Thr Arg Lys Pro Gly Lys Ile Leu Ile Phe Glu
    130                 135                 140

Glu Pro Met Asp Leu Val Glu Ile Ser Ser Ile Thr Asn Val Lys Val
145                 150                 155                 160

Ser Asn Asn Arg Asn Thr Ile Thr Phe Glu Asp Gly Leu His Glu Tyr
                165                 170                 175

Ser Phe Asn Val Thr Lys Ser Thr Leu Tyr Lys Arg Phe Ile Thr Asp
            180                 185                 190

Lys Pro Ile Glu Glu Ile Asn Val Glu Ile Leu Glu Asn Pro Tyr His
        195                 200                 205

Glu Leu Ala Lys Leu Phe Gly Phe Glu Ile Pro Lys Ile Pro Ala Pro
    210                 215                 220

Thr Val Asn Pro Phe Glu Asn Leu Glu His Val Ile Leu Pro Leu Phe
225                 230                 235                 240

Ser Asp Arg Gly Ser Lys Arg His Val Pro Glu Lys Ser Gly Leu Asn
                245                 250                 255

Gln Trp Asn Ala Leu Gly Arg Pro Arg Asn Pro Asn Glu Ile Tyr Ile
            260                 265                 270
```

```
Pro Ile Pro Lys Trp Ile His Asn Val Phe Pro Thr Phe Phe Pro Ala
            275                 280                 285

Arg Asp Lys Pro Phe Gln Leu Arg Leu Pro Asp Lys Ser Leu Leu Ser
            290                 295                 300

Ala Lys Val Cys Gln Asp Asn Ser Lys Ala Leu Met Ser Asn Pro Asn
305                 310                 315                 320

Ser Ala Leu Gly Glu Trp Leu Leu Arg Gln Val Met Asn Leu Glu Glu
                325                 330                 335

Lys Glu Leu Leu Thr Tyr Glu Met Leu Glu Arg Leu Asn Ile Asp Ser
                340                 345                 350

Val Ile Val Tyr Lys His Ser Glu Gln His Tyr Ser Ile Asp Phe Cys
            355                 360                 365

Glu Met Gly Ser Tyr Asp Glu Phe Glu Asn Glu Asn Lys
            370                 375                 380

<210> SEQ ID NO 5
<211> LENGTH: 3049
<212> TYPE: DNA
<213> ORGANISM: Bacillus licheniformis

<400> SEQUENCE: 5
tcatgttccc atattctttt aatgttccaa tccttttcct cgtaatattt attaacttcc      60
ttatctcttt ttttatttct ttcgagtttt ttctcccaat attccgtatt actttttggt     120
atattcccgt gttttcaca cgcatgccag aaacaagaat caatgaatat gactatttta     180
tatttctgta ttactatatc tggactaccg tataatttct taacattttt tcggaatctt     240
attccacggt gccatagttc tttagtaacc ttatcttcta attttgaacg agatttgatt     300
gcctgcatgt ttttcttct tgttcttttt gaaaccgtgt cagtcataga agagtcctcc     360
aaagccacaa taattgtatt ctataaacga ggaagcaagc cctcaagctt accccctctt     420
agttcctttt ttgcctactt atttatttgt tttcattttc aaattcatca taagaaccca     480
tttcacaaaa atcaatggag taatgttgtt cgctgtgttt ataaacaatt actgagtcaa     540
tatttagtct ttccagcatt tcataggtta gaagttcttt ttcctctaag ttcataactt     600
gtcttagtag ccattctcca agagcactat ttggattaga cataagtgct ttactattgt     660
cttggcatac cttggctgat aaaagcgatt tgtctggcaa gcgtaactga aaaggtttat     720
cacgagctgg gaaaaatgtt gggaatacat tatgaatcca ttttggaatt ggtatataaa     780
tctcgttagg gtttcgtggt cgacctaaag cattccattg gttagaccg cttttttctg     840
gtacatgacg ctttgagcca cggtctgaaa agagtggaag aataacgtgc tcaaggtttt     900
caaaaggatt gacagttggt gctggaattt ttggaatttc aaagccaaat agtttagcca     960
attcatgata aggattttct aagatttcaa cattaatttc ttcataggt ttatcagtga    1020
taaaacgctt ataagggtg ctcttagtga cattaaagct gtattcgtgt agaccgtctt    1080
caaaggtgat tgtatttctg ttgttactta ctttcacatt tgtaattgag gagatttcaa    1140
ccaagtccat tggctcttca aaataagaa ttttccctgg ctttcttgtt acacagtggt    1200
atatcattga atcaatacca tatgttcttt tagtaaattc aattctctcg ttacggagag    1260
aagcaaccgt gttattagc tcttttggag atttcccacg atacaagtct gagtctttat    1320
tgaattcagc tacttttga agagtatgac cattaccatg aagaaaagtc ttaataccaa    1380
ttccgacacg atttaatgaa gcgtcagcag aacagtctga cctccccaag ttttcagctc    1440
caaatgcttc acaaaaagca ttttccacat tccttgagac caaataaggc gagtcacttt    1500
```

-continued

```
cagagaacaa attggatagc gaaccagttg agcggagcat tgtttgtat gtagtgcagt      1560 tgatggctgg ttgattagta tagaacatta tttttcctcc tcttttatgc ttgtcatttc      1620
ttctttcaga cccaaaaggt agtcagctga tacgttcaat gtttcagcta ttcttttgaa      1680
agtgtccaat gatggagttc tattttcact ttcatatagt gaccaagtgc ttctagtgac      1740
cccgactttt tcagcgattt ggctgggtaa taacctacga gcttctcttg cattttgaat      1800
acgatttcca aggaaaggta tcattttgc acctccaaga tttgttgttt tcagagtatc       1860
accagaaccc ccgaaaatag tccaaagtta gctaacagca acaaataaa aataaataag       1920 ttgtttactc ttagcaaact tgttactaaa atttgataaa gttattcatt taatccagct      1980
cttatgctaa aattgcatta gcggacaagc ttaatgtttg caaggaggta taattttgac      2040
ttatcgagta ggtagtatgt tgctgggat aggtggaact tgtttagggt ttatccaagc       2100
tggcgctagg attgtctggg caaatgaaat agacaaaaat gcttgtatta cttatagaaa      2160 ttatttggg gatgcttact tacaagaggg tgacattaac ctaatagata aaaactccat       2220
acctgaactg gacattttga ttggaggttt tccttgccaa gccttctcta tagctggcta      2280
tcgtaaaggg tttgaagatg aaggggaaa cgtgttcttt caaatattag aggtattgga       2340
agcacaaaga aatgtttatg gacacttacc ccaagcaata atgcttgaga atgtaaagaa      2400
cttatttaca catgatagag gtaatacgta cagagtaata aaagaggctt tggaagcctt      2460
tggttatacc gtaaaagctg aggttcttaa ttcaatggaa tacggtaacg tgccacaaaa      2520
cagagagcgg atttatattg taggttttca agatgagagc caagctgaaa ggtttagctt      2580
tccagaccca attcctttaa caaatcaact taatgatgta attgaccgaa ctcggagagt      2640
tgataaaaga tattattatg atgaaacctc tcaatattat gatatgttgc gagaagccat      2700
ggacagtaca gatacaactt atcaaataag acgtatatat gttcgagaaa atagaagcaa      2760
tgtttgtcct acactgacag cgaatatggg aactggaggg cataatgttc ctattgtatt      2820
agactttgaa aataatataa gaaaactaac accagaagaa tgcttactat tgcaaggttt      2880
cccagctgac tatcattttc cagaaggcat ggcaaacact cacaaatata aacaagctgg      2940
taactctgtt acggtgccag ttataagaag aattgccact aatattatta gcgtattgaa      3000
cattggaatg aatataaatc aagaacatga atatgcaata gctgaataa               3049
```

<210> SEQ ID NO 6
<211> LENGTH: 26
<212> TYPE: DNA
<213> ORGANISM: Bacillus licheniformis

<400> SEQUENCE: 6

```
gagctctgca aggaggtata attttg                                            26
```

<210> SEQ ID NO 7
<211> LENGTH: 27
<212> TYPE: DNA
<213> ORGANISM: Bacillus licheniformis

<400> SEQUENCE: 7

```
acgcgtttat tcagctattg catattc                                           27
```

<210> SEQ ID NO 8
<211> LENGTH: 37
<212> TYPE: DNA
<213> ORGANISM: Bacillus licheniformis

```
<400> SEQUENCE: 8
ccaggcctta agggccgcat gcgtccttct ttgtgct                              37

<210> SEQ ID NO 9
<211> LENGTH: 27
<212> TYPE: DNA
<213> ORGANISM: Bacillus licheniformis

<400> SEQUENCE: 9
gagctccttt caatgtgata catatga                                        27

<210> SEQ ID NO 10
<211> LENGTH: 24
<212> TYPE: DNA
<213> ORGANISM: Bacillus licheniformis

<400> SEQUENCE: 10
gcggccgctc gctttccaat ctga                                           24

<210> SEQ ID NO 11
<211> LENGTH: 24
<212> TYPE: DNA
<213> ORGANISM: Bacillus licheniformis

<400> SEQUENCE: 11
atcgatcagc ttggataaac ccta                                           24

<210> SEQ ID NO 12
<211> LENGTH: 26
<212> TYPE: DNA
<213> ORGANISM: Bacillus licheniformis

<400> SEQUENCE: 12
gagctctgca aggaggtata attttg                                         26

<210> SEQ ID NO 13
<211> LENGTH: 28
<212> TYPE: DNA
<213> ORGANISM: Bacillus licheniformis

<400> SEQUENCE: 13
cgtcgacgcc tttgcggtag tggtgctt                                       28

<210> SEQ ID NO 14
<211> LENGTH: 26
<212> TYPE: DNA
<213> ORGANISM: Bacillus licheniformis

<400> SEQUENCE: 14
ggtaccatgt tctatactaa tcaacc                                         26

<210> SEQ ID NO 15
<211> LENGTH: 26
<212> TYPE: DNA
<213> ORGANISM: Bacillus licheniformis

<400> SEQUENCE: 15
ggatccttat tgttttcat tttcaa                                          26

<210> SEQ ID NO 16
<211> LENGTH: 24
<212> TYPE: DNA
<213> ORGANISM: Bacillus licheniformis
```

```
-continued

<400> SEQUENCE: 16
atcgatcagc ttggataaac ccta                                          24

<210> SEQ ID NO 17
<211> LENGTH: 30
<212> TYPE: DNA
<213> ORGANISM: Bacillus licheniformis

<400> SEQUENCE: 17
ttcacaagat ctatttcttc tttcagaccc                                    30

<210> SEQ ID NO 18
<211> LENGTH: 30
<212> TYPE: DNA
<213> ORGANISM: Bacillus licheniformis

<400> SEQUENCE: 18
agaaatagat cttgtgaaat gggttcttat                                    30

<210> SEQ ID NO 19
<211> LENGTH: 26
<212> TYPE: DNA
<213> ORGANISM: Bacillus licheniformis

<400> SEQUENCE: 19
gcggccgctc atgttcccat attctt                                        26
```

METHODS OF IMPROVING THE INTRODUCTION OF DNA INTO BACTERIAL CELLS

CROSS-REFERENCE TO RELATED APPLICATIONS

This application is a 35 U.S.C. 371 national application of PCT/US2007/085840 filed on Nov. 29, 2007 and claims priority from U.S. provisional application Ser. No. 60/861,896 filed on Nov. 29, 2006, which applications are fully incorporated herein by reference.

REFERENCE TO A DEPOSIT OF BIOLOGICAL MATERIAL

This application contains a reference to deposits of biological material, which deposits are incorporated herein by reference.

REFERENCE TO A SEQUENCE LISTING

This application contains a Sequence Listing in computer readable form. The computer readable form is incorporated herein by reference.

BACKGROUND OF THE INVENTION

1. Field of the Invention

The present invention relates to methods of improving the introduction of DNA into bacterial host cells.

2. Description of the Related Art

Type II restriction endonucleases are reportedly effective barriers to the introduction of DNA into bacteria (Briggs et al., 1994, *Applied and Environmental Microbiology* 60: 2006-2010; Accetto at al., 2005, *FEMS Microbiology Letters* 247: 177-183). Numerous Type II restriction endonucleases have been characterized in *Bacillus* and many commercially available restriction endonucleases have been isolated from *Bacillus* species (Roberts, et al., 2005, *Nucleic Acids Research* 33: 230-232).

Host DNA is protected from cleavage by its native restriction endonuclease due to host DNA modification by a corresponding DNA methyltransferase. The restriction endonuclease and DNA methyltransferase genes usually lie adjacent to each other in the genome and constitute a restriction-modification (R-M) system. These genes may be oriented transcriptionally in a convergent, divergent, or sequential manner. Although restriction endonucleases have little if any sequence similarity between one another, a limited amino acid motif, PD . . . D/EXK, has been found in many restriction endonucleases (Pingoud and Jettsch, 2001, *Nucleic Acids Research* 29: 3705-3727). In contrast, several general motifs have been found for the DNA methyltransferases (Kumar et al., 1994, *Nucleic Acids Research* 22: 1-10; Smith at al., 1990, *Proceedings of the National Academy of Sciences USA* 87: 826-830), which has allowed identification of restriction endonucleases by first Identifying their more homologous corresponding DNA methyltransferases.

The introduction of DNA into a bacterial host cell, e.g., *Bacillus licheniformis*, can be an inefficient process, resulting in few, if any, transformants. There is a need in the art for new methods of introducing a DNA into a bacterial host cell to improve the efficiency of obtaining transformants with the DNA.

The present invention relates to improved methods of introducing DNA into a bacterial host cell.

SUMMARY OF THE INVENTION

The present invention relates to isolated polynucleotides encoding DNA methyltransferases selected from the group consisting of (a) a polynucleotide encoding a polypeptide comprising an amino acid sequence having at least 60% sequence identity with amino acids 1 to 381 of SEQ ID NO: 2; (b) a polynucleotide comprising a nucleotide sequence having at least 60% sequence identity with nucleotides 1 to 1143 of SEQ ID NO: 1; (c) a polynucleotide that hybridizes under at least medium stringency conditions with nucleotides 1 to 1143 of SEQ ID NO: 1 or its full-length complementary strand; and (d) a polynucleotide encoding a variant comprising a substitution, deletion, and/or insertion of one or more amino acids of amino acids 1 to 381 of SEQ ID NO: 2.

The present invention also relates to isolated DNA methyltransferases selected from the group consisting of (a) a polypeptide comprising an amino acid sequence having at least 60% sequence identity with amino acids 1 to 381 of SEQ ID NO: 2; (b) a polypeptide encoded by a polynucleotide comprising a nucleotide sequence having at least 60% sequence identity with nucleotides 1 to 1143 of SEQ ID NO: 1; (c) a polypeptide encoded by a polynucleotide that hybridizes under at least medium stringency conditions with nucleotides 1 to 1143 of SEQ ID NO: 1 or its full-length complementary strand; and (d) a variant comprising a substitution, deletion, and/or insertion of one or more amino acids of amino acids 1 to 381 of SEQ ID NO: 2.

The present invention also relates to isolated polynucleotides encoding restriction endonucleases selected from the group consisting of (a) a polynucleotide encoding a polypeptide comprising an amino acid sequence having at least 60% sequence identity with amino acids 1 to 337 of SEQ ID NO: 4; (b) a polynucleotide comprising a nucleotide sequence having at least 60% sequence identity with nucleotides 1 to 1011 of SEQ ID NO: 3; (c) a polynucleotide that hybridizes under at least medium stringency conditions with nucleotides 1 to 1011 of SEQ ID NO: 3 or its full-length complementary strand; and (d) a polynucleotide encoding a variant comprising a substitution, deletion, and/or insertion of one or more amino acids of amino acids 1 to 337 of SEQ ID NO: 4.

The present invention also relates to isolated restriction endonucleases selected from the group consisting of (a) a polypeptide comprising an amino acid sequence having at least 60% sequence identity with amino acids 1 to 337 of SEQ ID NO: 4; (b) a polypeptide encoded by a polynucleotide comprising a nucleotide sequence having at least 60% sequence identity with nucleotides 1 to 1011 of SEQ ID NO: 3; (c) a polypeptide encoded by a polynucleotide that hybridizes under at least medium stringency conditions with nucleotides 1 to 1011 of SEQ ID NO: 3 or its full-length complementary strand; and (d) a variant comprising a substitution, deletion, and/or insertion of one or more amino acids of amino acids 1 to 337 of SEQ ID NO: 4.

The present invention also relates to methods of producing bacterial transformants, comprising:

(a) introducing a DNA into a first bacterial host cell comprising a polynucleotide encoding a DNA methyltransferase to methylate the DNA;

wherein the polynucleotide encoding the DNA methyltransferase is selected from the group consisting of (i) a polynucleotide encoding a polypeptide comprising an amino acid sequence having at least 60% sequence identity with amino acids 1 to 381 of SEQ ID NO: 2; (ii) a polynucleotide comprising a nucleotide sequence having at least 60% sequence identity with nucleotides 1 to 1143 of SEQ ID NO: 1; (iii) a polynucleotide that hybridizes under at least medium stringency conditions with nucleotides 1 to 1143 of SEQ ID NO: 1 or its full-length complementary strand; and (iv) a polynucleotide encoding a variant comprising a substitution, deletion, and/or insertion of one or more amino acids of amino acids 1 to 381 of SEQ ID NO: 2; and wherein the DNA methyltransferase has the same specificity as the DNA methyltransferase of amino acids 1 to 381 of SEQ ID NO: 2;

(b) transferring the methylated DNA from the first bacterial host cell into a second bacterial host cell; wherein the second bacterial host cell comprises a restriction endonuclease able to degrade the DNA but unable to degrade the methylated DNA; and (c) isolating transformants of the second bacterial host cell comprising the methylated DNA.

The present invention also relates to methods of producing bacterial transformants, comprising:

(a) methylating in vitro a DNA with a DNA methyltransferase to produce a methylated DNA;

wherein the DNA methyltransferase is selected from the group consisting of (i) a polypeptide comprising an amino acid sequence having at least 60% sequence identity with amino acids 1 to 381 of SEQ ID NO: 2; (ii) a polypeptide encoded by a polynucleotide comprising a nucleotide sequence having at least 60% sequence identity with nucleotides 1 to 1143 of SEQ ID NO: 1; (iii) a polypeptide encoded by a polynucleotide that hybridizes under at least medium stringency conditions with nucleotides 1 to 1143 of SEQ ID NO: 1 or its full-length complementary strand; and (iv) a variant comprising a substitution, deletion, and/or insertion of one or more amino acids of amino acids 1 to 381 of SEQ ID NO: 2; and wherein the DNA methyltransferase has the same specificity as the DNA methyltransferase of amino acids 1 to 381 of SEQ ID NO: 2;

(b) introducing the methylated DNA into a bacterial host cell, wherein the bacterial host cell comprises a restriction endonuclease able to degrade the DNA but unable to degrade the methylated DNA; and (c) isolating transformants of the bacterial host cell comprising the methylated DNA.

The present invention also relates to methods of producing bacterial transformants, comprising:

(a) introducing a DNA into a bacterial host cell comprising a polynucleotide encoding a restriction endonuclease, which is inactivated;

wherein the polynucleotide encoding the restriction endonuclease is selected from the group consisting of (i) a polynucleotide encoding a polypeptide comprising an amino acid sequence having at least 60% sequence identity with amino acids 1 to 337 of SEQ ID NO: 4; (ii) a polynucleotide comprising a nucleotide sequence having at least 60% sequence identity with nucleotides 1 to 1011 of SEQ ID NO: 3; (iii) a polynucleotide that hybridizes under at least medium stringency conditions with nucleotides 1 to 1011 of SEQ ID NO: 3 or its full-length complementary strand; and (iv) a polynucleotide encoding a variant comprising a substitution, deletion, and/or insertion of one or more amino acids of amino acids 1 to 337 of SEQ ID NO: 4;

wherein the restriction endonuclease has the same specificity as the restriction endonuclease of amino acids 1 to 337 of SEQ ID NO: 4; and wherein the inactivation of the polynucleotide encoding the restriction endonuclease prevents the introduced DNA from being digested by the restriction endonuclease and avoids the need to methylate the DNA with a DNA methyltransferase prior to introducing the DNA into the bacterial host cell; and (b) isolating transformants of the bacterial host cell comprising the DNA.

The present invention also relates to methods of producing a polypeptide having biological activity, comprising:

(a) cultivating a bacterial host cell comprising an introduced DNA encoding or involved in the expression of the polypeptide having biological activity under conditions conducive for production of the polypeptide;

wherein the DNA is methylated prior to being introduced into the bacterial host cell by a DNA methyltransferase selected from the group consisting of (i) a polypeptide comprising an amino acid sequence having at least 60% sequence identity with amino acids 1 to 381 of SEQ ID NO: 2; (ii) a polypeptide encoded by a polynucleotide comprising a nucleotide sequence having at least 60% sequence identity with nucleotides 1 to 1143 of SEQ ID NO: 1; (iii) a polypeptide encoded by a polynucleotide that hybridizes under at least medium stringency conditions with nucleotides 1 to 1143 of SEQ ID NO: 1 or its full-length complementary strand; and (iv) a variant comprising a substitution, deletion, and/or insertion of one or more amino acids of amino acids 1 to 381 of SEQ ID NO: 2;

wherein the DNA methyltransferase has the same specificity as the DNA methyltransferase of amino acids 1 to 381 of SEQ ID NO: 2; and wherein the methylation prevents the introduced DNA from being digested by a restriction endonuclease of the bacterial host cell; and (b) recovering the polypeptide having biological activity.

The present invention also relates to methods of producing a polypeptide having biological activity, comprising:

(a) cultivating a bacterial host cell comprising an introduced DNA encoding or involved in the expression of the polypeptide having biological activity under conditions conducive for production of the polypeptide;

wherein the bacterial host cell comprises a polynucleotide encoding a restriction endonuclease, which is inactivated;

wherein the polynucleotide encoding the restriction endonuclease is selected from the group consisting of (i) a polynucleotide encoding a polypeptide comprising an amino acid sequence having at least 60% sequence identity with amino acids 1 to 337 of SEQ ID NO: 4; (ii) a polynucleotide comprising a nucleotide sequence having at least 60% sequence identity with nucleotides 1 to 1011 of SEQ ID NO: 3; (iii) a polynucleotide that hybridizes under at least medium stringency conditions with nucleotides 1 to 1011 of SEQ ID NO: 3 or its full-length complementary strand; and (iv) a polynucleotide encoding a variant comprising a substitution, deletion, and/or insertion of one or more amino acids of amino acids 1 to 337 of SEQ ID NO: 4;

wherein the restriction endonuclease has the same specificity as the restriction endonuclease of amino acids 1 to 337 of SEQ ID NO: 4; and wherein the inactivation of the polynucleotide encoding the restriction endonuclease prevents the introduced DNA from being digested by the restriction endonuclease and avoids the need to methylate the DNA with a DNA methyltransferase prior to introducing the DNA into the bacterial host cell; and (b) recovering the polypeptide having biological activity.

The present invention also relates to the bacterial host cells described above.

The present invention also relates to methods of producing a mutant of a parent bacterial cell, comprising:

(a) introducing into a parent bacterial cell a DNA comprising a nucleic acid construct to inactivate a gene encoding a polypeptide in the parent bacterial cell, which results in a mutant cell producing less of the polypeptide than the parent cell when cultivated under the same conditions;

wherein the bacterial host cell comprises a polynucleotide encoding a restriction endonuclease, which is inactivated;

wherein the polynucleotide encoding the restriction endonuclease is selected from the group consisting of (i) a polynucleotide encoding a polypeptide comprising an amino acid sequence having at least 60% sequence identity with amino acids 1 to 337 of SEQ ID NO: 4; (ii) a polynucleotide comprising a nucleotide sequence having at least 60% sequence identity with nucleotides 1 to 1011 of SEQ ID NO: 3; (iii) a polynucleotide that hybridizes under at least medium stringency conditions with nucleotides 1 to 1011 of SEQ ID NO: 3 or its full-length complementary strand; and (iv) a polynucleotide encoding a variant comprising a substitution, deletion, and/or insertion of one or more amino acids of amino acids 1 to 337 of SEQ ID NO: 4;

wherein the restriction endonuclease has the same specificity as the restriction endonuclease of amino acids 1 to 337 of SEQ ID NO: 4; and wherein the inactivation of the polynucleotide encoding the restriction endonuclease prevents the introduced DNA from being digested by the restriction endonuclease and avoids the need to methylate the DNA with a DNA methyltransferase prior to introducing the DNA into the parent bacterial cell; and (b) isolating the mutant cell.

The present invention also relates to methods of producing a mutant of a parent bacterial cell, comprising:

(a) introducing into a parent bacterial cell a DNA comprising a nucleic acid construct to inactivate a gene encoding a polypeptide in the parent bacterial cell, which results in a mutant cell producing less of the polypeptide than the parent cell when cultivated under the same conditions;

wherein the DNA is methylated prior to being introduced into the bacterial host cell by a DNA methyltransferase selected from the group consisting of (i) a polypeptide comprising an amino acid sequence having at least 60% sequence identity with amino acids 1 to 381 of SEQ ID NO: 2; (ii) a polypeptide encoded by a polynucleotide comprising a nucleotide sequence having at least 60% sequence identity with nucleotides 1 to 1143 of SEQ ID NO: 1; (iii) a polypeptide encoded by a polynucleotide that hybridizes under at least medium stringency conditions with nucleotides 1 to 1143 of SEQ ID NO: 1 or its full-length complementary strand; and (iv) a variant comprising a substitution, deletion, and/or insertion of one or more amino acids of amino acids 1 to 381 of SEQ ID NO: 2;

wherein the DNA methyltransferase has the same specificity as the DNA methyltransferase of amino acids 1 to 381 of SEQ ID NO: 2; and wherein the methylation prevents the introduced DNA from being digested by a restriction endonuclease of the parent bacterial cell; and (b) isolating the mutant cell.

DESCRIPTION OF THE FIGURES

FIGS. 1A and 1B show the genomic DNA sequence and the deduced amino acid sequence of a *Bacillus licheniformis* M.Bli1904II DNA methyltransferase (SEQ ID NOs: 1 and 2, respectively).

FIGS. 2A and 2B show the genomic DNA sequence and the deduced amino acid sequence of a *Bacillus licheniformis* Bli1904II restriction endonuclease (SEQ ID NOs: 3 and 4, respectively).

FIG. 3 shows the genomic DNA sequence of a *Bacillus licheniformis* Bli1904II restriction-modification system comprising genes encoding Bli1904II restriction endonuclease and M.Bli1904II DNA methyltransferase (SEQ ID NO: 5). Reverse complement of the Bli1904II restriction endonuclease coding region is indicated by double underscoring and of the M.Bli1904II DNA methyltransferase coding region is indicated by single underscoring.

DEFINITIONS

Figure 4:
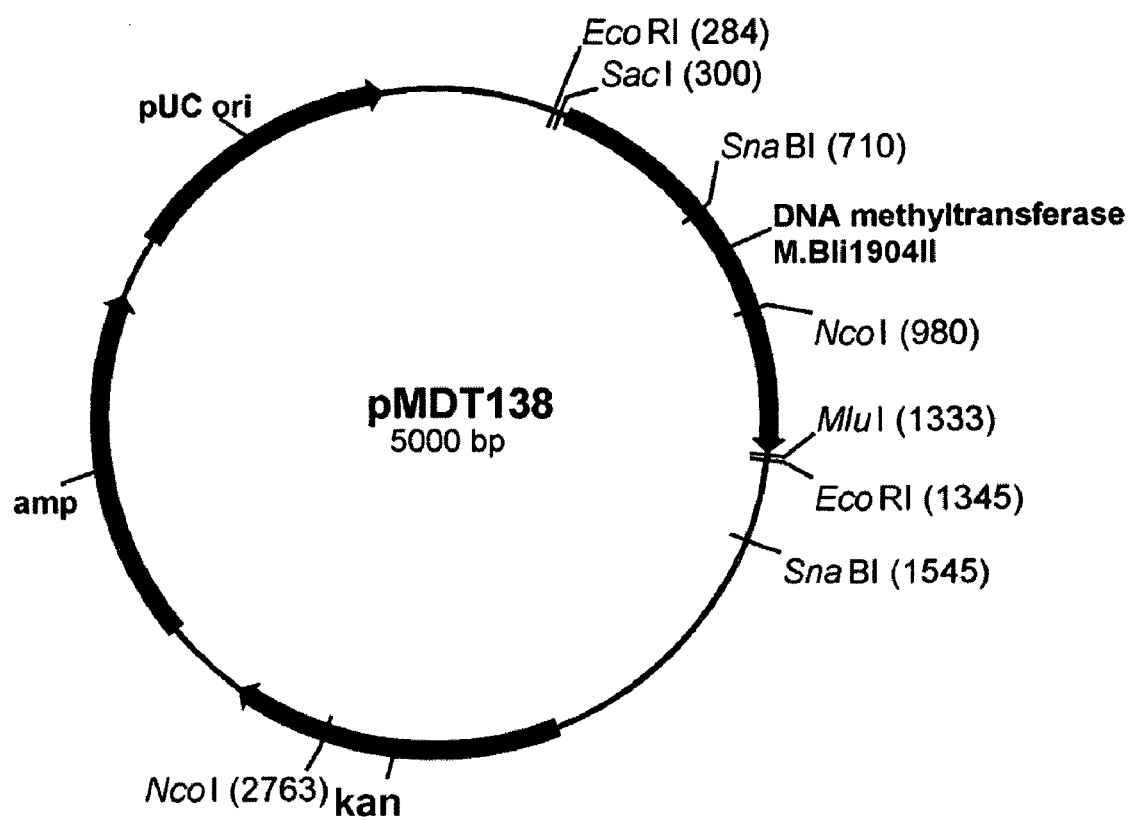
FIG. 4 shows a restriction map of pMDT138.

M.Bli1904II DNA methyltransferase: The term "M.Bli1904II DNA methyltransferase" is defined herein as a DNA (cytosine-5)-methyltransferase (EC 2.1.1.37) that catalyzes the transfer of a methyl group from S-adenosyl-L-methionine to DNA within the sequence GCNGC, resulting in S-adenosyl-L-homocysteine and DNA containing 5-methylcytosine. For purposes of the present invention, DNA methyltransferase activity is determined according to the procedure described by Pfeifer et al., 1983, *Biochim. Biophys. Acta* 740: 323-30. One unit of DNA methyltransferase activity is the amount required to protect 1 µg of λ DNA in 1 hour in a total reaction volume of 20 µl against cleavage by the corresponding restriction endonuclease.

The DNA methyltransferases of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the DNA methyltransferase activity of the polypeptide comprising or consisting of the amino acid sequence shown as amino acids 1 to 381 of SEQ ID NO: 2.

Bli1904II restriction endonuclease: The term "Bli1904II restriction endonuclease" is defined herein as a Type II restriction endonuclease that catalyzes the site-specific endonucleolytic cleavage of DNA to give specific double-stranded DNA fragments (EC 3.1.21.4). For purposes of the present invention, Bli1904II restriction endonuclease activity is determined according to established procedures for Type II restriction endonucleases (e.g., Jeltsch and Pingoud, 2001, *Methods Mol. Biol.* 160: 287-308). By definition, one unit of restriction endonuclease activity will completely digest one µg of substrate DNA in a 50 µl reaction in 60 minutes at 37° C.

The restriction endonucleases of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the restriction endonuclease activity of the polypeptide comprising or consisting of the amino acid sequence shown as amino acids 1 to 337 of SEQ ID NO: 4.

Restriction-modification system: The term "restriction-modification system" is defined herein as a restriction endonuclease, a corresponding DNA methyltransferase that protects DNA from cleavage by the restriction endonuclease, and the genes encoding these two enzymes.

Isolated polypeptide: The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Identity: The relatedness between two amino acid sequences or between two nucleotide sequences is described by the parameter "identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—no brief option) is used as the percent identity and is calculated as follows:

(Identical Residues×100)/(Length of Alignment−Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice of al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—no-brief option) is used as the percent identity and is calculated as follows:

(Identical Deoxyribonucleotides×100)/(Length of Alignment−Total Number of Gaps in Alignment)

Polypeptide fragment: The term "polypeptide fragment" is defined herein as a polypeptide having one or more amino acids deleted from the amino and/or carboxyl terminus of SEQ ID NO: 2 or SEQ ID NO: 4, or a homologous sequence thereof, wherein the fragment has DNA methyltransferase or restriction endonuclease activity, respectively. In a preferred aspect, a fragment of SEQ ID NO: 2 or a homolog thereof contains at least 320 amino acid residues, more preferably at least 340 amino acid residues, and most preferably at least 360 amino acid residues. In another preferred aspect, a fragment of SEQ ID NO: 4 or a homolog thereof contains at least 290 amino acid residues, more preferably at least 305 amino acid residues, and most preferably at least 320 amino acid residues.

Subsequence: The term "subsequence" is defined herein as a nucleotide sequence having one or more nucleotides deleted from the 5' and/or 3' end of SEQ ID NO: 1 or SEQ ID NO: 3, or a homologous sequence thereof, wherein the subsequence encodes a polypeptide fragment having DNA methyltransferase activity or restriction endonuclease, respectively. In a preferred aspect, a subsequence of SEQ ID NO: 1 or a homolog thereof contains at least 960 nucleotides, more preferably at least 1020 nucleotides, and most preferably at least 1080 nucleotides. In another preferred aspect, a subsequence of SEQ ID NO: 3 or a homolog thereof contains at least 870 nucleotides, more preferably at least 915 nucleotides, and most preferably at least 960 nucleotides.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Nucleic acid construct: The term "nucleic acid construct" as used herein refers to a nucleic acid molecule, either single- or double-stranded, which is isolated from a naturally occurring gene or is modified to contain segments of nucleic acids in a manner that would not otherwise exist in nature or is synthetic. The term nucleic acid construct is synonymous with the term "expression cassette" when the nucleic acid construct contains the control sequences required for expression of a coding sequence of the present invention.

Control sequences: The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, conjugation, and the like with a nucleic acid construct or expression vector.

Introduction: The term "introduction" and variations thereof are defined herein as the transfer of a DNA into a bacterial cell. The introduction of a DNA into a bacterial cell can be accomplished by any method known in the art, including, the not limited to, transformation, transfection, transduction, conjugation, and the like.

Transformation: The term "transformation" is defined herein as introducing a purified DNA into a bacterial cell so that the DNA is maintained as a chromosomal integrant or as a self-replicating extra-chromosomal vector. The term "transformation" shall be generally understood to include transfection, transduction, conjugation, and the like.

Transfection: The term "transfection" is defined herein as the transformation of a bacterial cell with a viral nucleic acid.

Transduction: The term "transduction" is defined herein as the packaging of DNA from a first bacterial cell into a virus particle and the transfer of that bacterial DNA to a second bacterial cell by infection of the second cell with the virus particle.

Conjugation: The term "conjugation" is defined herein as the transfer of DNA directly from one bacterial cell to another bacterial cell through cell-to-cell contact.

Transformant: The term "transformant" is defined herein to generally encompass any bacterial host cell into which a DNA has been introduced. Consequently, the term "transformant" included transfectants, conjugants, and the like.

Donor Cell: The term "donor cell" is defined herein as a cell that is the source of DNA introduced by any means to another cell.

Recipient cell: The term "recipient cell" is defined herein as a cell into which DNA is introduced.

Modification: The term "modification" means herein any chemical modification of the polypeptide consisting oft amino acids 1 to 381 of SEQ ID NO: 2 or amino acids 1 to 337 of SEQ ID NO: 4; or a homologous sequence thereof; as well as genetic manipulation of the DNA encoding such a polypeptide. The modification can be a substitution, a deletion and/or an insertion of one or more (several) amino acids as well as replacements of one or more (several) amino acid side chains.

Artificial variant: When used herein, the term "artificial variant" means a polypeptide having restriction endonuclease or DNA methyltransferase activity produced by an organism expressing a modified polynucleotide sequence of nucleotides 1 to 1043 of SEQ ID NO: 1 or nucleotides 1 to 1011 of SEQ ID NO: 3, respectively, or a homologous sequence thereof. The modified polynucleotide sequence is obtained through human intervention by modification of the nucleotide sequence disclosed in SEQ ID NO: 1 or SEQ ID NO: 3, or a homologous sequence thereof.

DETAILED DESCRIPTION OF THE INVENTION

The present invention relates to methods of producing bacterial transformants, comprising: (a) introducing a DNA into a first bacterial host cell comprising a polynucleotide encoding a DNA methyltransferase to methylate the DNA; wherein the polynucleotide encoding the DNA methyltransferase is selected from the group consisting of (i) a polynucleotide encoding a polypeptide comprising an amino acid sequence having at least 60% sequence identity with amino acids 1 to 381 of SEQ ID NO: 2; (ii) a polynucleotide comprising a nucleotide sequence having at least 60% sequence identity with nucleotides 1 to 1143 of SEQ ID NO: 1; (iii) a polynucleotide that hybridizes under at least medium stringency conditions with nucleotides 1 to 1143 of SEQ ID NO: 1 or its full-length complementary strand; and (iv) a polynucleotide encoding a variant comprising a substitution, deletion, and/or insertion of one or more amino acids of amino acids 1 to 381 of SEQ ID NO: 2; and wherein the DNA methyltransferase has the same specificity as the DNA methyltransferase of amino acids 1 to 381 of SEQ ID NO: 2; (b) transferring the methylated DNA from the first bacterial host cell into a second bacterial host cell; wherein the second bacterial host cell comprises a restriction endonuclease able to degrade the DNA but unable to degrade the methylated DNA; and (c) isolating transformants of the second bacterial host cell comprising the methylated DNA.

The present invention also relates to methods of producing bacterial transformants, comprising: (a) methylating in vitro a DNA with a DNA methyltransferase to produce a methylated DNA; wherein the DNA methyltransferase is selected from the group consisting of (i) a polypeptide comprising an amino acid sequence having at least 60% sequence identity with amino acids 1 to 381 of SEQ ID NO: 2; (ii) a polypeptide encoded by a polynucleotide comprising a nucleotide sequence having at least 60% sequence identity with nucleotides 1 to 1143 of SEQ ID NO: 1; (iii) a polypeptide encoded by a polynucleotide that hybridizes under at least medium stringency conditions with nucleotides 1 to 1143 of SEQ ID NO: 1 or its full-length complementary strand; and (iv) a variant comprising a substitution, deletion, and/or insertion of one or more amino acids of amino acids 1 to 381 of SEQ ID NO: 2; and wherein the DNA methyltransferase has the same specificity as the DNA methyltransferase of amino acids 1 to 381 of SEQ ID NO: 2; (b) introducing the methylated DNA into a bacterial host cell; wherein the bacterial host cell comprises a restriction endonuclease able to degrade the DNA but unable to degrade the methylated DNA; and (c) isolating transformants of the bacterial host cell comprising the methylated DNA The present invention also relates to methods of producing bacterial transformants, comprising: (a) introducing a DNA into a bacterial host cell comprising a polynucleotide encoding a restriction endonuclease, which is inactivated; wherein the polynucleotide encoding the restriction endonuclease is selected from the group consisting of (i) a polynucleotide encoding a polypeptide comprising an amino acid sequence having at least 60% sequence identity with amino acids 1 to 337 of SEQ ID NO: 4; (ii) a polynucleotide comprising a nucleotide sequence having at least 60% sequence identity with nucleotides 1 to 1011 of SEQ ID NO: 3; (iii) a polynucleotide that hybridizes under at least medium stringency conditions with nucleotides 1 to 1011 of SEQ ID NO: 3 or its full-length complementary strand; and (iv) a polynucleotide encoding a variant comprising a substitution, deletion, and/or insertion of one or more amino acids of amino acids 1 to 337 of SEQ ID NO: 4; wherein the restriction endonuclease has the same specificity as the restriction endonuclease of amino adds 1 to 337 of SEQ ID NO: 4, and wherein the inactivation of the polynucleotide encoding the restriction endonuclease prevents the introduced DNA from being digested by the restriction endonuclease and avoids the need to methylate the DNA with a DNA methyltransferase prior to introducing the DNA into the bacterial host cell, and (b) isolating transformants of the bacterial host cell comprising the DNA.

In the methods of the present invention, the introduction of a DNA into a bacterial host cell can be accomplished (1) by inactivating a polynucleotide encoding a restriction endonuclease of the bacterial host cell so the introduced DNA is not degraded by the restriction endonuclease or (2) by methylating the DNA with a DNA methyltransferase prior to its introduction into a bacterial host cell, so the introduced methylated DNA is not degraded by the restriction endonuclease of the bacterial host cell. The DNA methyltransferase or the restriction endonuclease may be native or foreign to the bacterial host cell.

In one aspect, the methylation of the DNA can be accomplished in vitro. For example, a DNA methyltransferase of the present invention can be recovered and used to methylate the DNA in the presence of S-adenosyl-L-methionine resulting in S-adenosyl-L-homocysteine and DNA containing 5-methylcytosine.

In another aspect, the methylation of the DNA can be accomplished in vivo. For example, the methylation of the DNA can be accomplished by cloning the polynucleotide encoding the DNA methyltransferase from the bacterial host cell (recipient cell) and expressing the DNA methyltransferase coding sequence in another bacterial cell (donor cell) where the DNA is introduced and methylated and then the methylated DNA is transferred or introduced into the bacterial host cell (recipient cell) from which the DNA methyltransferase coding sequence was isolated. In a further aspect, the polynucleotide encoding the DNA methyltransferase may be obtained from another organism that is not the recipient cell. In an even further aspect, the donor host cell may already contain a polynucleotide encoding a DNA methyltransferase or a homolog thereof of the present invention.

Introduction of the methylated DNA into the bacterial host cell can be accomplished by transfer from the first bacterial cell into the second bacterial cell, i.e., by conjugation, or by isolating the methylated DNA from the first bacterial cell and then introducing the isolated methylated DNA into the second bacterial cell by, for example, transformation.

The methods of the present invention increase the number of transformants obtained by at least 10-fold, preferably at least 100-fold, more preferably at least 1000-fold, even more preferably at least 10,000-fold, and most preferably at least 100,000-fold compared to conventional methods without inactivating a restriction endonuclease of the present invention or methylating a DNA with a DNA methyltransferase of the present invention.

Restriction Endonuclease Genes and DNA Methyltransferase Genes and Enzymes Thereof In a first aspect, the present invention relates to isolated polynucleotides encoding polypeptides having DNA methyltransferase activity comprising an amino acid sequence having a degree of sequence identity to amino acids 1 to 381 of SEQ ID NO: 2 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which have DNA methyltransferase activity (hereinafter "homologous polypeptides" or "homologs"). In a preferred aspect, the homologous polypeptides having DNA methyltransferase activity comprise an amino acid sequence that differs by ten amino acids, preferably by five amino acids, more preferably by four amino acids, even more preferably by three amino acids, most preferably by two amino acids, and even most preferably by one amino acid from amino acids 1 to 381 of SEQ ID NO: 2.

An isolated polynucleotide of the present invention preferably encodes a polypeptide having DNA methyltransferase activity comprising the amino acid sequence of SEQ ID NO: 2 or an allelic variant thereof; or a fragment thereof that has DNA methyltransferase activity. In a preferred aspect, a polypeptide comprises the amino acid sequence of SEQ ID NO: 2. In another preferred aspect, a polypeptide comprises amino acids 1 to 381 of SEQ ID NO: 2, or an allelic variant thereof; or a fragment thereof that has DNA methyltransferase activity. In another preferred aspect, a polypeptide comprises amino acids 1 to 381 of SEQ ID NO: 2. In another preferred aspect, a polypeptide consists of the amino acid sequence of SEQ ID NO: 2 or an allelic variant thereof; or a fragment thereof that has DNA methyltransferase activity. In another preferred aspect, a polypeptide consists of the amino acid sequence of SEQ ID NO: 2. In another preferred aspect, a polypeptide consists of amino acids 1 to 381 of SEQ ID NO: 2 or an allelic variant thereof; or a fragment thereof that has DNA methyltransferase activity. In another preferred aspect, a polypeptide consists of amino acids 1 to 381 of SEQ ID NO: 2.

The present invention also relates to isolated polynucleotides comprising nucleotide sequences that encode polypeptides having DNA methyltransferase activity. In a preferred aspect, the nucleotide sequence is set forth in SEQ ID NO: 1. In another more preferred aspect, the nucleotide sequence is the sequence contained in plasmid pMDT138 that is contained in *Escherichia coil* NRRL B-41967. In another preferred aspect, the nucleotide sequence is nucleotides 1 to 1143 of SEQ ID NO: 1. In another more preferred aspect, the nucleotide sequence is nucleotides 1 to 1143 of SEQ ID NO: 1 contained in plasmid pMDT138 that is contained in *Escherichia coli* NRRL B-41967. The present invention also encompasses nucleotide sequences that encode a polypeptide having the amino acid sequence of SEQ ID NO: 2, which differ from SEQ ID NO: 1 by virtue of the degeneracy of the genetic code. The present invention also relates to subsequences of SEQ ID NO: 1 that encode fragments of SEQ ID NO: 2 that have restriction endonuclease activity.

In another first aspect, the present invention relates to isolated polynucleotides encoding polypeptides having restriction endonuclease activity comprising an amino acid sequence having a degree of sequence identity to amino acids 1 to 337 of SEQ ID NO: 4 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which have restriction endonuclease activity (hereinafter "homologous polypeptides" or "homologs"). in a preferred aspect, the homologous polypeptides having restriction endonuclease activity comprise an amino acid sequence that differs by ten amino acids, preferably by five amino acids, more preferably by four amino acids, even more preferably by three amino acids, most preferably by two amino acids, and even most preferably by one amino acid from amino acids 1 to 337 of SEQ ID NO: 4.

An isolated polynucleotide of the present invention preferably encodes a polypeptide having restriction endonuclease activity comprising the amino acid sequence of SEQ ID NO: 4 or an allelic variant thereof; or a fragment thereof that has restriction endonuclease activity. In a preferred aspect, a polypeptide comprises the amino acid sequence of SEQ ID NO: 4. In another preferred aspect, a polypeptide comprises amino acids 1 to 337 of SEQ ID NO: 4, or an allelic variant thereof; or a fragment thereof that has restriction endonuclease activity. In another preferred aspect, a polypeptide comprises amino acids 1 to 337 of SEQ ID NO: 4. In another preferred aspect, a polypeptide consists of the amino acid sequence of SEQ ID NO: 4 or an allelic variant thereof; or a fragment thereof that has restriction endonuclease activity. In another preferred aspect, a polypeptide consists of the amino acid sequence of SEQ ID NO: 4. In another preferred aspect, a polypeptide consists of amino acids 1 to 337 of SEQ ID NO: 4 or an allelic variant thereof; or a fragment thereof that has restriction endonuclease activity. In another preferred aspect, a polypeptide consists of amino acids 1 to 337 of SEQ ID NO: 4.

The present invention also relates to isolated polynucleotides comprising nucleotide sequences that encode polypeptides having restriction endonuclease activity. In another preferred aspect, the nucleotide sequence is set forth in SEQ ID NO: 3. In another more preferred aspect, the nucleotide sequence is the sequence contained in plasmid pMDT156 that is contained in *Escherichia coli* NRRL B-41968. In another preferred aspect, the nucleotide sequence is nucleotides 1 to 1011 of SEQ ID NO: 3. in another more preferred aspect, the nucleotide sequence is nucleotides 1 to 1011 of SEQ ID NO: 3 contained in plasmid pMDT156 that is contained in *Escherichia coli* NRRL B-41968. The present invention also encompasses nucleotide sequences that encode a polypeptide having the amino acid sequence of SEQ ID NO: 4, which differ from SEQ ID NO: 3 by virtue of the degeneracy of the genetic code. The present invention also relates to subsequences of SEQ ID NO: 3 that encode fragments of SEQ ID NO: 4 that have restriction endonuclease activity.

In a second aspect, the present invention relates to isolated polynucleotides encoding polypeptides having DNA methyltransferase activity that hybridize under very low stringency conditions, preferably low stringency conditions, more preferably medium stringency conditions, more preferably medium-high stringency conditions, even more preferably high stringency conditions, and most preferably very high stringency conditions with (i) nucleotides 1 to 1143 of SEQ ID NO: 1, (ii) a subsequence of (i), or (iii) a full-length complementary strand of (i) or (ii) (J. Sambrook, E. F. Fritsch, and T. Maniatis, 1989, *Molecular Cloning, A Laboratory Manual*, 2d edition, Cold Spring Harbor, N.Y. A subsequence of SEQ ID NO: 3 contains at least 100 contiguous nucleotides or preferably at least 200 contiguous nucleotides. Moreover, the subsequence may encode a polypeptide fragment that has DNA methyltransferase activity.

In another second aspect, the present invention relates to isolated polynucleotides encoding polypeptides having restriction endonuclease activity that hybridize under very low stringency conditions, preferably low stringency conditions, more preferably medium stringency conditions, more preferably medium-high stringency conditions, even more preferably high stringency conditions, and most preferably very high stringency conditions with (i) nucleotides 1 to 1011 of SEQ ID NO: 3, (i) a subsequence of (i), or (iii) a full-length complementary strand of (i) or (i) (J. Sambrook, E. F. Fritsch, and T. Maniatis, 1989, supra). A subsequence of SEQ ID NO: 3 contains at least 100 contiguous nucleotides or preferably at least 200 contiguous nucleotides. Moreover, the subsequence may encode a polypeptide fragment that has restriction endonuclease activity.

The nucleotide sequence of SEQ ID NO: 1 or SEQ ID NO: 3, or a subsequence thereof, as well as the amino acid sequence of SEQ ID NO: 2 or SEQ ID NO: 4, or a fragment thereof, may be used to design a nucleic acid probe to identify and clone DNA encoding polypeptides having restriction endonuclease activity or DNA methyltransferase activity from strains of different genera or species according to methods well known in the art. In particular, such probes can be used for hybridization with the genomic DNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{32}P$, $^3H$, $^{35}S$, biotin, or avidin). Such probes are encompassed by the present invention.

A genomic DNA library prepared from such other organisms may, therefore, be screened for DNA that hybridizes with the probes described above and encodes a polypeptide having restriction endonuclease activity or DNA methyltransferase activity. Genomic DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1 or SEQ ID NO: 3, or a subsequence thereof, the carrier material is preferably used in a Southern blot.

For purposes of the present invention, hybridization indicates that the nucleotide sequence hybridizes to a labeled nucleic acid probe corresponding to the nucleotide sequence shown in SEQ ID NO: 1 or SEQ ID NO: 3, its full-length complementary strand, or a subsequence thereof, under very low to very high stringency conditions. Molecules to which the nucleic acid probe hybridizes under these conditions can be detected using X-ray film.

In a preferred aspect, the nucleic acid probe is a polynucleotide comprising a nucleotide sequence that encodes the polypeptide of SEQ ID NO: 2, or a subsequence thereof. In another preferred aspect, the nucleic acid probe is SEQ ID NO: 1 or its full-length complementary strand. In another preferred aspect, the nucleic acid probe is the mature polypeptide coding region of SEQ ID NO: 1. In another preferred aspect, the nucleic acid probe is the polynucleotide contained in plasmid pMDT138 which is contained in *Escherichia coli* NRRL B-41967, wherein the nucleotide sequence thereof encodes a polypeptide having DNA methyltransferase activity. In another preferred aspect, the nucleic acid probe is the mature polypeptide coding region contained in plasmid pMDT138 which is contained in *Escherichia coli* NRRL B-41967.

In another preferred aspect, the nucleic acid probe is a polynucleotide comprising a nucleotide sequence that encodes the polypeptide of SEQ ID NO: 4, or a subsequence thereof. In another preferred aspect, the nucleic acid probe is SEQ ID NO: 3 or its full-length complementary strand. In another preferred aspect, the nucleic acid probe is the mature polypeptide coding region of SEQ ID NO: 3. In another preferred aspect, the nucleic acid probe is the polynucleotide contained in plasmid pMDT156 which is contained in *Escherichia coil* NRRL B-41968, wherein the nucleotide sequence thereof encodes a polypeptide having restriction endonuclease activity. In another preferred aspect, the nucleic acid probe is the mature polypeptide coding region contained in plasmid pMDT156 which is contained in *Escherichia coli* NRRL B-41968.

For long probes of at least 100 nucleotides in length, very low to very high stringency conditions are defined as prehybridization and hybridization at 42° C. in 5×SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes of about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes of about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to isolated polynucleotides encoding artificial variants comprising a substitution, deletion, and/or insertion of one or more amino acids of SEQ ID NO: 2 or SEQ ID NO: 4, or a homologous sequence thereof; or the mature polypeptide thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *in, The Proteins, Academic* Press, New York. The most commonly occurring exchanges are Ala/Ser, Val/Ile, Asp/Glu, Thr/Ser, Ala/Gly, Ala/Thr, Ser/Asn, AlaNal, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., restriction endonuclease or DNA methyltransferase activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to a polypeptide according to the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223,409; WO 92/06204), and region-directed mutagenesis (Derbyshire et al., 1986, *Gene* 46: 145; Ner of al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of amino acids 1 to 381 of SEQ ID NO: 2 is 10, preferably 9, more preferably 8, more preferably 7, more preferably at most 6, more preferably 5, more preferably 4, even more preferably 3, most preferably 2, and even most preferably 1.

The total number of amino acid substitutions, deletions and/or insertions of amino acids 1 to 337 of SEQ ID NO: 4 is 10, preferably 9, more preferably 8, more preferably 7, more preferably at most 6, more preferably 5, more preferably 4, even more preferably 3, most preferably 2, and even most preferably 1.

The present invention also relates to isolated DNA methyltransferases selected from the group consisting of (a) a polypeptide comprising an amino acid sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% sequence identity with amino acids 1 to 381 of SEQ ID NO: 2; (b) a polypeptide encoded by a polynucleotide comprising a nucleotide sequence having preferably at least 60%, more preferably at least 65%, More preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% sequence identity with nucleotides 1 to 1143 of SEQ ID NO: 1; (c) a polypeptide encoded by a polynucleotide that hybridizes under preferably at least medium stringency conditions, more preferably at least medium-high stringency conditions, and most preferably at least high stringency conditions with nucleotides 1 to 1143 of SEQ ID NO: 1 or its full-length complementary strand; and (d) a variant comprising a substitution, deletion, and/or insertion of one or more amino acids of amino acids 1 to 381 of SEQ ID NO: 2.

The present invention also relates to isolated restriction endonucleases selected from the group consisting of (a) a polypeptide comprising an amino acid sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% sequence identity with amino acids 1 to 337 of SEQ ID NO: 4; (b) a polypeptide encoded by a polynucleotide comprising a nucleotide sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% sequence identity with nucleotides 1 to 1011 of SEQ ID NO: 3; (c) a polypeptide encoded by a polynucleotide that hybridizes under preferably at least medium stringency conditions, more preferably at least medium-high stringency conditions, and most preferably at least high stringency conditions with nucleotides 1 to 1011 of SEQ ID NO: 3 or its full-length complementary strand; and (d) a variant comprising a substitution, deletion, and/or insertion of one or more amino acids of amino acids 1 to 337 of SEQ ID NO: 4.

Inactivation of Restriction Endonuclease Genes

In the methods of the present invention, the introduction of a DNA into a bacterial host cell can be accomplished by inactivating a restriction endonuclease encoding polynucleotide native or foreign to the bacterial host cell so the introduced DNA is not degraded by the restriction endonuclease. The polynucleotide may be a component of a restriction-modification system.

Inactivation of a restriction endonuclease gene or a homolog thereof of the present invention in a bacterial host cell may be accomplished using methods well known in the art, for example, insertions, disruptions, replacements, or deletions of the gene. The portion of the gene to be inactivated may be, for example, the coding region or a regulatory element required for expression of the coding region. An example of such a regulatory or control sequence may be a promoter sequence or a functional part thereof, i.e., a part that is sufficient for affecting expression of the nucleotide sequence. Other control sequences for possible modification include, but are not limited to, a leader, propeptide sequence, signal sequence, transcription terminator, and transcriptional activator.

Inactivation of a restriction endonuclease gene of the present invention may be achieved by gene deletion techniques to eliminate or reduce the expression of the gene. Gene deletion techniques enable the partial or complete removal of the gene thereby eliminating its expression. In such methods, the deletion of the gene may be accomplished by homologous recombination using a plasmid that has been constructed to contiguously contain 5' and 3' regions flanking the gene. The contiguous 5' and 3' regions may be introduced into a bacterial cell, for example, on a temperature-sensitive plasmid, such as pE194, in association with a selectable marker at a permissive temperature to allow the plasmid to become established in the cell. The cell is then shifted to a non-permissive temperature to select for cells that have the plasmid integrated into the chromosome at one of the homologous flanking regions. Selection for integration of the plasmid is effected by selection for the selectable marker. After integration, a recombination event at the second homologous flanking region is stimulated by shifting the cells to the permissive temperature for several generations without selection. The cells are plated to obtain single colonies and the colonies are examined for loss of the selectable marker (see, for example, Perego, 1993, in A. L. Sonneshein, J. A. Hoch, and R. Loslck, editors, *Bacillus subtilis and Other Gram-Positive Bacteria*, Chapter 42, American Society of Microbiology, Washington, D.C.).

Inactivation of a restriction endonuclease gene of the present invention may also be accomplished by introducing, substituting, or removing one or more nucleotides in the gene or a regulatory element required for the transcription or translation thereof. For example, nucleotides may be inserted or removed so as to result in the introduction of a stop codon, the removal of the start codon, or a frame-shift of the open reading frame. Such a modification may be accomplished by site-directed mutagenesis or PCR generated mutagenesis in accordance with methods known in the art. See, for example, Botstein and Shortie, 1985, Science 229: 1193-1201; Lo et al., 1984, *Proceedings of the National Academy of Sciences USA* 81: 2285-2289; Higuchi et al., 1988, *Nucleic Acids Research* 16: 7351-7367; Shimada, 1996, *Meth. Mol. Biol.* 57: 157-165; Ho et al., 1989, *Gene* 77: 51-59; Horton et al., 1989, *Gene* 77: 61-68; and Sarkar and Sommer, 1990, *Bio-Techniques* 8: 404-407.

Inactivation of a restriction endonuclease gene of the present invention may also be accomplished by gene disruption techniques by inserting into the gene an integrative plasmid containing a nucleic acid fragment homologous to the gene, which will create a duplication of the region of homology and incorporate vector DNA between the duplicated regions. Such gene disruption can eliminate gene expression if the inserted vector separates the promoter of the gene from the coding region or interrupts the coding sequence such that a non-functional gene product results. A disrupting construct may be simply a selectable marker gene accompanied by 5' and 3' regions homologous to the gene. The selectable marker enables identification of transformants containing the disrupted gene.

Inactivation of a restriction endonuclease gene of the present invention may also be accomplished by the process of gene conversion (see, for example, Iglesias and Trautner, 1983, *Molecular General Genetics* 189: 73-76). For example, in the gene conversion method, a nucleotide sequence corresponding to the gene is mutagenized in vitro to produce a defective nucleotide sequence that is then transformed into the parent bacterial cell to produce a defective gene. By homologous recombination, the defective nucleotide sequence replaces the gene. It may be desirable that the defective gene or gene fragment also encodes a marker that may be used for selection of transformants containing the defective gene. For example, the defective gene may be introduced on a non-replicating or temperature-sensitive plasmid in association with a selectable marker. Selection for integration of the plasmid is effected by selection for the marker under conditions not permitting plasmid replication. Selection for a second recombination event leading to gene replacement is effected by examination of colonies for loss of the selectable marker and acquisition of the mutated gene (see, for example, Perego, 1993, supra). Alternatively, the defective nucleotide sequence may contain an insertion, substitution, or deletion of one or more nucleotides of the gene, as described below.

Inactivation of a restriction endonuclease gene of the present invention may also be accomplished by established anti-sense techniques using a nucleotide sequence complementary to the nucleotide sequence of the gene (Parish and Stoker, 1997, *FEMS Microbiology Letters* 154: 151-157). More specifically, expression of the gene by a bacterial cell may be reduced or eliminated by introducing a nucleotide sequence complementary to the nucleotide sequence of the gene, which may be transcribed in the cell and is capable of hybridizing to the mRNA produced in the cell. Under conditions allowing the complementary anti-sense nucleotide sequence to hybridize to the mRNA, the amount of protein translated is thus reduced or eliminated. Inactivation may also be accomplished by RNA interference techniques (see, for example, U.S. Pat. No. 6,506,559).

Inactivation of a restriction endonuclease gene of the present invention may be further accomplished by random or specific mutagenesis using methods well known in the art, including, but not limited to, chemical mutagenesis (see, for example, Hopwood, *The Isolation of Mutants in Methods in Microbiology* (J. R. Norris and D. W. Ribbons, eds.) pp 363-433, Academic Press, New York, 1970) and transposition (see, for example, Youngman et al., 1983, *Proc. Natl. Acad. Sci. USA* 80: 2305-2309). Modification of the gene may be performed by subjecting the parent cell to mutagenesis and screening for mutant cells in which expression of the gene has been reduced or eliminated. The mutagenesis, which may be specific or random, may be performed, for example, by use of a suitable physical or chemical mutagenizing agent, use of a suitable oligonucleotide, or subjecting the DNA sequence to PCR generated mutagenesis. Furthermore, the mutagenesis may be performed by use of any combination of these mutagenizing methods.

Examples of a physical or chemical mutagenizing agent suitable for the present purpose include ultraviolet (UV) irradiation, hydroxylamine, N-methyl-N'-nitro-N-nitrosoguanidine (MNNG), N-methyl-N'-nitrosoguanidine (NTG) O-methyl hydroxylamine, nitrous acid, ethyl methane sulphonate (EMS), sodium bisulphite, formic acid, and nucleotide analogues. When such agents are used, the mutagenesis is typically performed by incubating the parent cell to be mutagenized in the presence of the mutagenizing agent of choice under suitable conditions, and selecting for mutant cells exhibiting reduced or no expression of the gene.

In a preferred aspect, the inactivation of a restriction endonuclease gene in the bacterial host cell is unmarked with a selectable marker.

Removal of the selectable marker gene may be obtained by culturing the mutants on a counter-selection medium. Where the selectable marker gene contains repeats flanking its 5' and 3' ends, the repeats will facilitate the looping out of the selectable marker gene by homologous recombination when the mutant cell is submitted to counter-selection. The selectable marker gene may also be removed by homologous recombination by introducing into the mutant cell a nucleic acid fragment comprising 5' and 3' regions of the defective gene, but lacking the selectable marker gene, followed by selecting on the counter-selection medium. By homologous recombination, the defective gene containing the selectable marker gene is replaced with the nucleic acid fragment lacking the selectable marker gene. Other methods known in the art may also be used.

Nucleic Acid Constructs

A polynucleotide encoding a polypeptide of interest, e.g., a polypeptide having biological activity, or a DNA methyltransferase or a restriction endonuclease of the present invention, can be manipulated in a variety of ways to provide for expression of the polynucleotide in a suitable bacterial host cell, for example, to enable the methylation of a DNA of interest or for production and recovery of the DNA methyltransferase so it can be used in in vitro methylation. Manipulation of the polynucleotide's nucleotide sequence prior to its insertion into a nucleic acid construct or vector may be desirable or necessary depending on the nucleic acid construct or vector or bacterial host cell. The techniques for modifying nucleotide sequences utilizing cloning methods are well known in the art.

A nucleic acid construct comprising a polynucleotide encoding a polypeptide of interest may be operably linked to one or more control sequences capable of directing the expression of the coding sequence in a bacterial host cell under conditions compatible with the control sequences.

Each control sequence may be native or foreign to the nucleotide sequence encoding a polypeptide of interest. Such control sequences include, but are not limited to, a leader, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence.

The control sequence may be an appropriate promoter sequence, a nucleotide sequence that is recognized by a bacterial host cell for expression of the nucleotide sequence. The promoter sequence contains transcription control sequences that mediate the expression of the polypeptide of interest. The promoter may be any nucleotide sequence that shows transcriptional activity in the bacterial host cell of choice and may be obtained from genes directing synthesis of extracellular or intracellular polypeptides having biological activity either homologous or heterologous to the bacterial host cell.

Examples of suitable promoters for directing the transcription of the nucleic acid constructs of the present invention in a bacterial cell are the promoters obtained from the *E. coli lac* operon, the *Streptomyces coelicolor* agarase gene (dagA), the *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus licheniformis* penicillinase gene (penP), the *Bacillus subtilis* xylA and xylB genes, and the prokaryotic beta-lactamase gene (Villa-Komaroff et al., 1978, *Proceedings of the National Academy of Sciences USA* 75:3727-3731), as well as the tac promoter (DeBoer et al., 1983, *Proceedings of the National Academy of Sciences USA* 80:21-25). Further promoters are described in "Useful proteins from recombinant bacteria" in *Scientific American,* 1980, 242:74-94; and in J. Sambrook, E. F. Fritsch, and T. Maniatis, 1989, *Molecular Cloning, A Laboratory Manual,* 2d edition, Cold Spring Harbor, N.Y.).

The control sequence may also be a suitable transcription terminator sequence, a sequence recognized by a bacterial cell to terminate transcription. The terminator sequence is operably linked to the 3' terminus of the nucleotide sequence encoding a DNA methyltransferase. Any terminator that is functional in the bacterial host cell of choice may be used in the present invention.

The control sequence may also be a suitable leader sequence, a nontranslated region of a mRNA that is important for translation by the bacterial cell. The leader sequence is operably linked to the 5' terminus of the nucleotide sequence directing synthesis of the polypeptide having biological activity. Any leader sequence that is functional in the bacterial host cell of choice may be used in the present invention.

The control sequence may also be a signal peptide coding region, which codes for an amino acid sequence linked to the amino terminus of a polypeptide that can direct the expressed polypeptide into the cell's secretory pathway. The signal peptide coding region may be native to the polypeptide or may be obtained from foreign sources. The 5' end of the coding sequence of the nucleotide sequence may inherently contain a signal peptide coding region naturally linked in translation reading frame with the segment of the coding region that encodes the secreted polypeptide. Alternatively, the 5' end of the coding sequence may contain a signal peptide coding region that is foreign to that portion of the coding sequence and encodes the secreted polypeptide. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide relative to the natural signal peptide coding region normally associated with the coding sequence. The signal peptide coding region may be obtained from an amylase or a protease gene from a *Bacillus* species. However, any signal peptide coding region capable of directing the expressed polypeptide into the secretory pathway of a bacterial host cell of choice may be used in the present invention.

An effective signal peptide coding region for bacterial cells, e.g., *Bacillus* cells, is the signal peptide coding region obtained from the maltogenic amylase gene from *Bacillus* NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), and the *Bacillus subtilis* prsA gene. Further signal peptides are described by Simonen and Palva, 1993, *Microbiological Reviews* 57:109-137.

The control sequence may also be a mRNA stabilizing sequence. The term "mRNA stabilizing sequence" is defined herein as a sequence located downstream of a promoter region and upstream of a coding sequence of a polynucleotide to which the promoter region is operably linked such that all mRNAs synthesized from the promoter region may be processed to generate mRNA transcripts with a stabilizer sequence at the 5' end of the transcripts. The presence of such a stabilizer sequence at the 5' end of the mRNA transcripts increases their half-life (Agaisse and Lereclus, 1994, supra, Hue et al., 1995, *Journal of Bacteriology* 177: 3465-3471). The mRNA processing/stabilizing sequence is complementary to the 3' extremity of bacterial 16S ribosomal RNA. In a preferred aspect, the mRNA processing/stabilizing sequence generates essentially single-size transcripts with a stabilizing sequence at the 5' end of the transcripts. The mRNA processing/stabilizing sequence is preferably one, which is complementary to the 3' extremity of a bacterial 16S ribosomal RNA. See, U.S. Pat. Nos. 6,255,076 and 5,955,310.

An effective mRNA processing/stabilizing sequence for bacterial cells is the *Bacillus thuringiensis* cryIIIA mRNA processing/stabilizing sequence disclosed in WO 94/25612, or portions thereof, which retain the mRNA processing/stabilizing function, or the *Bacillus subtilis* SP82 mRNA processing/stabilizing sequence disclosed in Hue et al., 1995, *Journal of Bacteriology* 177: 3465-3471, or portions thereof, which retain the mRNA processing/stabilizing function.

The nucleic acid construct can then be introduced into a bacterial host cell using methods known in the art or those methods described herein for expressing the polypeptide of interest.

Recombinant Expression Vectors

In the methods of the present invention, a recombinant expression vector comprising a polynucleotide encoding a polypeptide of interest, e.g., a polypeptide having biological activity, or a DNA methyltransferase or a restriction endonuclease of the present invention, a promoter, and transcriptional and translational stop signals may be used for the recombinant production of the polypeptide. The various nucleic acid and control sequences described above may be joined together to produce a recombinant expression vector that may include one or more convenient restriction sites to allow for insertion or substitution of the nucleotide sequence directing synthesis of a polypeptide of interest at such sites. Alternatively, the nucleotide sequence may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector that can be conveniently subjected to recombinant DNA procedures and can bring about the expression of the nucleotide sequence. The choice of the vector will typically depend on the compatibility of the vector with the bacterial cell into which the vector is to be introduced. The vectors may be linear or closed circular plasmids. The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the bacterial cell, is integrated into the genome and replicated together with the chromosome(s) into which it has been integrated. The vector system may be a single vector or plasmid or two or more vectors or plasmids that together contain the total DNA to be introduced into the genome of the *Bacillus* cell, or a transposon.

The vectors may be integrated into the bacterial cell genome when introduced into a bacterial cell. For integration into the host cell genome, the vector may rely on the polynucleotide's sequence encoding the polypeptide of interest or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the bacterial cell in question. Examples of bacterial origins of replication are the origins of replication of plasmids pBR322, pUC19, pACYC177, and pACYC184 permitting replication in *E. coil*, and pUB110, pE194, pTA1060, and pAMβ1 permitting replication in *Bacillus*. The origin of replication may be one having a mutation to make its function temperature-sensitive in the bacterial cell (see, e.g., Ehrlich, 1978, *Proceedings of the National Academy of Sciences USA* 75:1433-1436).

More than one copy of a nucleotide sequence directing synthesis of a polypeptide of interest may be introduced into the bacterial cell to amplify expression of the nucleotide sequence. Stable amplification of the nucleotide sequence can be obtained by integrating at least one additional copy of the sequence into the bacterial cell genome using methods well known in the art and selecting for transformants. A convenient method for achieving amplification of genomic DNA sequences is described in WO 94/14968.

The vectors preferably contain one or more selectable markers that permit easy selection of transformed cells. A selectable marker is a gene the product of which provides for biocide resistance, resistance to heavy metals, prototrophy to auxotrophs, and the like. Examples of bacterial selectable markers are the dal genes from *Bacillus subtilis* or *Bacillus licheniformis*, or markers that confer antibiotic resistance such as ampicillin, kanamycin, erythromycin, chloramphenicol or tetracycline resistance. Furthermore, selection may be accomplished by co-transformation, e.g., as described in WO 91/09129, where the selectable marker is on a separate vector.

The procedures used to ligate the elements described above to construct the recombinant expression vectors are well known to one skilled in the art (see, e.g., Sambrook et al., 1989, supra).

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et at, 1988, *Nucleic Acids Res.* 16: 6127-6145). The introduction of DNA into a *Streptomyces* cell may, for instance, be effected by protoplast transformation and electroporation (see, e.g.,Gong et al., 2004, *Folia Microbial.* (*Praha*) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98:6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-207, by electroporation (see, e.g., Buckley et al., 1999, *Appl. Environ. Microbial.* 65: 3800-3804) or by conjugation (see, e.g., Clewell, 1981, *Microbial. Rev.* 45: 409-436). However, any method known in the for introducing DNA into a host cell can be used.

Bacterial Host Cells

The present invention also relates to bacterial host cells comprising a nucleic acid construct or recombinant expression vector comprising a polynucleotide encoding a polypeptide of interest, e.g., a polypeptide having biological activity, or a restriction endonuclease or DNA methyltransferase of the present invention.

The present invention also relates to bacterial host cells comprising a polynucleotide encoding a restriction endonuclease, which is inactivated;

wherein the polynucleotide encoding the restriction endonuclease is selected from the group consisting of (a) a polynucleotide encoding a polypeptide comprising an amino acid sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% sequence Identity with amino acids 1 to 337 of SEQ ID NO: 4; (b) a polynucleotide comprising a nucleotide sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% sequence identity with nucleotides 1 to 1011 of SEQ ID NO: 3; and (c) a polynucleotide that hybridizes under preferably at least medium stringency conditions, more preferably at least medium-high stringency conditions, and most preferably at least high stringency conditions with nucleotides 1 to 1011 of SEQ ID NO: 3 or its full-length complementary strand;

wherein the restriction endonuclease has the same specificity as the restriction endonuclease of amino acids 1 to 337 of SEQ ID NO: 4; and wherein the inactivation of the polynucleotide encoding the restriction endonuclease prevents DNA that is introduced into the bacterial host cell from being digested by the restriction endonuclease and avoids the need to methylate the DNA with a DNA methyltransferase prior to being introduced into the host cell.

The present invention also relates to bacterial host cells comprising a nucleic acid construct or recombinant expression vector comprising a DNA encoding or involved in the expression of a polypeptide having biological activity, wherein the bacterial host cells comprising the DNA is obtained by one of the methods described herein for introducing the DNA into such host cells.

The bacterial host cell may be any Gram positive bacterium or a Gram negative bacterium that comprises a restriction-modification system, as described herein. Gram positive bacteria include, but not limited to, *Bacillus, Streptococcus, Streptomyces, Staphylococcus, Enterococcus, Lactobacillus, Lactococcus, Clostridium, Geobacillus,* and *Oceanobacillus.* Gram negative bacteria include, but not limited to, *E. coil, Pseudomonas, Salmonella, Campylobacter, Helicobacter, Flavobacterium, Fusobacterium, Ilyobacter, Neisseria,* and *Ureaplasma.*

In the methods of the present invention, the bacterial host cell may be any *Bacillus* cell. *Bacillus* cells useful in the practice of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

In a preferred aspect, the bacterial host cell is a *Bacillus amyloliquefaciens, Bacillus lentus, Bacillus licheniformis, Bacillus stearothermophilus* or *Bacillus subtilis* cell. In a more preferred aspect, the bacterial host cell is a *Bacillus amyloliquefaciens* cell. In another more preferred aspect, the bacterial host cell is a *Bacillus clausli* cell. In another more preferred aspect, the bacterial host cell is a *Bacillus licheniformis* cell. In another more preferred aspect, the bacterial host cell is a *Bacillus subtilis* cell.

In the methods of the present invention, the bacterial host cell may be any *Streptococcus* cell. *Streptococcus* cells useful in the practice of the present invention include, but are not limited to, *Streptococcus equisimilis, Streptococcus pyogenes, Streptococcus uberis,* and *Streptococcus equi* subsp. *Zooepidemicus.*

In a preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

In the methods of the present invention, the bacterial host cell may be any *Streptomyces* cell. *Streptomyces* cells useful in the practice of the present invention include, but are not limited to, *Streptomyces achromogenes, Streptomyces avermitilis, Streptomyces coelicolor, Streptomyces griseus,* and *Streptomyces lividans.*

In a preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

In the methods of the present invention involving methylation of a DNA of interest with a DNA methyltransferase, the bacterial cell used for the methylation will likely be different from the final host bacterial cell. The bacterial cell used for the methylation can be a bacterial cell into which a DNA methyltransferase gene of the present invention, foreign to the cell, has been introduced or a bacterial cell in which a DNA methyltransferase gene is native to the cell.

In a further aspect of the present invention, the bacterial host cell may additionally contain modifications, e.g., deletions or disruptions, of other genes that may be detrimental to the production, recovery or application of a polypeptide of interest. In a preferred aspect, a bacterial host cell is a protease-deficient cell. In a more preferred aspect, the bacterial host cell, e.g., *Bacillus* cell, comprises a disruption or deletion of aprE and nprE. In another preferred aspect, the bacterial host cell does not produce spores. In another more preferred aspect, the bacterial host cell, e.g., *Bacillus* cell, comprises a disruption or deletion of spoIIAC. In another preferred aspect, the bacterial host cell, e.g., *Bacillus* cell, comprises a disruption or deletion of one of the genes involved in the biosynthesis of surfactin, e.g., srfA, srfB, srfC, and srfD. See, for example, U.S. Pat. No. 5,958,728. Other genes, e.g., the amyE gene, which are detrimental to the production, recovery or application of a polypeptide of interest may also be disrupted or deleted.

DNA

In the methods of the present invention, the DNA introduced into a bacterial host cell can be any DNA of interest. The DNA may be native or heterologous (foreign) to the bacterial host cell of interest.

The DNA can encode any polypeptide having a biological activity of interest. The polypeptide may be native or heterologous (foreign) to the bacterial host cell of interest. The term "heterologous polypeptide" is defined herein as a polypeptide that is not native to the host cell; a native polypeptide in which structural modifications, e.g., deletions, substitutions, and/or insertions, have been made to alter the native polypeptide; or a native polypeptide whose expression is quantitatively altered as a result of manipulation of the DNA encoding the polypeptide by recombinant DNA techniques, e.g., a stronger promoter. The polypeptide may be a naturally occurring allelic and engineered variations of the below-mentioned polypeptides and hybrid polypeptides.

The term "polypeptide" is not meant herein to refer to a specific length of the encoded product and, therefore, encompasses peptides, oligopeptides, and proteins. The term "polypeptide" also encompasses hybrid polypeptides, which comprise a combination of partial or complete polypeptide sequences obtained from at least two different polypeptides wherein one or more may be heterologous to the fungal cell. Polypeptides further include naturally occurring allelic and engineered variations of a polypeptide.

In a preferred aspect, the polypeptide is an antibody, antigen, antimicrobial peptide, enzyme, growth factor, hormone, immunodilator, neurotransmitter, receptor, reporter protein, structural protein, and transcription factor.

In a more preferred aspect, the polypeptide is an oxidoreductase, transferase, hydrolase, lyase, isomerase, or ligase. In a most preferred aspect, the polypeptide is an alpha-glucosidase, aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, glucocerebrosidase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, urokinase, or xylanase.

In another preferred aspect, the polypeptide is an albumin, collagen, tropoelastin, elastin, or gelatin.

In another preferred aspect, the polypeptide is a hybrid polypeptide, which comprises a combination of partial or complete polypeptide sequences obtained from at least two different polypeptides wherein one or more may be heterologous to the bacterial host cell.

In another preferred aspect, the polypeptide is a fused polypeptide in which another polypeptide is fused at the N-terminus or the C-terminus of the polypeptide or fragment thereof. A fused polypeptide is produced by fusing a nucleotide sequence (or a portion thereof) encoding one polypeptide to a nucleotide sequence (or a portion thereof) encoding another polypeptide. Techniques for producing fusion polypeptides are known in the art, and include, ligating the coding sequences encoding the polypeptides so that they are in frame and expression of the fused polypeptide is under control of the same promoter(s) and terminator.

The DNA encoding a polypeptide of interest may be obtained from any prokaryotic, eukaryotic, or other source. For purposes of the present invention, the term "obtained from" as used herein in connection with a given source shall mean that the polypeptide is produced by the source or by a cell in which a gene from the source has been inserted. The techniques used to isolate or clone a DNA encoding a polypeptide of interest are known in the art and include isolation from genomic DNA, preparation from cDNA, or a combination thereof. The cloning of the DNA of interest from such genomic DNA can be effected, e.g., by using the well known polymerase chain reaction (PCR). See, for example, Innis et al., 1990, *PCR Protocols: A Guide to Methods and Application*, Academic Press, New York. The cloning procedures may involve excision and isolation of a desired nucleic acid fragment comprising the nucleic acid sequence encoding the polypeptide, insertion of the fragment into a vector molecule, and incorporation of the recombinant vector into the mutant fungal cell where multiple copies or clones of the nucleic acid sequence will be replicated. The DNA may be of genomic, cDNA, RNA, semisynthetic, synthetic origin, or any combinations thereof.

A DNA encoding a polypeptide of interest may be manipulated in a variety of ways to provide for expression of the DNA in a suitable bacterial host cell. The construction of nucleic acid constructs and recombinant expression vectors for the DNA encoding a polypeptide of interest can be carried out as described herein for the expression of a DNA methyltransferase of the present invention.

The DNA can also be a control sequence, e.g., promoter, for manipulating the expression of a gene of interest. Non-limiting examples of control sequences are described herein.

The DNA can further be a nucleic acid construct for inactivating a gene of interest in a bacterial cell.

The DNA is not to be limited in scope by the specific examples disclosed above, since these examples are intended as illustrations of several aspects of the invention.

Methods of Production

The present invention also relates to methods of producing a polypeptide having biological activity, comprising:

(a) cultivating a bacterial host cell comprising an introduced DNA encoding or involved in the expression of the polypeptide having biological activity under conditions conducive for production of the polypeptide;

wherein the DNA is methylated prior to being introduced into the bacterial host cell by a DNA methyltransferase selected from the group consisting of (i) a polypeptide comprising an amino acid sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% sequence identity with amino acids 1 to 381 of SEQ ID NO: 2; (ii) a polypeptide encoded by a polynucleotide comprising a nucleotide sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% sequence identity with nucleotides 1 to 1143 of SEQ ID NO: 1; (iii) a polypeptide encoded by a polynucleotide that hybridizes under preferably at least medium stringency conditions, more preferably at least medium-high stringency conditions, and most preferably at least high stringency conditions with nucleotides 1 to 1143 of SEQ ID NO: 1 or its full-length complementary strand; and (iv) a variant comprising a substitution, deletion, and/or insertion of one or more amino acids of amino acids 1 to 381 of SEQ ID NO: 2;

wherein the DNA methyltransferase has the same specificity as the DNA methyltransferase of amino acids 1 to 381 of SEQ ID NO: 2 and is native to the bacterial host cell; and wherein the methylation prevents the introduced DNA from being digested by a restriction endonuclease of the bacterial host cell; and (b) recovering the polypeptide having biological activity.

The present invention also relates to methods of producing a polypeptide having biological activity, comprising:

(a) cultivating a bacterial host cell comprising an introduced DNA encoding or involved in the expression of the polypeptide having biological activity under conditions conducive for production of the polypeptide;

wherein the bacterial host cell comprises a polynucleotide encoding a restriction endonuclease, which is inactivated;

wherein the polynucleotide encoding the restriction endonuclease is selected from the group consisting of (i) a polynucleotide encoding a polypeptide comprising an amino acid sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% sequence identity with amino acids 1 to 337 of SEQ ID NO: 4; (i) a polynucleotide comprising a nucleotide sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% sequence identity with nucleotides 1 to 1011 of SEQ ID NO: 3; and (iii) a polynucleotide that hybridizes under preferably at least medium stringency conditions, more preferably at least medium-high stringency conditions, and most preferably at least high stringency conditions with nucleotides 1 to 1011 of SEQ ID NO: 3 or its full-length complementary strand;

wherein the restriction endonuclease has the same specificity as the restriction endonuclease of amino acids 1 to 337 of SEQ ID NO: 4; and wherein the inactivation of the polynucleotide encoding the restriction endonuclease prevents the introduced DNA from being digested by the restriction endonuclease and avoids the need to methylate the DNA with a DNA methyltransferase prior to introducing the DNA into the bacterial host cell; and (b) recovering the polypeptide having biological activity.

The present invention also relates to methods of producing a polypeptide having restriction endonuclease activity, comprising: (a) cultivating a bacterial host cell comprising a polynucleotide encoding a polypeptide having restriction endonuclease activity of the present invention under conditions conducive for production of the polypeptide; and (b) recovering the polypeptide having restriction endonuclease activity.

The present invention also relates to methods of producing a polypeptide having DNA methyltransferase activity, comprising: (a) cultivating a bacterial host cell comprising a polynucleotide encoding a polypeptide having DNA methyltransferase activity of the present invention under conditions conducive for production of the polypeptide; and (b) recovering the polypeptide having DNA methyltransferase activity.

The bacterial host cells are cultivated in a nutrient medium suitable for production of a polypeptide of interest using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide of interest to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). The secreted polypeptide of interest can be recovered directly from the medium.

The polypeptide of interest may be detected using methods known in the art that are specific for the polypeptide. These detection methods may include use of specific antibodies, high performance liquid chromatography, capillary chromatography, formation of an enzyme product, disappearance of an enzyme substrate, or SDS-PAGE.

For example, an enzyme assay may be used to determine the activity of the enzyme. Procedures for determining enzyme activity are known in the art for many enzymes (see, for example, D. Schomburg and M. Salzmann (eds.), *Enzyme Handbook*, Springer-Verlag, New York, 1990). Assays for determining activity of a restriction endonuclease or DNA methyltransferase of the present invention are described herein.

The resulting polypeptide may be isolated by methods known in the art. For example, a polypeptide of interest may be isolated from the cultivation medium by conventional procedures including, but not limited to, centrifugation, filtration, extraction, spray-drying, evaporation, or precipitation. The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., *Protein Purification*, J.-C. Janson and Lars Ryden, editors, VCH Publishers, New York, 1989).

Inactivation of Genes

The present invention also relates to methods of producing a mutant of a parent bacterial cell, which comprises (a) introducing into a parent bacterial cell a DNA comprising a nucleic acid construct to inactivate a gene encoding a polypeptide in the parent bacterial cell, which results in a mutant cell producing less of the polypeptide than the parent cell when cultivated under the same conditions; wherein the bacterial host cell comprises a polynucleotide encoding a restriction endonuclease, which is inactivated, and the polynucleotide encoding the restriction endonuclease is selected from the group consisting of (i) a polynucleotide encoding a polypeptide comprising an amino acid sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% sequence identity with amino acids 1 to 337 of SEQ ID NO: 4; (ii) a polynucleotide comprising a nucleotide sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% sequence identity with nucleotides 1 to 1011 of SEQ ID NO: 3; (iii) a polynucleotide that hybridizes under preferably at least medium stringency conditions, more preferably at least medium-high stringency conditions, and most preferably at least high stringency conditions with nucleotides 1 to 1011 of SEQ ID NO: 3 or its full-length complementary strand; and (iv) a polynucleotide encoding a variant comprising a substitution, deletion, and/or insertion of one or more amino acids of amino acids 1 to 337 of SEQ ID NO: 4; wherein the restriction endonuclease has the same specificity as the restriction endonuclease of amino acids 1 to 337 of SEQ ID NO: 4, and wherein the inactivation of the polynucleotide encoding the restriction endonuclease prevents the introduced DNA from being digested by the restriction endonuclease and avoids the need to methylate the DNA with a DNA methyltransferase prior to introducing the DNA into the parent bacterial cell; and (b) isolating the mutant cell.

The present invention also relates to methods of producing a mutant of a parent bacterial cell, which comprises (a) introducing into a parent bacterial cell a DNA comprising a nucleic acid construct to inactivate a gene encoding a polypeptide in the parent bacterial cell, which results in a mutant cell producing less of the polypeptide than the parent cell when cultivated under the same conditions; wherein the DNA is methylated prior to being introduced into the bacterial host cell by a DNA methyltransferase selected from the group consisting of (i) a polypeptide comprising an amino acid sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%% sequence identity with amino acids 1 to 381 of SEQ ID NO: 2; (ii) a polypeptide encoded by a polynucleotide comprising a nucleotide sequence having preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% sequence identity with nucleotides 1 to 1143 of SEQ ID NO: 1; (iii) a polypeptide encoded by a polynucleotide that hybridizes under preferably at least medium stringency conditions, more preferably at least medium-high stringency conditions, and most preferably at least high stringency conditions with nucleotides 1 to 1143 of SEQ ID NO: 1 or its full-length complementary strand; and (iv) a variant comprising a substitution, deletion, and/or insertion of one or more amino acids of amino acids 1 to 381 of SEQ ID NO: 2; wherein the DNA methyltransferase has the same specificity as the DNA methyltransferase of amino acids 1 to 381 of SEQ ID NO: 2; and wherein the methylation prevents the introduced DNA from being digested by a restriction endonuclease of the parent bacterial cell; and (b) isolating the mutant cell.

The mutant cell comprising an inactivated gene may be constructed using the methods described here.

The bacterial mutant cells so created are particularly useful as host cells for the expression of polypeptides native or foreign to the cells. Therefore, the present invention further relates to methods of producing a native or foreign polypeptide comprising: (a) cultivating the mutant cell under conditions conducive for production of the polypeptide; and (b) recovering the polypeptide. The term "foreign polypeptide" is defined herein as a polypeptide that is not native to the host cell, a native protein in which modifications have been made to alter the native sequence, or a native protein whose expression is quantitatively altered as a result of a manipulation of the host cell by recombinant DNA techniques.

Examples of polypeptides that can be expressed in such mutants are described herein.

The methods used for cultivation and purification of the product of interest may be performed by methods known in the art and described herein.

The present invention is further described by the following examples that should not be construed as limiting the scope of the invention.

EXAMPLES

DNA Sequencing

DNA sequencing was performed using an Applied Biosystems Model 3130X Genetic Analyzer (Applied Biosystems, Foster City, Calif., USA) employing dye terminator chemistry (Giesecke et al., 1992, *Journal of Virol. Methods* 38: 47-60). Sequences were assembled using phred/phrap/consed (University of Washington, Seattle, Wash., USA) with sequence specific primers.

Strains

*Bacillus* plasmids were constructed in *Bacillus subtilis* 168Δ4. *Bacillus subtilis* 168Δ4 is derived from the *Bacillus subtilis* type strain 168 (BGSC 1A1, *Bacillus* Genetic Stock Center, Columbus, Ohio) and has deletions in the spoIIAC, aprE, nprE, and amyE genes. The deletion of these four genes was performed essentially as described for *Bacillus subtilis* A164Δ5, which is described in detail in U.S. Pat. No. 5,891,701.

Media

LB medium was composed per liter of 10 g of tryptone, 5 g of yeast extract, and 5 g of NaCl.

LB plates were composed of LB medium and 15 g of bacto agar per liter.

LB ampicillin medium was composed of LB medium and 100 μg of ampicillin per ml (filter sterilized, added after autoclaving).

LB ampicillin plates were composed of LB ampicillin medium and 15 g of bacto agar per liter.

VY medium was composed per liter of 25 g of veal infusion (BD Diagnostics, Franklin Lakes, N.J., USA) and 5 g of yeast extract.

2×YT medium was composed per liter of 16 g of Tryptone, 10 g of yeast extract, and 5 g of NaCl.

2×YT ampicillin medium was composed of 2×YT medium and 100 μg of ampicillin per ml (filter sterilized, added after autoclaving).

2×YT ampicillin plates were composed per liter of 2×YT ampicillin medium and 15 g of bacto agar.

LBS medium was composed of LB medium and 0.5 M sorbitol.

LBSM medium was composed of LBS medium and 0.38 M mannitol.

TBAB medium was composed of Difco Tryptose Blood Agar Base (BD Diagnostics, Franklin Lakes, N.J., USA).

TBAB chloramphenicol plates were composed of TBAB medium and 5 µg of chloramphenicol per ml.

TBAB neomycin plates were composed of TBAB medium and 6 µg of neomycin per ml.

TBAB erythromycin/lincomycin plates were composed of TBAB medium and 1 µg of erythromycin and 25 µg of lincomycin per ml.

TY medium was composed per liter of 20 g tryptone, 5 g yeast extract, 6 mg $FeCl_2.4H_2O$, 1 mg $MnCl_2.4H_2O$, and 15 mg $MgSO_4.7H_2O$.

TY plates were composed of TY medium and 20 g of bacto agar per liter.

TY chloramphenicol plates were composed of TY plate medium containing 6 µg chloramphenicol per ml.

LBPG plates were composed of LB plate medium containing 0.01 M $K_3PO_4$ and 0.4% glucose.

Example 1

Determination of the Genome Sequence for *Bacillus licheniformis* Strain SJ1904

The genome sequence for the entire chromosome of *Bacillus licheniformis* strain SJ1904 was determined from contigs generated using 454 DNA sequencing technology (Margulies et al., 2005, *Nature* 437: 376-380), random paired reads using Sanger sequencing technology, and, to close gaps and resolve repeats, reads from PCR fragments of genomic DNA. Sequencing data was assembled using Phrap, and edited and viewed in Consed. Gene models were predicted from the genomic DNA sequence using Glimmer (Delcher et al., 1999, *Nucleic Acids Research* 27: 4636-4641). Gene models were machine annotated by comparison to the nonredundant database PIR-NREF (Wu et al., 2002, *Nucleic Acids Research* 30: 35-37) using a BLASTP with an E-value threshold of $1 \times 10^{-5}$.

Example 2

Identification of *Bacillus licheniformis* M.B11190411 DNA Methyltransferase Gene The deduced amino acid sequences for the *Bacillus licheniformis* strain SJ1904 gene models were compared to the protein sequences from REBASE (Roberts, R. J., Macelis, M., Rebase. 2005) using BLASTP (Altschul et at, 1997, *Nucleic Acids Research* 25: 3389-3402). As the DNA methyltransferases have a moderate level of sequence conservation, this analysis identified all putative DNA methyltransferases in this genome. A cytosine-specific DNA methyltransferase signature was identified within M.Bli1904II using Prints-S version 16 as implemented through interProScan release v3.3. In addition; the six highly conserved motifs found in cytosine-specific DNA methyltransferases (Kumar of al., 1994, *Nucleic Acids Research* 22 1-10) were found to be conserved in the *Bacillus licheniformis* M.Bli1904II DNA methyltransferase.

Example 3

Characterization of the *Bacillus licheniformis* M.Bli1904II DNA Methyltransferase Gene The nucleotide sequence (SEQ ID NO: 1) and deduced amino acid sequence (SEQ ID NO: 2) of the *Bacillus licheniformis* M.Bli1904II DNA methyltransferase gene are shown in FIGS. 1A and 1B. The coding sequence is 1014 bp including the stop codon. The coding region is 36.1% G+C. The encoded predicted protein is 337 amino acids with a molecular mass of 38.5 kDa.

A comparative pairwise global alignment of amino acid sequences was determined using the Needleman-Wunsch algorithm (Needleman and Wunsch, 1970, supra) as implemented in the Needle program of EMBOSS with gap open penalty of 10, gap extension penalty of 0.5, and the EBLOSUM62 matrix. The alignment showed that the deduced amino acid sequence of the *Bacillus licheniformis* M.Bli1904II DNA methyltransferase shared 64% identity with a *Bacillus weihenstephanensis* C-5 cytosine-specific DNA methyltransferase precursor (UniRef100_Q2AVE0) and shared 47% identity with an *Oceanobacillus iheyensis* cytosine-specific DNA methyltransferase (UniRef100_Q8EL98). When the output of Needle labeled "longest identity" was used as the percent identity and was calculated as follows:

(Identical Residues×100)/(Length of Alignment–Number of Gaps in Alignment)

the deduced amino acid sequence of the *Bacillus licheniformis* M.Bli1904II DNA methyltransferase shared 68.5% identity with the *Bacillus weihenstephanensis* C-5 cytosine-specific DNA methyltransferase precursor (UniRef100_Q2AVE0) and 55.9% identity with the *Oceanobacillus iheyensis* cytosine-specific DNA methyltransferase (UniRef100_Q8EL98).

Example 4

Identification of the *Bacillus licheniformis* Bli1904II Type II Restriction Endonuclease Gene Type II restriction endonucleases generally share no sequence identity between one another and share only minor identity when they have similar DNA recognition sites. In addition, a Type II restriction endonuclease is usually located next to its corresponding DNA methyltransferase in a given restriction-modification system. Furthermore, all restriction endonuclease genes characterized to date are larger than 450 bp (Kong, et al., 2000, *Nucleic Acids Research* 28: 3216-3223). Using these criteria, a hypothetical gene greater than 450 bp and located next to a *Bacillus licheniformis* M.Bli1904II DNA methyltransferase gene was identified from the *Bacillus licheniformis* SJ1904 annotated gene models as a Type II restriction endonuclease gene, Bli1904II.

Example 5

Characterization of the *Bacillus licheniformis* Bli1904II Type II Restriction Endonuclease Gene The nucleotide sequence (SEQ ID NO: 3) and deduced amino acid sequence (SEQ ID NO: 4) of the *Bacillus licheniformis* Bli1904II Type II restriction endonuclease gene are shown in FIGS. 2A and 2B. The coding sequence is 1146 bp including the stop codon. The coding region is 36.3% G+C. The encoded predicted protein is 381 amino acids with a molecular mass of 43.7 kDa.

A comparative pairwise global alignment of amino acid sequences was determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The alignment showed that the deduced amino acid sequence of the *Bacillus licheniformis* Bli1904II Type II restriction endonuclease shared 45% identity with a *Bacillus weihenstephanensis* hypothetical protein (UniRef100_Q2AVE3) and 32.6% identity with a *Psychromonas* sp. CNPT3 hypothetical protein (UniRef100_Q1ZE16). When the output of Needle labeled "longest identity" was used as the percent identity and was calculated as follows:

(Identical Residues×100)/(Length of Alignment– Number of Gaps in Alignment)

the deduced amino acid sequence of the *Bacillus licheniformis* M.Bli1904 II DNA methyltransferase shared 47% identity with the *Bacillus weihenstephanensis* hypothetical protein (UniRef100_Q2AVE3) and 47.2% identity with the *Psychromonas* sp. CNPT3 hypothetical protein (UniRef100_Q1ZE16).

Example 6

Cloning of the *Bacillus licheniformis* M.Bli1904II DNA Methyltransferase Gene

The *Bacillus licheniformis* M.Bli1904 II DNA methyltransferase gene was cloned by PCR for expression in *Bacillus subtilis*.

Genomic DNA was isolated from *Bacillus licheniformis* SJ1904 according to the procedure of Pitcher et al., 1989, *Lett. Appl. Microbiol.* 8: 151-156. FIG. 3 shows the region of the *Bacillus licheniformis* chromosome comprising the genes encoding Bli1904II restriction endonuclease and M.Bli1904II DNA methyltransferase. An approximately 1043 bp fragment of the *Bacillus licheniformis* SJ1904 chromosome including the ribosome binding site and coding region of the M.Bli1904II DNA methyltransferase gene, comprising nucleotides 2019-3049 of SEQ ID NO: 5 (FIG. 3), was amplified by PCR from *Bacillus licheniformis* SJ1904 genomic DNA using primers 999611 and 999612 shown below. Primer 999611 incorporates a Sac I restriction site, and primer 999612 incorporates an Mlu I restriction site.

```
Primer 999611:
5'-GAGCTCTGCAAGGAGGTATAATTTTG-3'    (SEQ ID NO: 6)

Primer 999612:
5'-ACGCGTTTATTCAGCTATTGCATATTC-3'   (SEQ ID NO: 7)
```

The PCR was performed using Pfx PLATINUM® DNA Polymerase (Invitrogen, Carlsbad, Calif., USA). The amplification reaction (50 µl) was composed of 1× Pfx Amplification Buffer (Invitrogen, Carlsbad, Calif., USA), 1 mM $MgSO_4$, 300 µM of each dNTP, 0.3 µM of each primer, 1.25 units of PLATINUM® Pfx DNA Polymerase, and approximately 200 ng of template DNA. The reaction was performed using a ROBOCYCLER® 40 Temperature Cycler (Stratagene Corporation, La Jolla, Calif., USA) programmed for 1 cycle at 95° C. for 2 minutes; 30 cycles each at 95° C. for 1 minute, 55° C. for 1 minute, and 68° C. for 1 minute; and 1 cycle at 68° C. for 3 minutes.

The resulting PCR product of approximately 1043 bp was cloned into vector pCR4Blunt using a ZERO BLUNT® TOPO® PCR Cloning Kit for Sequencing (Invitrogen, Carlsbad, Calif., USA) and transformed into ONE SHOT® TOP10 Chemically Competent *E. coli* cells according to the manufacturer's instructions. Plasmid DNA was isolated from one transformant using a Plasmid Midi Kit (QIAGEN Inc., Valencia, Calif., USA) and confirmed by digestions with Eco RI, Nco I, and Sna BI followed by 0.8% agarose electrophoresis in TBE (50 mM Tris base-50 mM boric acid-1 mM disodium EDTA) buffer, which yielded expected fragments of 3939 bp and 1061 bp for Eco RI; 3217 bp and 1783 bp for Nco I; and 4165 bp and 835 bp for Sna BI. The DNA sequence of the cloned PCR fragment was confirmed by DNA sequencing. This plasmid was designated pMDT138 (FIG. 4).

Plasmid pMDT138 was transformed into *E. coli* XL1-Blue cells (Stratagene Corporation, La Jolla, Calif., USA) according to the manufacturer's instructions, selecting for ampicillin resistance on 2×YT ampicillin plates at 37° C. One transformant was designated MDT45 and was deposited on Sep. 7, 2006, under the terms of the Budapest Treaty with the Agricultural Research Service Patent Culture Collection, Northern Regional Research Center, 1815 University Street, Peoria, Ill., 61604, and given accession number NRRL B-41967.

Example 7

Construction of pMDT100

Plasmid pMDT100 is an *E. coli* replicon containing the $P_{amyL4199}/P_{short\ consinsus\ amyQ}/P_{cryIIIA}/$cryIIIAstab triple tandem promoter driving expression of the *Bacillus clausil* alkaline protease gene (aprH). This aprH expression cassette and the cat gene of pC194 (Horinouchi and Weisblum, 1982, *J. Bacteria* 150: 804-814) are flanked on both sides by fragments of the *Bacillus subtilis* alpha-amylase (amyE) gene, permitting insertion of the aprH expression cassette and cat gene at the amyE locus of the *Bacillus subtilis* chromosome by double homologous recombination via the two amyE fragments. Replacement of the aprH gene in pMDT100 with another gene allows chromosomal insertion and expression of that gene in *Bacillus subtilis*. The construction of pMDT100 is described below.

Figure 5:
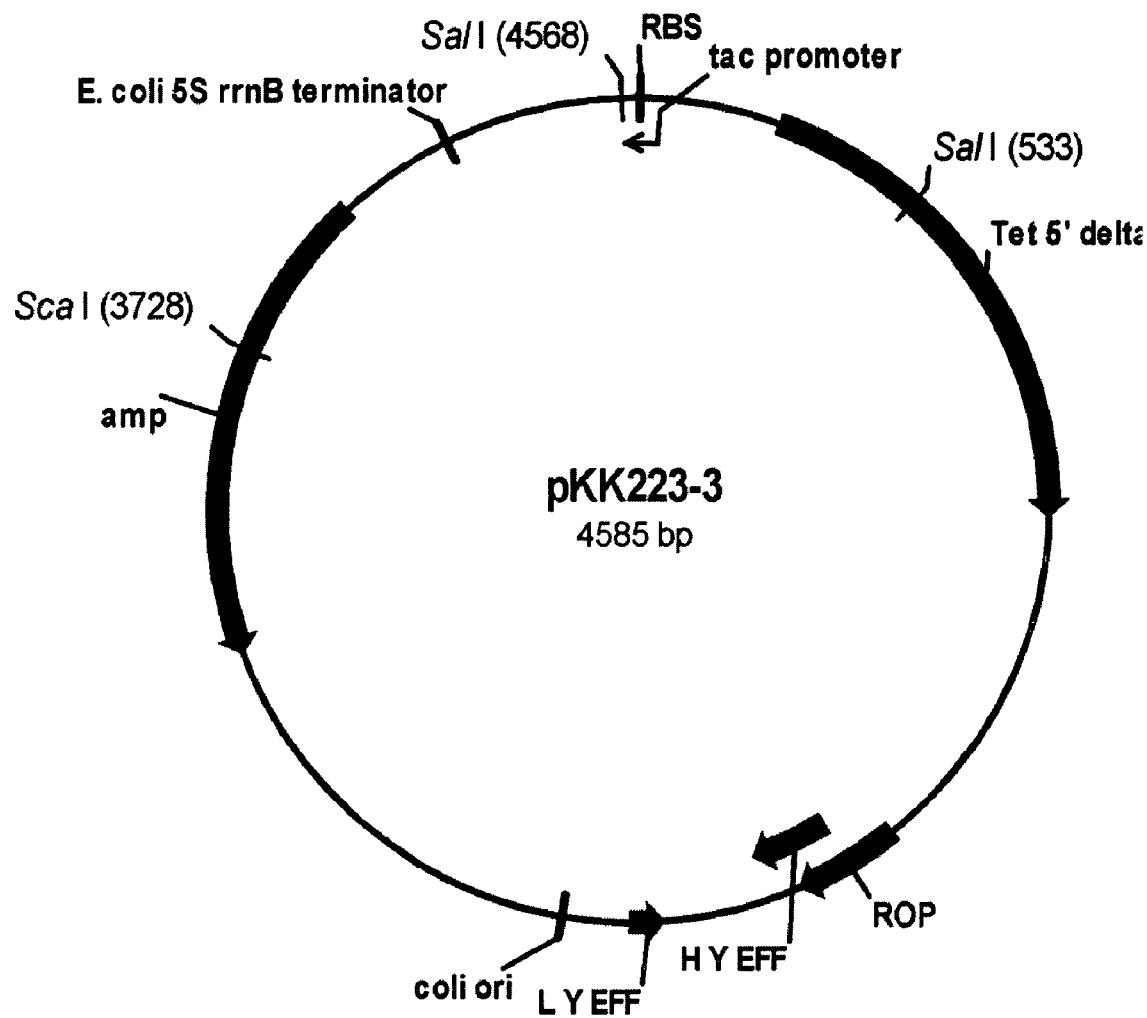
FIG. 5 shows a restriction map of pKK223-3.

Plasmid pNBT51. Plasmid pNBT10 (pDG268MCS-$Pr_{cryIIIA}/$cryIIIAstab/SAV; U.S. Pat. No. 6,255,076) was isolated from *E. coli* host DH5α, using a QIAGEN® Plasmid Kit (QIAGEN Inc., Valencia, Calif., USA) according to the manufacturer's instructions, and digested with Cla I and Sca I. Cleavage occurred at the Cla I site at approximately codon 326 of the aprH coding sequence and not at the Cla I site at approximately codon 23, which was blocked by methylation due to *E. coli* Dam DNA methyltransferase. The Cla I ends were blunted using Klenow fragment (New England Biolabs, Inc., Beverly, Mass., USA) and dNTPs according to the manufacturer's instructions. The digested plasmid was analyzed by 0.8% agarose electrophoresis in TBE buffer, and a vector fragment of approximately 6615 bp was purified using a QIAQUICK® Gel Extraction Kit (QIAGEN Inc., Valencia, Calif., USA). Plasmid pOS4301 (*Bacillus* Genetic Stock Center, Ohio State University, Columbus, Ohio, USA) was digested with Sal I and Sca I, and the Sal I ends were blunted using Klenow fragment and dNTPs, as described above. The digested plasmid was analyzed by 0.8% agarose electrophoresis in TBE buffer, and a fragment of approximately 840 bp bearing the *E. coli* rrnB transcription terminator was purified using a QIAQUICK® Gel Extraction Kit. The same 840 bp Sal I/Sca I fragment could be isolated from the vector pKK223-3 (GE Healthcare, Piscataway, N.J., USA) (FIG. 5). The pNBT10 vector fragment and terminator-bearing fragment were ligated together with T4 DNA ligase (Roche Diagnostics Corporation, Indianapolis, Ind., USA) according to the manufacturer's instructions, and *E. coli* DH5α (Gibco BRL, Gaithersburg, Md., USA) was transformed with the ligation according to the manufacturer's instructions, selecting for ampicillin resistance on 2×YT ampicillin plates at 37°

Figure 6:
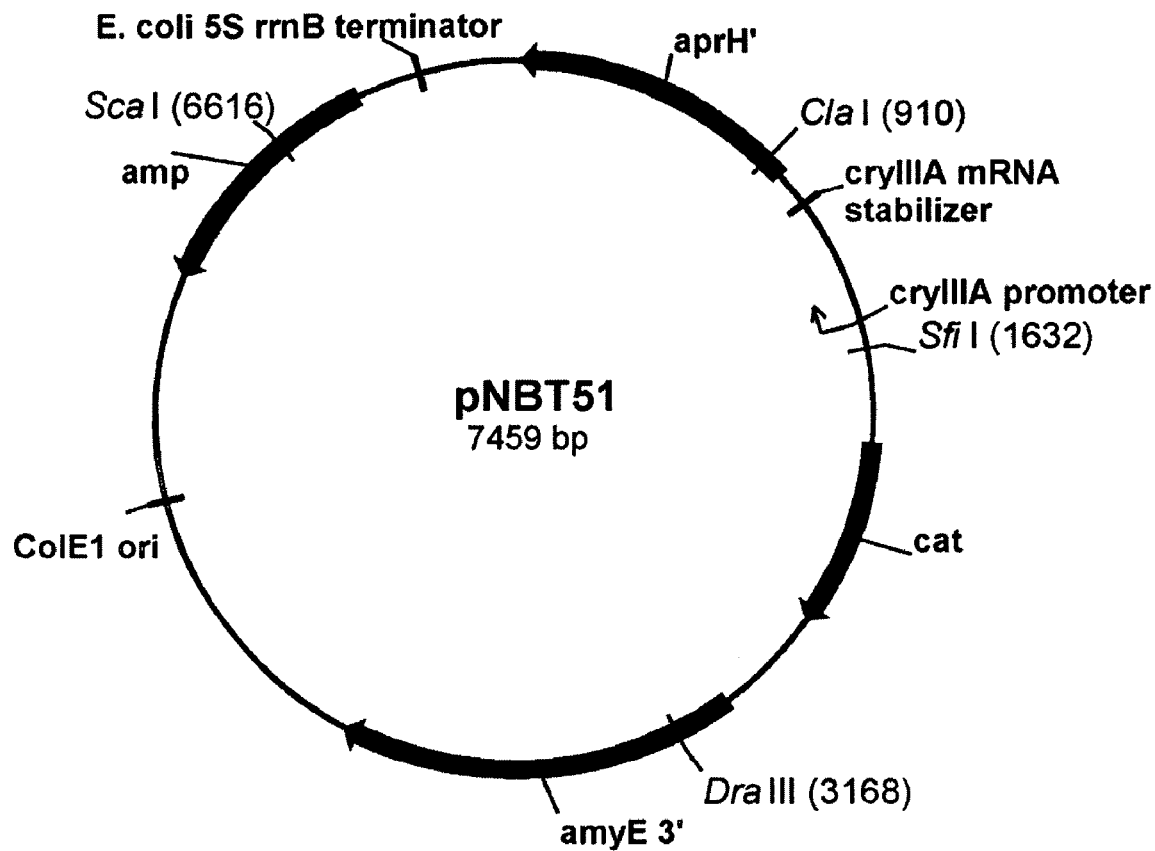
FIG. 6 shows a restriction map of pNBT51.

C. The resulting plasmid was designated pNBT51 (pDG268-$P_{cryIII}$/cryIIIAstab/SAVΔ) (FIG. 6).

Figure 7:
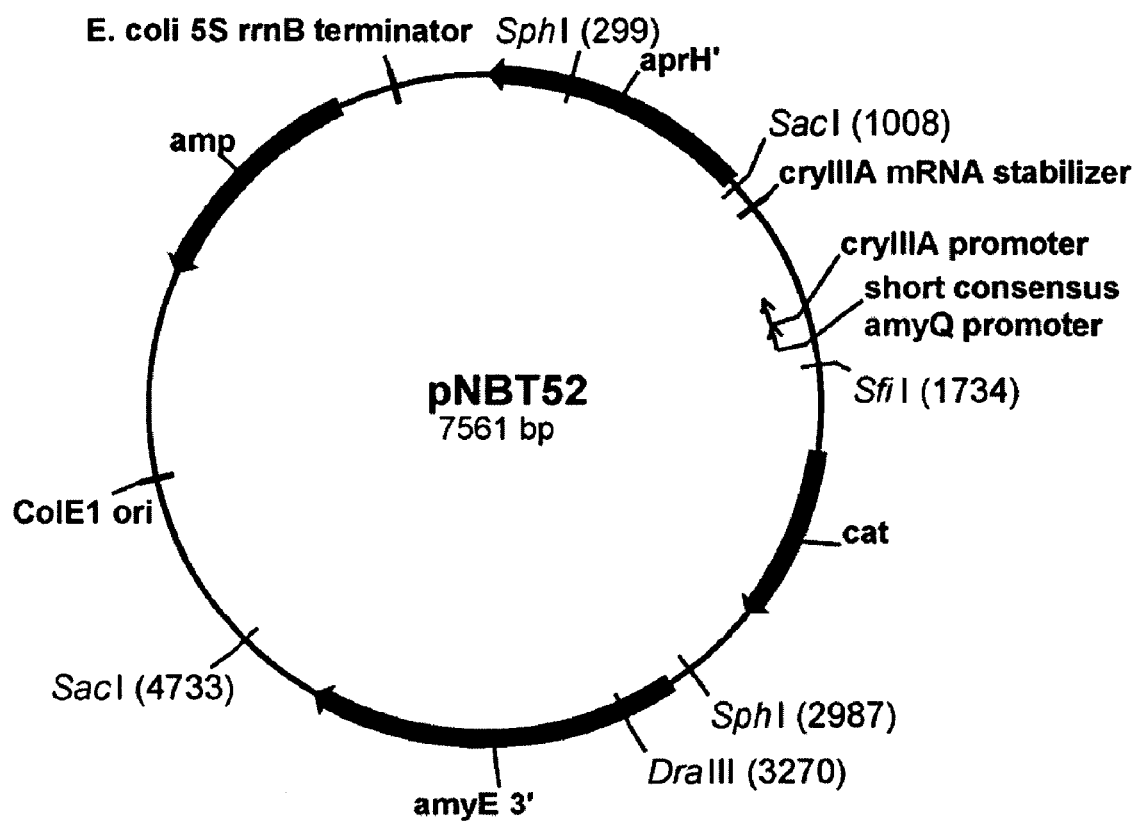
FIG. 7 shows a restriction map of pNBT52.

Plasmid pNBT52. Plasmid pNBT51 was digested with Sfi I, and the ends were blunted by incubation for 20 minutes at 11° C. with T4 DNA polymerase (Roche Diagnostics Corporation, Indianapolis, Ind., USA) and 25 μM of each dNTP, followed by heat-inactivation of the polymerase by incubation for 10 minutes at 75° C. The blunt-ended plasmid was then digested with Dra III and analyzed by 0.8% agarose electrophoresis in TBE buffer, and a vector fragment of approximately 5920 bp was purified using a QIAQUICK® Gel Extraction Kit. Plasmid pNBT20 (pDG268MCS-$P_{short\ consensus\ amyQ}$/SAV; U.S. Pat. No. 6,255,076) was digested with Dra III and EcI 136II, and a fragment of approximately 1641 bp bearing a short consensus amyQ promoter ($P_{short\ consensus\ amyQ}$) was purified using a QIAQUICK® Gel Extraction Kit. The pNBT51 vector fragment and $P_{short\ consensus\ amyQ}$ fragment were ligated as described above, and E. coli DH5α was transformed with the ligation as described above, selecting for ampicillin resistance on 2×YT ampicillin plates at 37° C. Plasmid DNA was isolated from several transformants using a QIAPREP® 8 Miniprep Kit (QIAGEN, Valencia, Calif., USA), digested with Sph I, and analyzed by 0.8% agarose electrophoresis in TBE buffer. One plasmid with expected restriction fragments of approximately 4873 bp and 2688 bp was designated pNBT52 (pDG268-$P_{short\ consensus\ amyQ}$/cryIIIAstab/SAVΔ) (FIG. 7).

Figure 8:
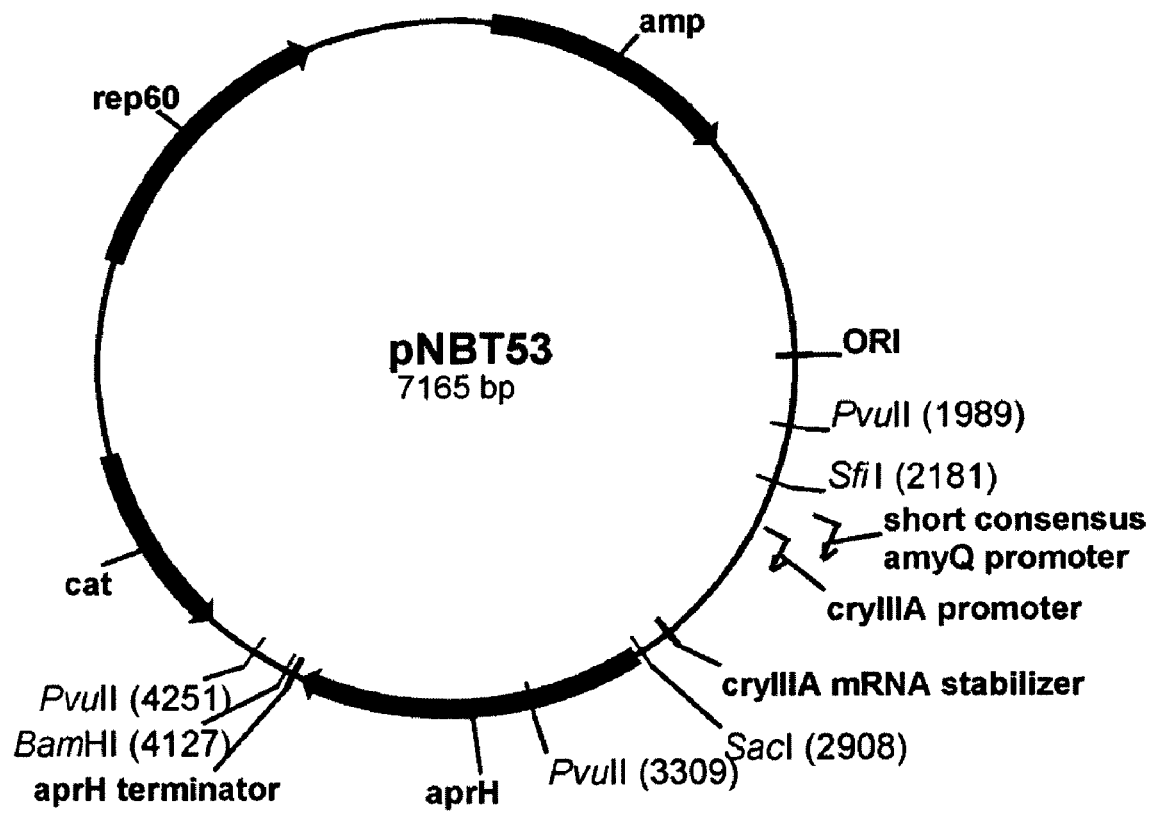
FIG. 8 shows a restriction map of pNBT53.

Plasmid pNBT53. Plasmid pNBT6 (pHP13amp-SAV; U.S. Pat. No. 6,255,076) was digested with Sfi I and Sac I and analyzed by 0.8% agarose electrophoresis in TBE buffer, and a vector fragment of approximately 6438 bp was purified using a QIAQUICK® Gel Extraction Kit. Plasmid pNBT52 was digested with Sfi I and Sac I and analyzed by 0.8% agarose electrophoresis in TBE buffer, and a fragment of approximately 727 bp bearing the $P_{short\ consensus\ amyQ}$/$P_{cryIIIA}$/cryIIIAstab tandem promoter was purified using a QIAQUICK® Gel Extraction Kit. The pNBT6 vector fragment and $P_{short\ consensus\ amyQ}$/$P_{cryIIIA}$/cryIIIAstab fragment were ligated as described above, and E. coli DH5α cells were transformed with the ligation as described above, selecting for ampicillin resistance on 2×YT ampicillin plates at 37° C. Plasmid DNA was isolated from several transformants using a QIAPREP® 8 Miniprep Kit, digested with Pvu II, and analyzed by 0.8% agarose electrophoresis using TBE buffer. One plasmid with expected restriction fragments of approximately 4903 bp, 1320 bp, and 942 bp was designated pNBT53 (pHP13amp-$P_{short\ consensus\ amyQ}$/$P_{cryIIIA}$/cryIIIAstab/SAV) (FIG. 8).

Figure 9:
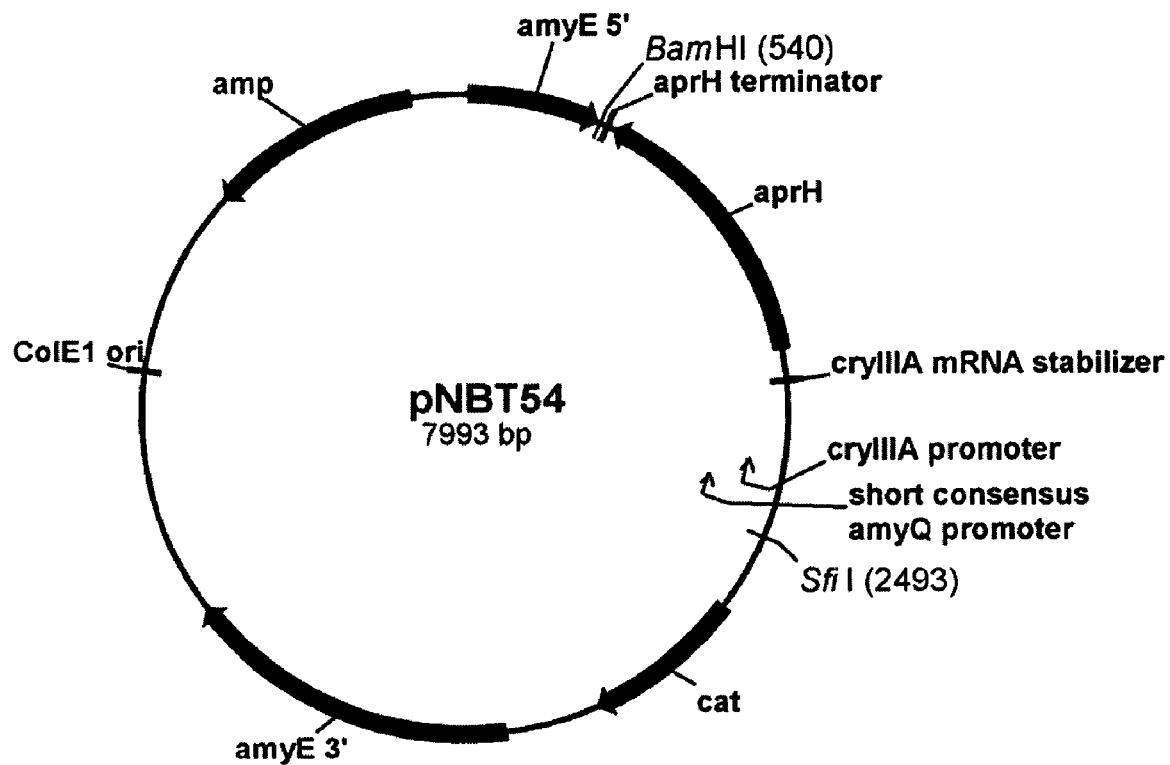
FIG. 9 shows a restriction map of pNBT54.

Plasmid pNBT54. Plasmid pNBT1 (pDG268MCS; U.S. Pat. No. 6,255,076) was digested with Sfi I and Bam HI and analyzed by 0.8% agarose electrophoresis in TBE buffer, and a vector fragment of approximately 6040 bp was purified using a QIAQUICK® Gel Extraction Kit. Plasmid pNBT53 was digested with Sfi I and Bam HI and analyzed by 0.8% agarose electrophoresis in TBE buffer, and a fragment of approximately 1953 bp bearing the $P_{short\ consensus\ amyQ}$/$P_{cryIIIA}$/cryIIIAstab/SAV cassette was purified using a QIAQUICK® Gel Extraction Kit. The pNBT1 vector fragment and $P_{short\ consensus\ amyQ}$/$P_{cryIIIA}$/cryIIIAstab/SAV fragment were ligated as described above, and E. coil DH5α cells were transformed with the ligation as described above, selecting for ampicillin resistance on 2×YT ampicillin plates at 37° C. Plasmid DNA was isolated from several transformants using a QIAPREP® 8 Miniprep Kit and analyzed by simultaneous digestion with Sfi I and Bam HI followed by 0.8% agarose gel electrophoresis in TBE buffer. One plasmid with expected restriction fragments of approximately 6040 bp and 1953 bp was designated pNBT54 (pDG268MCS-$P_{short\ consensus\ amyQ}$/$P_{cryIIIA}$/cryIIIAstab/SAV) (FIG. 9).

Figure 10:
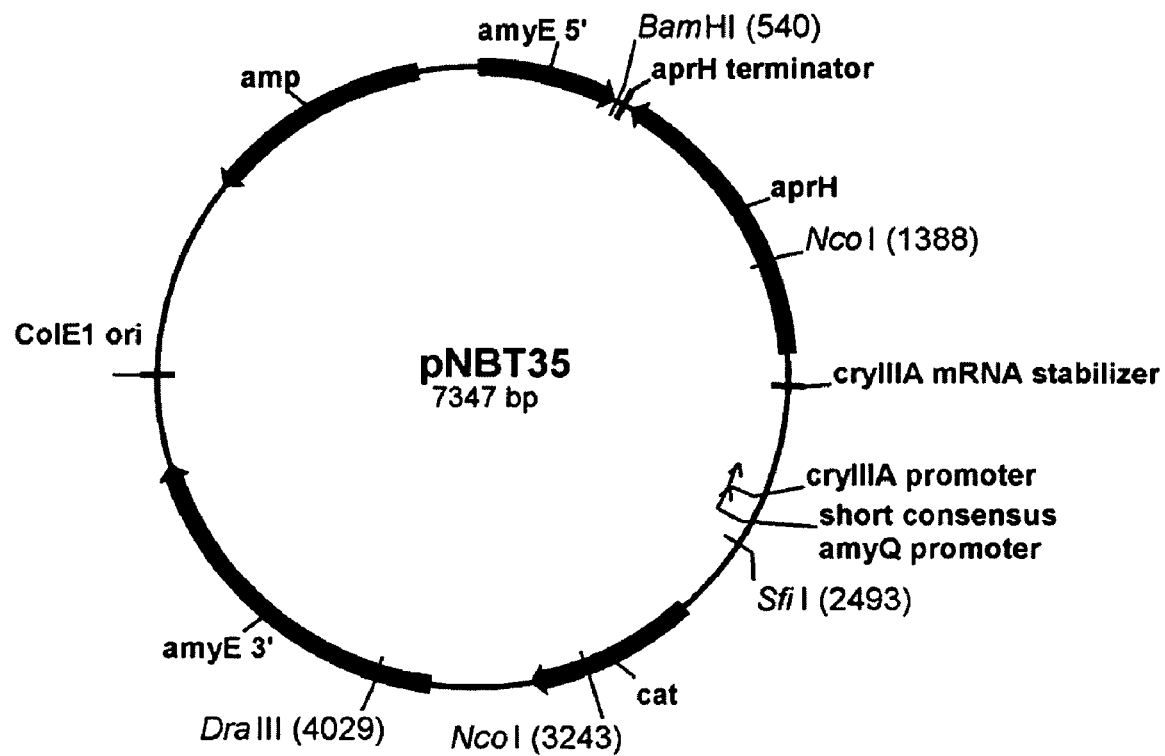
FIG. 10 shows a restriction map of pNBT35.

Plasmid pNBT35. Plasmid pNBT2 (pDG268MCSΔ-$Pr_{cryIIIA}$/cryIIIAstab/SAV; U.S. Pat. No. 6,255,076) was digested with Sfi I and Bam HI and analyzed by 0.8% agarose gel electrophoresis in TBE buffer, and a vector fragment of approximately 5394 bp was purified using a QIAQUICK® Gel Extraction Kit. Plasmid pNBT54 was digested with Sfi I and Bam HI, and analyzed by 0.8% agarose gel electrophoresis in TBE buffer, and a fragment of approximately 1953 bp bearing the $P_{short\ consensus\ amyQ}$/$P_{cryIIIA}$/cryIIIAstab/SAV cassette was purified using a QIAQUICK® Gel Extraction Kit. The pNBT2 vector fragment and $P_{short\ consensus\ amyQ}$/$P_{cryIIIA}$/cryIIIAstab/SAV fragment were ligated as described above, and E. coli DH5α cells were transformed with the ligation as described above, selecting for ampicillin resistance on 2×YT ampicillin plates at 37° C. Plasmid DNA was isolated from several transformants using a QIAPREP® 8 Miniprep Kit, digested with Nco I, and analyzed by 0.8% agarose gel electrophoresis in TBE buffer. One plasmid with expected restriction fragments of approximately 5492 bp and 1855 bp was designated pNBT35 (pDG268MCSΔ-$P_{short\ consensus\ amyQ}$/$P_{cryIIIA}$/cryIIIAstab/SAV) (FIG. 10).

Plasmid pNBT30. Plasmid pNBT30 was constructed to contain a PCR clone of the amyL4199 variant of the amyL gene promoter (U.S. Pat. No. 6,100,063). Bacillus licheniformis SJ1904 genomic DNA was isolated according to the procedure of Pitcher et al., 1989, supra. The amyL4199 promoter ($P_{amyL4199}$) gene was amplified by PCR from Bacillus licheniformis SJ1904 genomic DNA using primers 950872 and 991151 shown below. Primer 950872 incorporates an Sfi I restriction site, and primer 991151 incorporates a Sac I restriction site and the variant nucleotides of $P_{amyL4199}$.

```
Primer 950872:
                                      (SEQ ID NO: 8)
5'-CCAGGCCTTAAGGGCCGCATGCGTCCTTCTTTGTGCT-3'

Primer 991151:
                                      (SEQ ID NO: 9)
5'-GAGCTCCTTTCAATGTGATACATATGA-3'
```

The PCR was performed using AMPLITAQ® Gold DNA Polymerase (Applied Biosystems, Foster City, Calif., USA) according to manufacturer's recommendations, except that the $MgCl_2$ concentration was 3 mM, rather than the standard 1.5 mM. The amplification reaction (50 μl) was composed of 10 mM Tris-HCl (pH 8.3), 50 mM KCl, 3.0 mM $MgCl_2$, 200 μM of each dNTP, 0.5 μM of each primer, 0.25 units of AMPLITAQ® Gold DNA Polymerase, and approximately 200 ng of template DNA. The PCR was performed in a ROBOCYCLER® 40 Temperature Cycler programmed for 1 cycle at 95° C. for 9 minutes; 30 cycles each at 95° C. for 1 minute, 55° C. for 1 minute, and 72° C. for 1 minute; and 1 cycle at 72° C. for 3 minutes.

Figure 11:
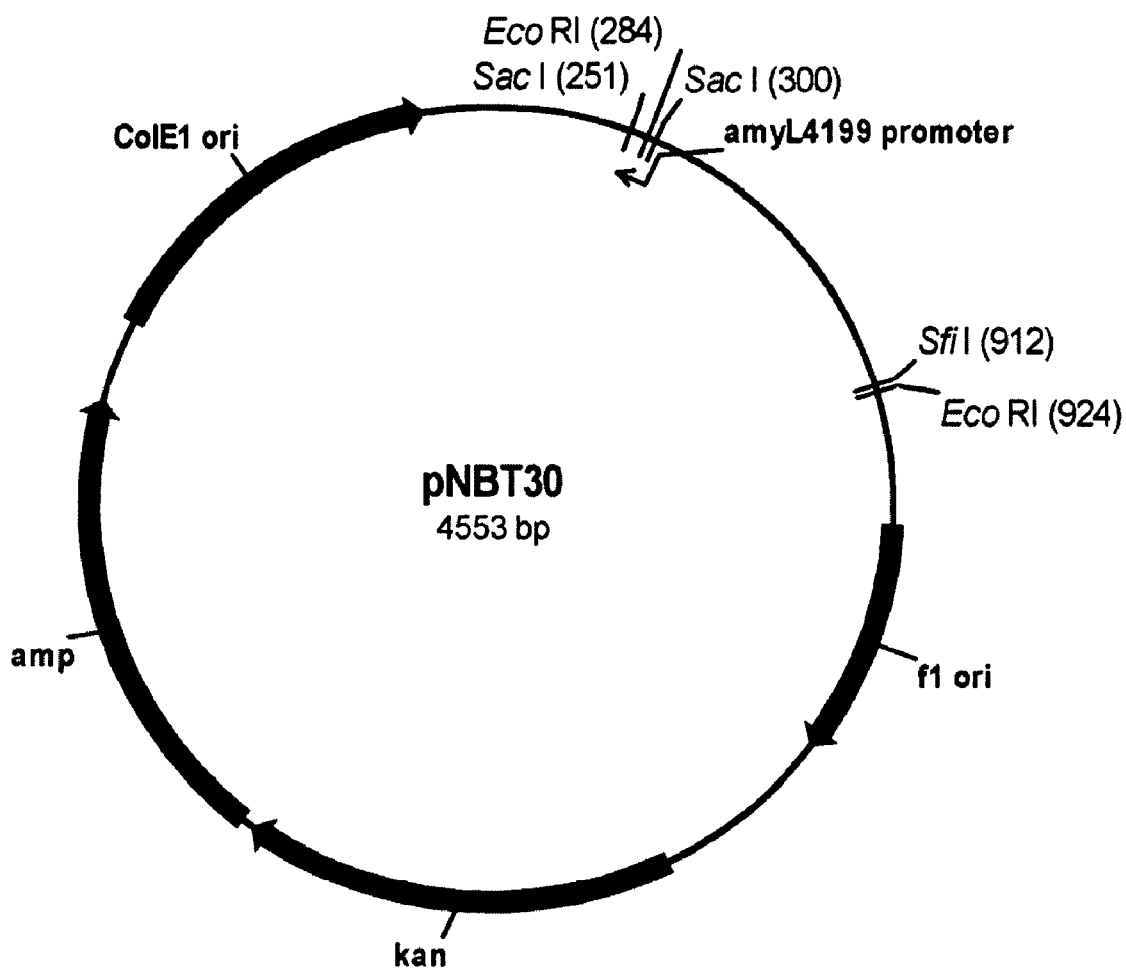
FIG. 11 shows a restriction map of pNBT30.

The resulting PCR product of approximately 625 bp was cloned into vector pCR2.1 using a TOPO® TA Cloning Kit (Invitrogen, Carlsbad, Calif., USA) and transformed into ONE SHOT® TOP10 Chemically Competent E. coli cells (Invitrogen, Carlsbad, Calif., USA) according to the manufacturer's instructions. Plasmid DNA was isolated from several transformants using a QIAPREP® 8 Miniprep Kit and analyzed for the presence of the cloned PCR fragment by digestion with Eco RI followed by 0.8% agarose electrophoresis in TBE buffer. One plasmid with expected restriction fragments of approximately 3913 bp and 640 bp was designated pNBT30 (pCR2.1-amyL4199) (FIG. 11). The DNA sequence of the cloned PCR fragment was confirmed by DNA sequencing.

Figure 12:
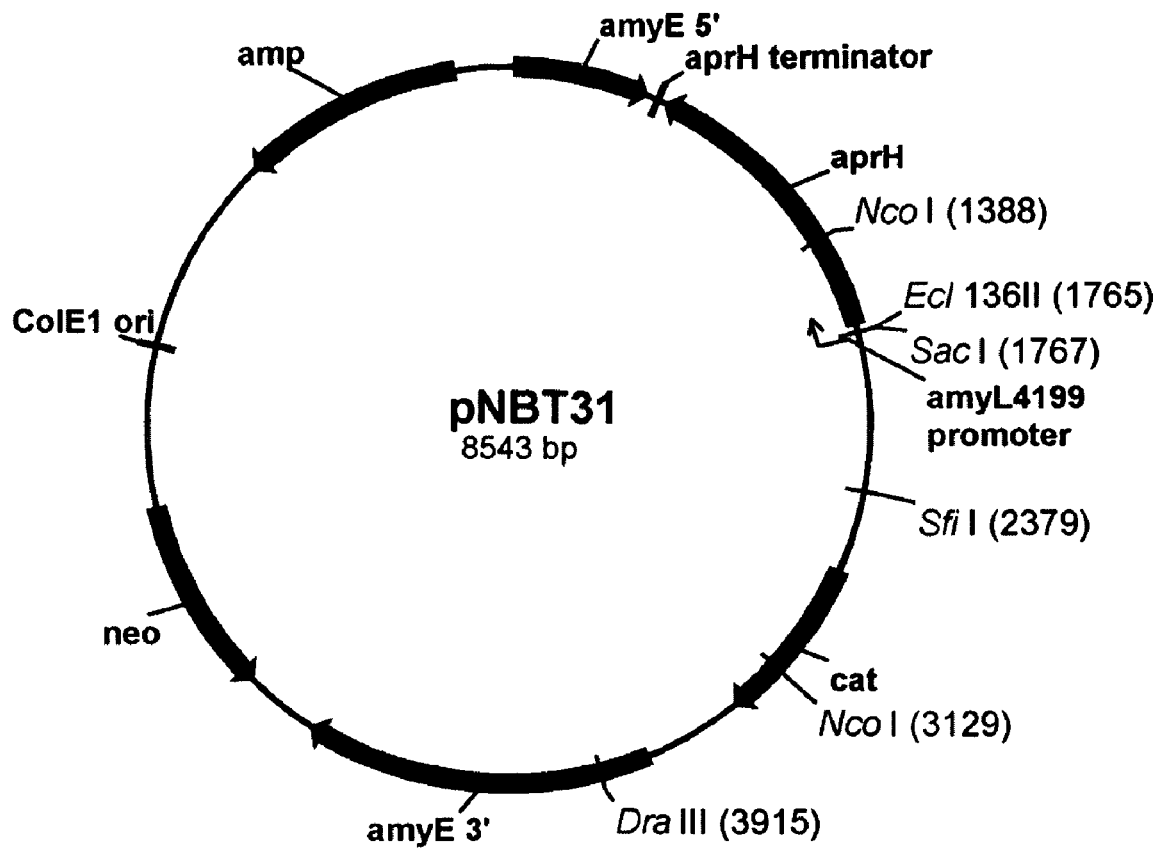
FIG. 12 shows a restriction map of pNBT31.

Plasmid pNBT31. Plasmid pNBT3 (pDG268MCSΔneo-Pr$_{cryIIIA}$/cryIIIAstab/SAV; U.S. Pat. No. 6,255,076) was digested with Sfi I and Sac I and analyzed by 0.8% agarose electrophoresis in TBE buffer, and a vector fragment of approximately 7931 bp was purified using a QIAQUICK® Gel Extraction Kit. Plasmid pNBT30 was digested with Sfi I and Sac I, analyzed by 0.8% agarose electrophoresis in TBE buffer, and a fragment of approximately 612 bp bearing P$_{amyL4199}$ was purified using a QIAQUICK® Gel Extraction Kit. The pNBT3 vector fragment and P$_{amyL4199}$ fragment were ligated as described above, and E. coli XL1-Blue cells (Stratagene Corporation, La Jolla, Calif., USA) were transformed with the ligation according to the manufacturer's instructions, selecting for ampicillin resistance on 2× YT ampicillin plates at 37° C. Plasmid DNA was isolated from several transformants using a QIAPREP® 8 Miniprep Kit, digested with Nco I, and analyzed by 0.8% agarose electrophoresis in TBE buffer. One plasmid with expected restriction fragments of approximately 6802 bp and 1741 bp was designated pNBT31 (FIG. 12).

Figure 13:
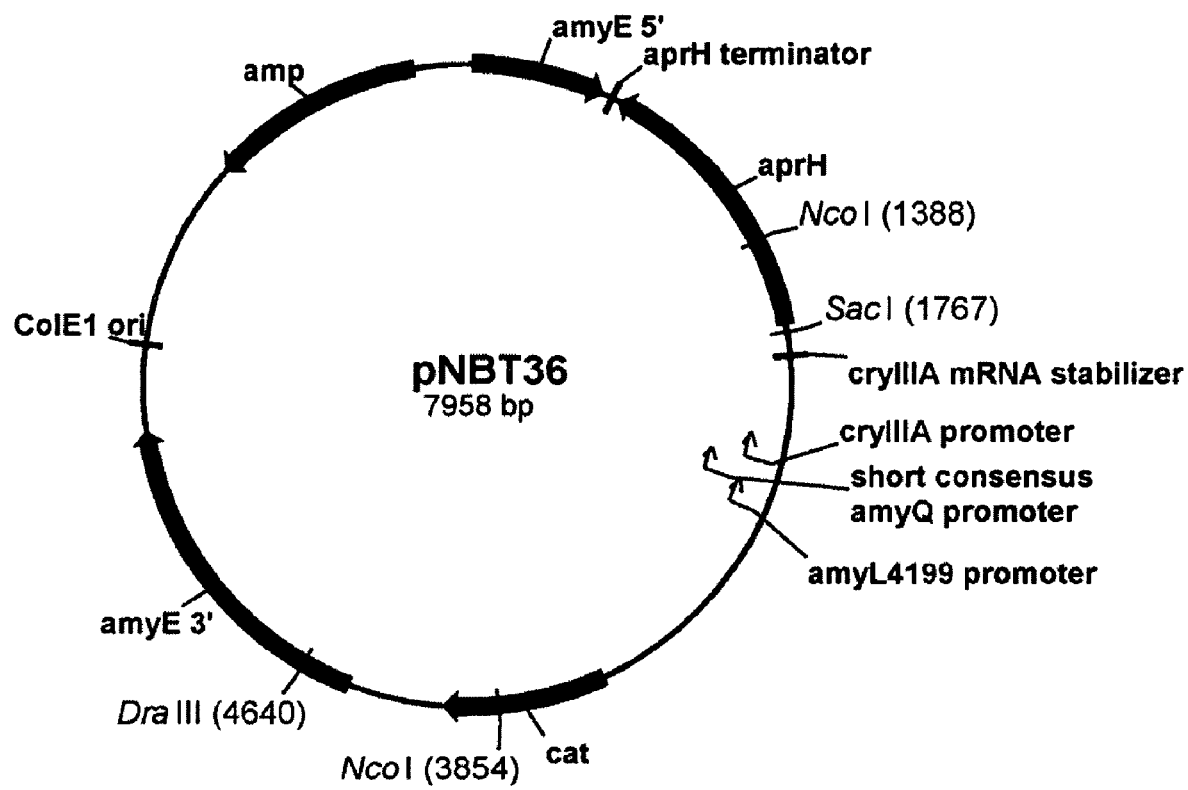
FIG. 13 shows a restriction map of pNBT36.

Plasmid pNBT36. Plasmid pNBT35 was digested with Sfi I, and the ends were blunted using T4 DNA polymerase and dNTPs, as described above. The blunt ended plasmid was then digested with Dra III, and analyzed by 0.8% agarose electrophoresis in TBE buffer. A vector fragment of approximately 5808 bp was purified using a QIAQUICK® Gel Extraction Kit. Plasmid pNBT31 was digested with Dra III and Ecl 136II, analyzed by 0.8% agarose electrophoresis in TBE buffer, and a fragment of approximately 2150 bp bearing P$_{amyL4199}$ was purified using a QIAQUICK® Gel Extraction Kit. The pNBT35 vector fragment and P$_{amyL4199}$ fragment were ligated as described above, and E. coli SURE® cells (Stratagene Corporation, La Jolla, Calif., USA) were transformed with the ligation according to the manufacturer's instructions, selecting for ampicillin resistance on 2× YT ampicillin plates at 37° C. Plasmid DNA was isolated from several transformants using a QIAPREP® 8 Miniprep Kit, digested with Nco I, and analyzed by 0.8% agarose electrophoresis in TBE buffer. One plasmid with expected restriction fragments of approximately 5492 bp and 2466 bp was designated pNBT36 (FIG. 13).

Figure 14:
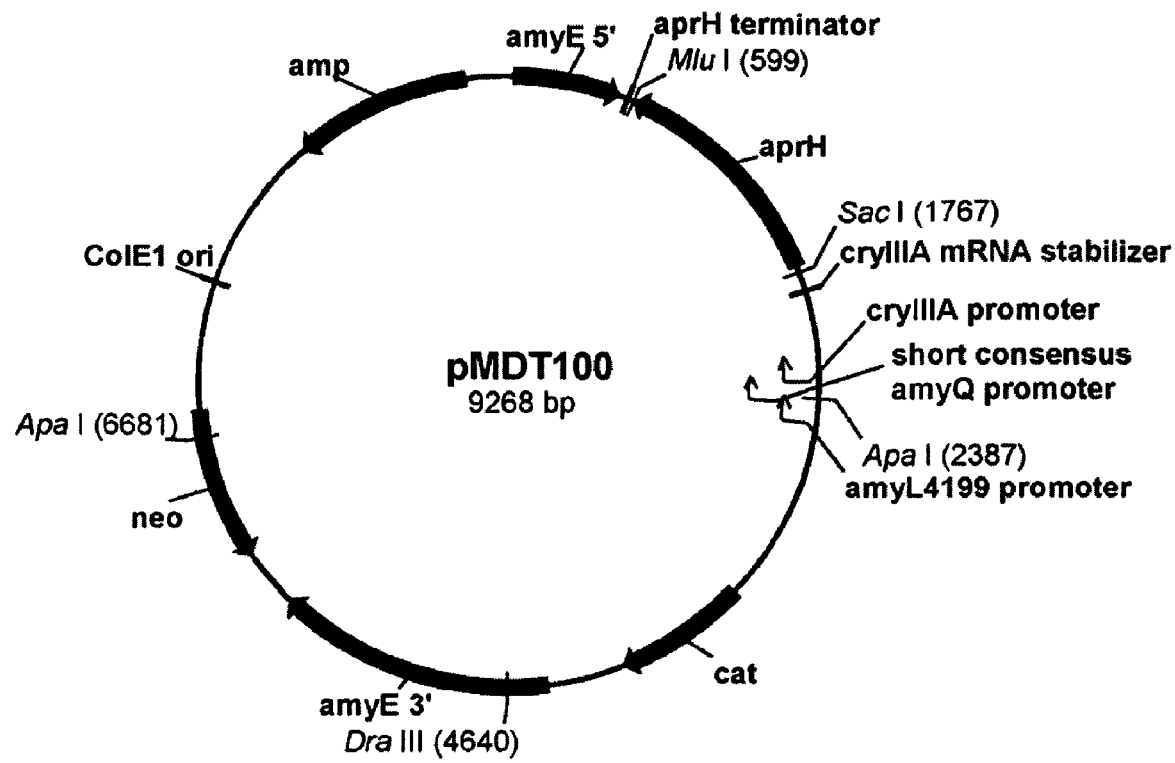
FIG. 14 shows a restriction map of pMDT100.

Plasmid pMDT100. Plasmid pNBT13 (pDG268Δneo-P$_{amyL}$/P$_{cryIIIA}$/cryIIIAstab/SAV; U.S. Pat. No. 6,255,076) was digested with Dra III and Sac I, and a vector fragment of approximately 6395 bp was purified using a QIAQUICK® Gel Extraction Kit. Plasmid pNBT36 was digested with Dra III and Sac I, analyzed by 0.8% agarose electrophoresis in TBE buffer, and a fragment of approximately 2873 bp bearing the P$_{amyL4199}$/P$_{amyQ(sc)}$/P$_{cryIIIA}$ triple tandem promoter was purified using a QIAQUICK® Gel Extraction Kit. The pNBT13 vector fragment and P$_{amyL4199}$/P$_{amyQ(sc)}$/P$_{cryIIIA}$ fragment were ligated as described above, and E. coli SURE® cells were transformed with the ligation as described above, selecting for ampicillin resistance on 2×YT ampicillin plates at 37° C. Plasmid DNA was isolated from several transformants using a QIAPREP® 8 Miniprep Kit, digested with Apa I, and analyzed by 0.8% agarose electrophoresis in TBE buffer. One plasmid with expected restriction fragments of approximately 4974 bp and 4294 bp was designated pMDT100 (FIG. 14).

Example 8

Expression of the Bacillus licheniformis M.Bli1904 II DNA Methyltransferase Gene in Bacillus subtilis The Bacillus licheniformis M.Bli1904II DNA methyltransferase gene was inserted into the chromosome of Bacillus subtilis in order to express the DNA methyltransferase in that host, thereby allowing methylation of DNA in Bacillus subtilis.

Plasmid pMDT100 was digested with Sac I and Mlu I and analyzed by 0.8% agarose electrophoresis in TBE buffer, and a vector fragment of approximately 8100 bp was purified using a QIAQUICK® Gel Extraction Kit. Plasmid pMDT138 was digested with Sac I and Mlu I, and a fragment of approximately 1033 bp bearing the M.Bli1904II gene was purified using a QIAQUICK® Gel Extraction Kit. The pMDT100 vector fragment and M.Bli1904II gene fragment were ligated as described above. This ligation placed the M.Bli1904II gene downstream of the P$_{amyL4199}$/P$_{short\ consensus\ amyQ}$/P$_{cryIIIA}$/cryIIIAstab promoter and upstream of the aprH transcription terminator. Bacillus subtilis 168Δ4 was transformed with the ligation according to the procedure of Anagnostopoulos and Spizizen, 1961, J. Bacteria 81: 741-746 and transformants were selected for chloramphenicol resistance on TBAB chloramphenicol plates at 37° C. Chloramphenicol-resistant transformants were screened for neomycin sensitivity on TBAB neomycin plates at 37° C. to determine whether the DNA had inserted into the amyE gene of the Bacillus subtilis chromosome by double crossover.

The presence of the M.Bli1904II DNA methyltransferase expression cassette at the amyE locus was confirmed by PCR using primers 994112 and 999592 shown below (which bind within the triple tandem promoter and M.Bli1904II DNA methyltransferase gene, respectively) and primers 999611 and 960456 shown below (which bind within the M.Bli1904II DNA methyltransferase gene and amyE gene, respectively). One such transformant, containing the cat gene and the M.Bli1904II DNA methyltransferase expression cassette at the amyE locus, was designated Bacillus subtilis MDT101.

```
Primer 994112:
5'-GCGGCCGCTCGCTTTCCAATCTGA-3'      (SEQ ID NO: 10)

Primer 999592:
5'-ATCGATCAGCTTGGATAAACCCTA-3'      (SEQ ID NO: 11)

Primer 999611:
5'-GAGCTCTGCAAGGAGGTATAATTTTG-3'    (SEQ ID NO: 12)

Primer 960456:
5'-CGTCGACGCCTTTGCGGTAGTGGTGCTT-3'  (SEQ ID NO: 13)
```

The PCRs were performed using Taq DNA Polymerase (New England Biolabs, Inc., Beverly, Mass., USA) according to the manufacturer's instructions. The amplification reactions (50 µl) were composed of 10 mM Tris-HCl (pH 8.3), 50 mM KCl, 3.0 mM MgCl$_2$, 200 µM of each dNTP, 0.5 µM of each primer, 0.25 units of Taq DNA Polymerase, and approximately 200 ng of genomic DNA. The PCRs were performed in a ROBOCYCLER® 40 Temperature Cycler programmed for 1 cycle at 95° C. for 2 minutes; 30 cycles each at 95° C. or 2 minutes, 55° C. or 2 minutes, and 72° C. for 2 minutes; and 1 cycle at 72° C. for 3 minutes.

In order to confirm that the cloned M.Bli1904II DNA methyltransferase was able to methylate DNA, plasmid DNA was isolated from *Bacillus* strains expressing the methyltransferase and tested for DNA methylation. *Bacillus subtilis* strains 168Δ4 and MDT101 were transformed with plasmid pCJ791 (U.S. Published Application 20030175902) according to the procedure of Anagnostopoulos and Spizizen, 1961, supra, selecting for erythromycin resistance on TBAB erythromycin/lincomycin plates at 34° C. Plasmid pCJ791 DNA was isolated from one transformant each of *Bacillus subtilis* 168Δ4 and *Bacillus subtilis* MDT101, using a QIAGEN® Plasmid Midi Kit.

*Bacillus licheniformis* SJ1904 was transformed with pCJ791 DNA from the *Bacillus subtilis* MDT101 transformant by electroporation according to the procedure of Xue et al., 1999, *J. Microbial. Methods* 34(3): 183-191. Briefly, 1-5 ml of an overnight culture of *Bacillus licheniformis* grown in LBS medium was used to inoculate 50 ml of fresh LBS medium, and the culture was incubated at 37° C. and 250 rpm. The culture was grown to stationary phase, and cells were harvested by centrifugation at 6500×g when the culture experienced an increase in growth rate after a period of slow growth (1-3 hours after the end of exponential growth). Cells were washed twice with 50 ml of ice-cold MSG (0.5 M mannitol, 0.5 M sorbitol, 10% glycerol) and resuspended in approximately 750 μl of MSG. Cells were transformed as follows or stored at −20° C. Sixty μl of electrocompetent cells were mixed with plasmid DNA in an electroporation cuvette with a 1-mm electrode gap and subjected to an electrical pulse using a GENE PULSER® (Bio-Rad Laboratories, Inc., Hercules, Calif., USA) set to 25 μF, 200Ω, and 1.0 kV. Electroporated cells were then transferred to 950 μl of LBSM medium containing 0.2 μg of erythromycin per ml for induction of erythromycin resistance. The transformants were incubated for 2.5-3 hours at 34° C. and 250 rpm and then selected for erythromycin resistance on TBAB erythromycin/lincomycin plates at 34° C.

Plasmid pCJ791 DNA was isolated from one *Bacillus licheniformis* SJ1904 transformant, using a QIAGEN® Plasmid Midi Kit. Plasmid pCJ791 DNA isolated from *Bacillus subtilis* 168Δ4, *Bacillus subtilis* MDT101, and *Bacillus licheniformis* SJ1904 was digested with Fnu 4HI and with Sac I. Plasmid pCJ791 has 12 Fnu 4HI recognition sites and three Sac I recognition sites. Fnu 4HI, which cleaves DNA at the sequence GCNGC, was able to digest pCJ791 plasmid DNA from *Bacillus subtilis* 168Δ4 but not pCJ791 plasmid DNA from *Bacillus subtilis* MDT101 or *Bacillus licheniformis* SJ1904, indicating that plasmid DNA from the latter two sources was methylated at the GCNGC sites. Sac I, which cleaves DNA at the sequence GAGCTC and is thus unaffected by methylation of the sequence GCNGC, was able to cleave pCJ791 plasmid DNA from all three sources.

Example 9

Cloning of the *Bacillus licheniformis* Bli1904II restriction Endonuclease Gene

The *Bacillus licheniformis* Bli1904II restriction endonuclease coding region was cloned by PCR. *Bacillus licheniformis* SJ1904 genomic DNA was isolated according to the procedure of Pitcher at al., 1989, supra. FIG. 3 shows the region of the *Bacillus licheniformis* chromosome comprising the genes encoding the Bli1904II restriction endonuclease and M.Bli1904II DNA methyltransferase. An approximately 1158 bp fragment of the *Bacillus licheniformis* SJ1904 chromosome including the coding region of the Bli1904II gene, comprising nucleotides 443-1588 of SEQ ID NO: 5 (FIG. 3), was amplified by PCR from *Bacillus licheniformis* SJ1904 genomic DNA using primers 060625 and 060626 shown below. Primer 060625 incorporates a Kpn I restriction site, and primer 060626 incorporates a Bam HI restriction site.

Primer 060625:
5'-GGTACCATGTTCTATACTAATCAACC-3' (SEQ ID NO: 14)

Primer 060626:
5'-GGATCCTTATTTGTTTTCATTTTCAA-3' (SEQ ID NO: 15)

The PCR was performed using Pfx DNA Polymerase (Invitrogen, Carlsbad, Calif., USA). The amplification reaction (50 μl) was composed of 1× Pfx Amplification Buffer (Invitrogen, Carlsbad, Calif., USA), 1.5 mM MgSO$_4$, 300 μM of each dNTP, 0.3 μM of each primer, 1.25 units of PLATINUM® Pfx DNA Polymerase, and approximately 200 ng of template DNA. The reaction was performed in a ROBOCYCLER® 40 Temperature Cycler programmed for 1 cycle at 95° C. for 2 minutes; 30 cycles each at 95° C. for 1 minute, 55° C. for 1 minute, and 68° C. for 1 minute; and 1 cycle at 68° C. for 3 minutes.

Figure 15:
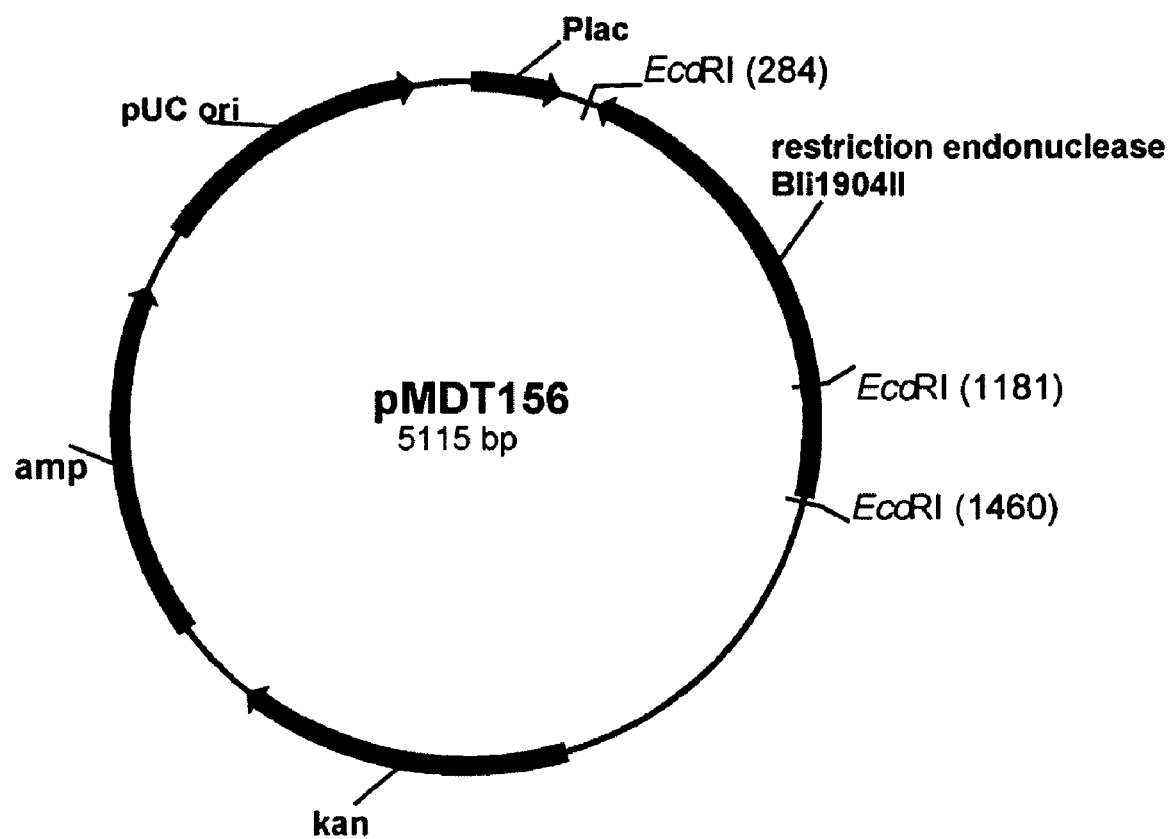
FIG. 15 shows a restriction map of pMDT156.

The resulting PCR product of approximately 1158 bp was cloned into pCR4Blunt using a Zero Blunt® TOPO® PCR Cloning Kit for Sequencing (Invitrogen, Carlsbad, Calif., USA) and transformed into ONE SHOT® TOP10 Chemically Competent *E. coli* cells according to the manufacturer's instructions. Plasmid DNA was isolated from one transformant using a QIAGEN® Plasmid Midi Kit and confirmed by digestion with Eco RI followed by 0.8% agarose electrophoresis in TBE buffer, which yielded expected fragments of 3939 bp, 897 bp, and 279 bp. The DNA sequence of the cloned PCR fragment was confirmed by DNA sequencing. This plasmid was designated pMDT156 (FIG. 15), and the *E. coli* TOP10 transformant containing the plasmid was designated MDT46. MDT46 was deposited on Sep. 7, 2006, under the terms of the Budapest Treaty with the Agricultural Research Service Patent Culture Collection, Northern Regional Research Center, 1815 University Street, Peoria, Ill. 61604, and given the accession number NRRL B-41968.

Example 10

Construction of a Deleted Version of the *Bacillus licheniformis* Bli1904II Restriction Endonuclease Gene A deleted version of the *Bacillus licheniformis* Bli1904II restriction endonuclease gene was constructed by PCR to permit deletion of the native gene in *Bacillus licheniformis*.

Genomic DNA was isolated from *Bacillus licheniformis* SJ1904 according to the procedure of Pitcher et al., 1989, supra, and two fragments from the Bli1904II chromosomal locus were amplified by PCR.

An approximately 505 bp fragment of the *Bacillus licheniformis* SJ1904 chromosome upstream of the Bli1904II gene, comprising nucleotides 1616-2102 of SEQ ID NO: 5, was amplified by PCR from *Bacillus licheniformis* SJ1904 genomic DNA using primers 999592 and 999593 shown below. Primer 999592 incorporates a Cla I restriction site.

```
Primer 999592:
5'-ATCGATCAGCTTGGATAAACCCTA-3'        (SEQ ID NO: 16)

Primer 999593:
5'-TTCACAAGATCTATTTCTTCTTTCAGACC      (SEQ ID NO: 17)
C-3'
```

The PCR was performed using PLATINUM® Pfx DNA Polymerase, as described in Example 6.

An approximately 507 bp fragment of the *Bacillus licheniformis* SJ1904 chromosome including the last 42 codons of the Bli1904II gene plus downstream DNA, comprising nucleotides 1-487 of SEQ ID NO: 5, was amplified from *Bacillus licheniformis* SJ1904 genomic DNA using primers 999594 and 999595. Primer 999594 incorporates a Not I restriction site.

```
Primer 999594
5'-AGAAATAGATCTTGTGAAATGGGTTCTTA      (SEQ ID NO: 18)
T-3'

Primer 999595:
5'-GCGGCCGCTCATGTTCCCATATTCTT-3'      (SEQ ID NO: 19)
```

The PCR was performed using PLATINUM® Pfx DNA Polymerase, as described in Example 6, except that the MgSO$_4$ concentration was 1.5 mM.

Primer 999593 (used in the upstream amplification) and primer 999594 (used in the downstream amplification) have complementary 5' ends. Therefore, the two amplifications had complementary ends that would permit fusion of the two PCR fragments, as described below. Primers were removed from the two amplifications using a QIAQUICK® PCR Purification Kit (QIAGEN Inc., Valencia, Calif., USA) according to the manufacturer's instructions. The two amplifications were used as template DNA for a third PCR, using primers 999592 and 999595, which fused the two fragments via the complementary ends provided by the sequences of primers 999593 and 999594. The PCR was performed using PLATINUM® Pfx DNA Polymerase, as described in Example 6, except that the template DNA consisted of 2 µl of each of the two amplifications.

Figure 16:
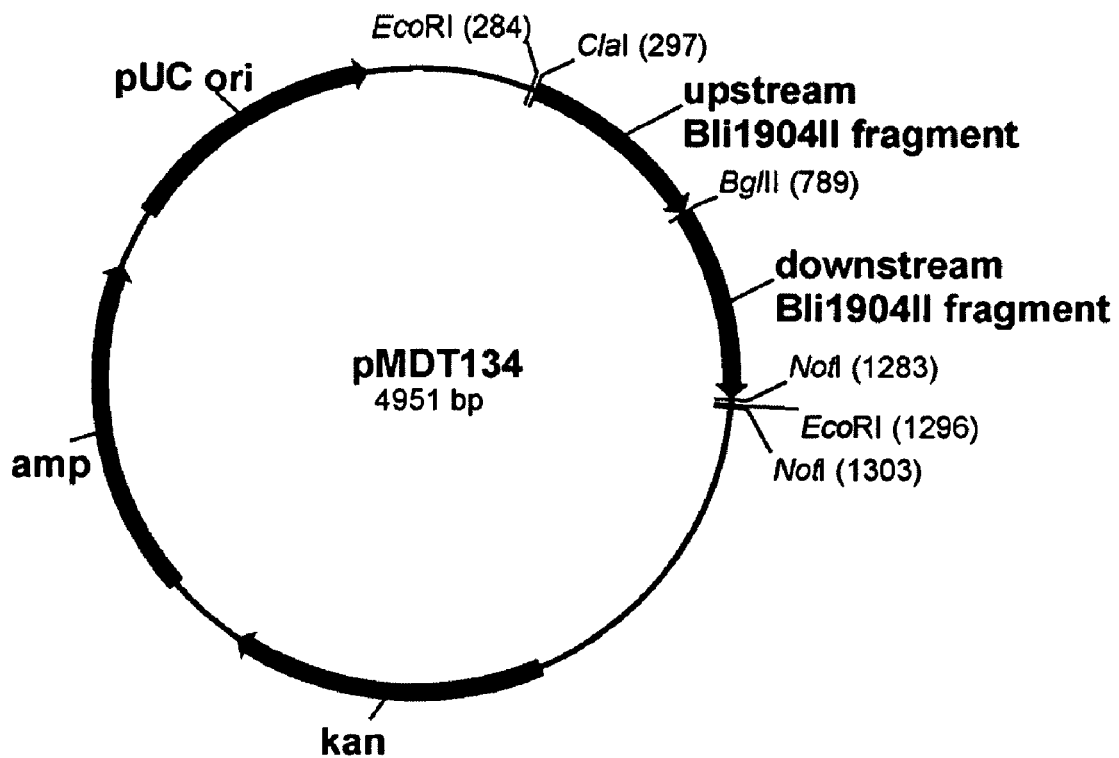
FIG. 16 shows a restriction map of pMDT134.

The resulting approximately 994 bp PCR product was purified using a QIAQUICK® Gel Extraction Kit and cloned into vector pCR4Blunt using a Zero Blunt® TOPO® PCR Cloning Kit for Sequencing, and transformed into ONE SHOT® TOP10 Chemically Competent *E. coli* cells as described in Example 6. Plasmid DNA from several transformants was purified using a BIOROBOT® 9600 (QIAGEN Inc., Valencia, Calif., USA) and tested for the presence and orientation of the cloned PCR fragment by digestion with Eco RI and with Not I followed by 0.8% agarose electrophoresis in TBE buffer. One plasmid with Eco RI fragments of approximately 3939 bp and 1012 bp and a Not I fragment of approximately 4931 bp was designated pMDT134 (FIG. 16). The DNA sequence of the cloned PCR fragment was confirmed by DNA sequencing.

Example 11

Construction of *Bacillus licheniformis* Bli1904II Restriction Endonuclease Gene Deletion Plasmid A temperature-sensitive plasmid was constructed to allow deletion of the Bli1904II restriction endonuclease gene in *Bacillus licheniformis*.

Figure 17:
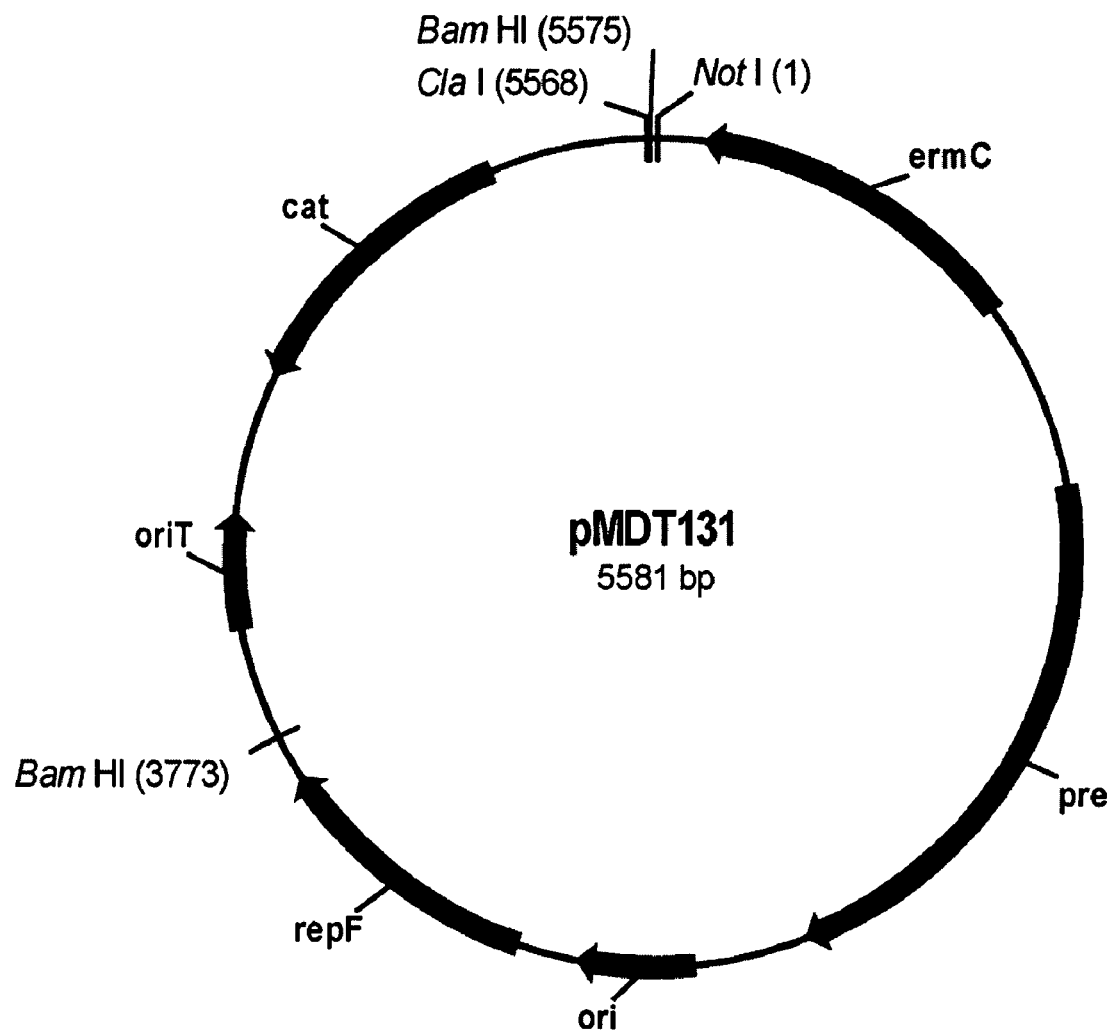
FIG. 17 shows a restriction map of pMDT131.

Plasmid pMDT131 was constructed to create a temperature-sensitive plasmid conferring chloramphenicol resistance. Plasmid pMRT074 (U.S. Published Application 2003/0175902) was digested with Eco RI and then treated with T4 DNA polymerase plus dNTPs to generate blunt ends, as described in Example 7. The plasmid was then digested with Not I, analyzed by 0.8% agarose electrophoresis in TBE buffer, and a vector fragment of approximately 4355 bp was purified using a QIAQUICK® Gel Extraction Kit. Plasmid pNBT1 was digested with Eco 47III and Not I, analyzed by 0.8% agarose electrophoresis in TBE buffer, and a fragment of approximately 1222 bp bearing the cat gene and a multiple cloning site was purified using a QIAQUICK® Gel Extraction Kit. The pMRT074 vector fragment was ligated with the pNBT1 cat fragment using T4 DNA ligase as described above, and *Bacillus subtilis* 168Δ4 was transformed with the ligation according to the procedure of Anagnostopoulos and Spizizen, 1961, supra, selecting for chloramphenicol resistance on TBAB chloramphenicol plates at 34° C. Plasmid DNA was isolated from one transformant using a QIAGEN® Plasmid Midi Kit and confirmed by digestion with Bam HI followed by 0.8% agarose electrophoresis in TBE buffer, which yielded expected fragments of approximately 3779 bp and 1802 bp. The resulting plasmid was designated pMDT131 (FIG. 17).

Figure 18:
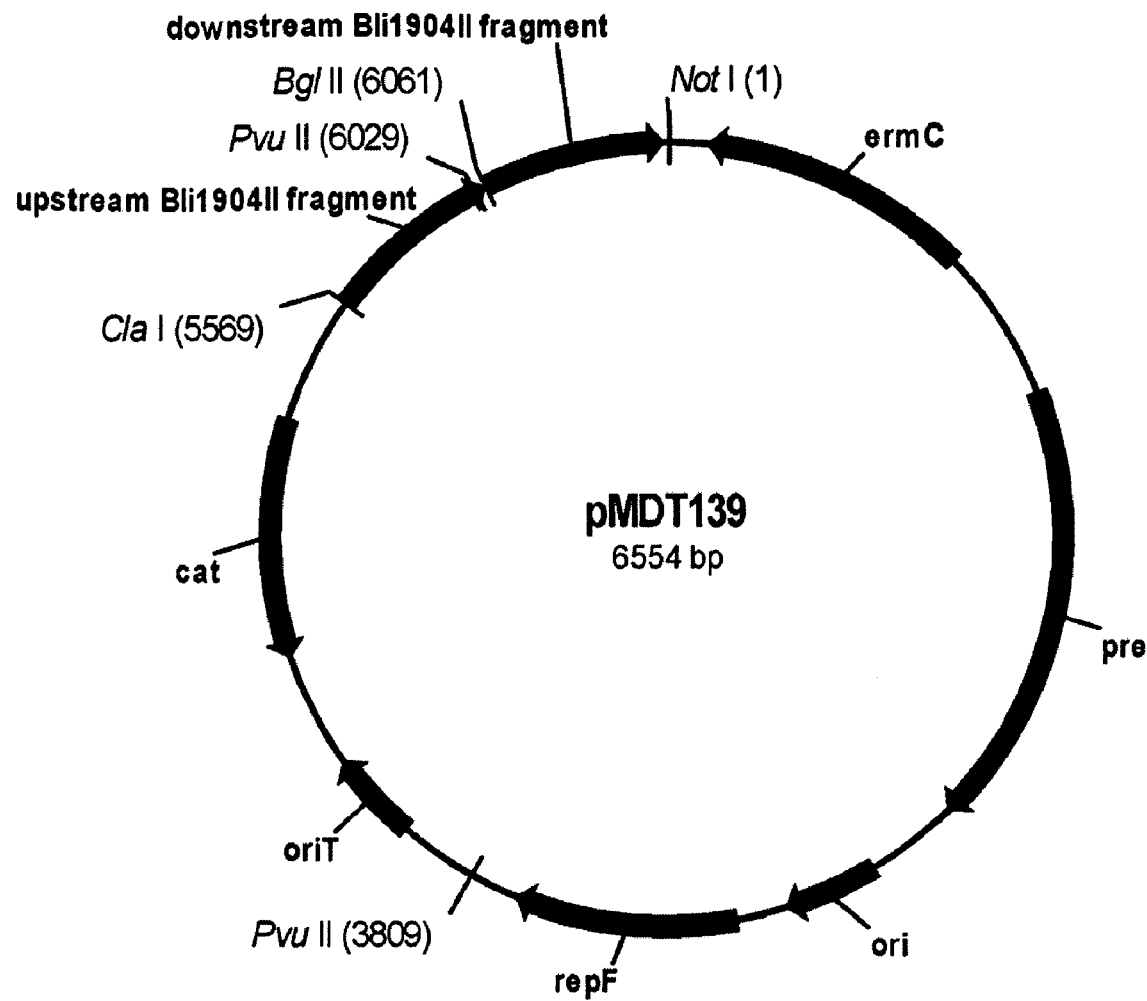
FIG. 18 shows a restriction map of pMDT139.

Plasmid pMDT139 was constructed to create a plasmid suitable for deletion of the Bli1904II gene from the chromosome of *Bacillus licheniformis*. *E. coli* SCS110 (Stratagene Corporation, La Jolla, Calif., USA), which is deficient for DNA methyltransferase Dam, was transformed with plasmid pMDT134 according to the manufacturer's instructions, selecting for ampicillin resistance on 2×YT ampicillin plates at 37° C. Plasmid DNA was isolated from one transformant using a QIAGEN® Plasmid Midi Kit, resulting in pMDT134 µlasmid DNA that can be digested with Cla I (which in some contexts is inhibited by Dam methylation). Plasmid pMDT134 DNA was digested with Cla I and Not I and analyzed by 0.8% agarose electrophoresis in TBE buffer, and a fragment of approximately 986 bp bearing the deleted Bli1904II gene was purified using a QIAQUICK® Gel Extraction Kit. Plasmid pMDT131 was digested with Cla I and Not I, analyzed by 0.8% agarose electrophoresis in TBE buffer, and a vector fragment of approximately 5569 bp was purified using a QIAQUICK® Gel Extraction Kit. The pMDT131 vector fragment was ligated with the deleted Bli1904II gene fragment using T4 DNA ligase as described above, and *Bacillus subtilis* 168Δ4 was transformed with the ligation according to the procedure of Anagnostopoulos and Spizizen, 1961, supra, selecting for chloramphenicol resistance on TBAB chloramphenicol plates at 34° C. Plasmid DNA was isolated from one transformant using a QIAGEN® Plasmid Midi Kit and confirmed by digestion with Pvu II, which yielded expected fragments of approximately 4334 bp and 2220 bp. The resulting plasmid was designated pMDT139 (FIG. 18).

Example 12

Deletion of the Bli1904II Gene in *Bacillus licheniformis* SJ1904

The *Bacillus licheniformis* Bli1904II restriction endonuclease gene was deleted from the chromosome of *Bacillus licheniformis* SJ1904 in order to test the effect on introduction of DNA into *Bacillus licheniformis*.

The Bli1904II gene was deleted from the chromosome of *Bacillus licheniformis* SJ1904 as follows. *Bacillus lichenifor-*

*mis* SJ1904 was transformed with plasmid pMDT139 bp electroporation according to the procedure of Xue et al., 1999, supra, as described in Example 8. The transformants were incubated for 2.5-3 hours at 34° C. and 250 rpm and then selected for erythromycin resistance on TBAB erythromycin/ lincomycin plates at 34° C.

One such transformant was grown on TBAB plates with erythromycin selection at 50° C. in order to select for integration of pMDT139 into the chromosome at the Bli1904II locus. One such integrant was then grown in VY medium without selection at 34° C. in order to permit excision and loss of the integrated plasmid. The culture was plated on LB plates at 37° C., and colonies were tested for sensitivity to erythromycin, indicating loss of the plasmid. Several erythromycin-sensitive clones were tested by PCR with primers 999592 and 999595 (shown above) using an EXTRACT-N-AMP™ Plant PCR Kit (Sigma-Aldrich, St. Louis, Mo., USA), as follows. *Bacillus licheniformis* cells were lysed by suspending a colony in 50 μl of Extraction Solution from the kit and incubating at 95° C. for 10 minutes. Each lysed suspension was then mixed with 50 μl of Dilution Solution from the kit, and 4 μl of each was used in a PCR according to manufacturer's instructions. One clone in which the PCR amplified a fragment of approximately 994 bp, indicating deletion of the Bli1904II gene from the chromosome, was designated *Bacillus licheniformis* MDT269.

Example 13

Transformation of *Bacillus licheniformis* Strains SJ1904 and MDT269

Transformation experiments were performed in order to determine the effects of Bli1904II restriction endonuclease and methyltransferase M.Bli1904II on introduction of DNA into *Bacillus licheniformis*.

Plasmid pCJ791 was isolated from transformants of *Bacillus subtilis* 168Δ4, *Bacillus subtilis* MDT101, and *Bacillus licheniformis* SJ1904 as described in Example 8. Electrocompetent cells of *Bacillus licheniformis* strains SJ1904 and MDT269 were prepared as described in Example 8. Both *Bacillus licheniformis* strains were transformed with pCJ791 plasmid DNA isolated from the three *Bacillus* sources. For each transformation, 60 μl of electrocompetent cells were transformed with 200 ng of plasmid DNA in an electroporation cuvette with a 1-mm electrode gap, using a GENE PULSER® set to 25 μF, 200Ω, and 1.0 kV. Transformations were performed in triplicate.

The results of the transformations are shown in Table 1. A low transformation frequency was obtained when *Bacillus licheniformis* SJ1904 (with a wild-type Bli1904II restriction endonuclease gene) was transformed with plasmid DNA from *Bacillus subtilis* 168Δ4 (not expressing methyltransferase M.Bli1904II). However, high transformation efficiencies were obtained when *Bacillus licheniformis* SJ1904 was transformed with plasmid DNA that was methylated by methyltransferase M.Bli1904 II (from *Bacillus subtilis* MDT101 or *Bacillus licheniformis* SJ1904). Furthermore, high transformation efficiencies were obtained when *Bacillus licheniformis* MDT269 (with the Bli1904II restriction endonuclease gene deleted) was transformed with plasmid DNA from any of the three sources (whether methylated by methyltransferase M.Bli1904II or not). The results showed that transformation of *Bacillus licheniformis* by electroporation with plasmid DNA was significantly improved either by isolating the plasmid DNA from a host strain expressing M.Bli1904II DNA methyltransferase, which modifies the plasmid DNA, or by deleting the Bli1904II restriction endonuclease gene in the recipient *Bacillus licheniformis* strain.

TABLE 1

Transformation of *Bacillus licheniformis* SJ1904 and MDT269 with pCJ791 plasmid DNA isolated from *Bacillus subtilis* 168Δ4, *Bacillus subtilis* MDT101, and *Bacillus licheniformis* SJ1904.

| *Bacillus licheniformis* strain | Source of pCJ791 DNA | Transformants per μg DNA[1] |
|---|---|---|
| B. licheniformis SJ1904 (wild-type Bli1904II gene) | Bacillus subtilis 168Δ4 (no methyltransferase M.Bli1904II gene) | 17 ± 15 |
| | Bacillus subtilis MDT101 (cloned methyltransferase M.Bli1904II gene) | $1.6 \times 10^4 \pm 8.3 \times 10^3$ |
| | Bacillus licheniformis SJ1904 (native methyltransferase M.Bli1904II gene) | $1.2 \times 10^4 \pm 5.7 \times 10^3$ |
| *B. licheniformis* MDT269 (deleted Bli1904II gene) | Bacillus subtilis 168Δ4 (no methyltransferase M.Bli1904II gene) | $6.4 \times 10^3 \pm 9.6 \times 10^2$ |
| | Bacillus subtilis MDT101 (cloned methyltransferase M.Bli1904II gene) | $7.2 \times 10^3 \pm 2.1 \times 10^3$ |
| | Bacillus licheniformis SJ1904 (native methyltransferase M.Bli1904II gene) | $4.1 \times 10^3 \pm 5.8 \times 10^2$ |

[1]Transformation frequency is the mean of three replicates ± standard deviation.

Example 14

Transformation of *Bacillus licheniformis* with Plasmid DNA Methylated in vitro

A cell-free extract (CFE) of *Bacillus licheniformis* SJ1904 was prepared according to the method of Alegre et al., 2004, *FEMS Microbiology Letters* 241: 73-77. Plasmid pCJ791 isolated from a transformant of *Bacillus subtilis* 168Δ4 was methylated by treatment with the CFE and S-adenosylmethionine (SAM), as described by Alegre et al., 2004, supra. In addition, a control was performed in which the CFE was replaced with the buffer used to prepare the CFE. After treatment, the DNA was extracted with phenol and chloroform, precipitated with isopropanol, and resuspended in 20 μl water. *Bacillus licheniformis* SJ1904 was then transformed by electroporation as described in Example 8, using 200 ng of pCJ791 plasmid DNA, either treated as described above or untreated. Transformations were performed in triplicate.

The results of the transformations are shown in Table 2. Transformation with plasmid DNA that had been treated with CFE plus SAM resulted in more than 100-fold higher transformation frequency than transformation with either untreated plasmid DNA or plasmid DNA treated with SAM alone. These results confirmed that methylation of plasmid DNA in vitro improved transformation of *Bacillus licheniformis*.

TABLE 2

Transformation of *Bacillus licheniformis* SJ1904
with pCJ791 plasmid DNA methylated in vitro.

| Treatment of plasmid DNA | Transformants per μg DNA[1] |
|---|---|
| *B. licheniformis* SJ1904 CFE + SAM | $6.9 \times 10^3 \pm 1.2 \times 10^3$ |
| CFE buffer + SAM | 30 ± 20 |
| untreated | 50 ± 20 |

Plasmid DNA was isolated from *Bacillus subtilis* 168Δ4.
[1]Transformation frequency is the mean of three replicates ± standard deviation.

Example 15

Effect of *Bacillus licheniformis* Restriction-modification System on Conjugal Plasmid Transfer in *Bacillus subtilis*

The effect of the *Bacillus licheniformis* restriction-modification system on conjugal plasmid transfer was tested using plasmid pCJ791, which may be transferred by conjugation from a suitable donor cell to a recipient cell, due to the presence of the oriT origin of transfer present on the plasmid. One such suitable conjugation donor strain is *Bacillus subtilis* PP289-5 (WO 96/029418), which has a deletion in the arl (dal) gene encoding D-alanine racemase and contains plasmids pBC16 (conferring tetracycline resistance) and pLS20, which confer the ability to mobilize oriT-containing plasmids.

*Bacillus subtilis* PP289-5 was transformed with genomic DNA isolated from *Bacillus subtilis* MDT101 according to the procedure of Anagnostopoulos and Spizizen, 1961, supra, selecting for chloramphenicol resistance on TY chloramphenicol plates at 37° C. One such transformant, containing the cat gene and the M.Bli1904II DNA methyltransferase expression cassette at the amyE locus, was designated *Bacillus subtilis* AEB711.

*Bacillus subtilis* strains PP289-5 and AEB711 were transformed with plasmid pCJ791 according to the procedure of Anagnostopoulos and Spizizen, 1961, supra, selecting for erythromycin resistance on TBAB erythromycin/lincomycin plates at 34° C. One PP289-5 transformant was designated *Bacillus subtilis* MDT104, and one AEB711 transformant was designated *Bacillus subtilis* MDT105.

*Bacillus subtilis* donor strains MDT104 and MDT105 were used to transfer plasmid pCJ791 to *Bacillus licheniformis* recipient strains SJ1904 and MDT269 bp conjugation. *Bacillus licheniformis* SJ1904 and MDT269 were grown overnight at 30° C. on LBPG plates. *Bacillus subtilis* MDT104 and MDT105 were grown overnight at 30° C. on LBPG plates containing 100 μg of D-alanine, 10 μg of tetracycline, and 5 μg of erythromycin per ml. Cells of each strain were then suspended in TY medium, and the optical density (OD) was measured at 450 nm. Based on OD, equal amounts of one donor strain and one recipient strain were mixed, using the equivalent of 100 μl of a cell suspension having an $OD_{450}$ of 50. Mixtures were spread on LB plates containing 100 μg of D-alanine per ml and incubated at 30° C. Under these conditions, both the donor and recipient strain were able to grow, and plasmid pCJ791 could be transferred by conjugation from donor to recipient. After incubation for 6 hours, cells were suspended in 1 ml of TY medium, aliquots were spread on TY plates containing 2 μg of erythromycin per ml, and the plates were incubated overnight at 30° C. Under these conditions, only *Bacillus licheniformis* transconjugants (recipient cells that had received plasmid pCJ791 by conjugal transfer) were able to grow. The absence of D-alanine prevented growth of the arl-negative donor, and the presence of erythromycin prevented growth of the original recipient.

The number of transconjugants resulting from each conjugation was compared for the four different combinations of donor and recipient strains. The results of the conjugations are shown in Table 3. A low conjugation frequency was obtained when *Bacillus subtilis* MDT104 (containing no M.Bli1904 II DNA methyltransferase) was used as donor with *Bacillus licheniformis* SJ1904 (with a wild-type Bli1904II restriction endonuclease gene) as recipient. However, high conjugation frequencies were obtained when *Bacillus subtilis* MDT105 (expressing M.Bli1904II DNA methyltransferase) was used as donor (regardless of recipient) or when *Bacillus licheniformis* MDT269 (with the Bli1904II restriction endonuclease gene deleted) was used as recipient (regardless of donor). The results showed that conjugation of *Bacillus licheniformis* was significantly improved either by using a donor strain expressing M.Bli1904 II DNA methyltransferase, which modifies the plasmid DNA, or by deleting the Bli1904II restriction endonuclease gene in the recipient *Bacillus licheniformis* strain.

TABLE 3

Conjugal transfer of plasmid pCJ791 to *Bacillus licheniformis* strains SJ1904 and MDT269 from Bacillus subtilis donor strains MDT104 and MDT105.

| Bacillus licheniformis recipient strain | Bacillus subtilis donor strain | | Transconjugants per experiment |
|---|---|---|---|
| B. licheniformis SJ1904 (wild-type Bli1904II restriction endonuclease gene) | *Bacillus subtilis* MDT104 (no M.Bli1904II DNA methyltransferase gene) | A:<br>B:<br>C: | 3300<br>1730<br>380 |
| | *Bacillus subtilis* MDT105 (cloned M.Bli1904II DNA methyltransferase gene) | A:<br>B:<br>C: | 500,000<br>970,000<br>153,000 |
| B. licheniformis MDT269 (deleted Bli1904II restriction endonuclease gene) | *Bacillus subtilis* MDT104 (no M.Bli1904II DNA methyltransferase gene) | A:<br>B:<br>C: | 516,000<br>1,170,000<br>152,000 |
| | *Bacillus subtilis* MDT105 (cloned M.Bli1904II DNA methyltransferase gene) | A:<br>B:<br>C: | 957,000<br>1,700,000<br>1,350,000 |

Number of transconjugants is listed for each of three independent experiments, A, B, and C.

Deposit of Biological Material

The following biological materials have been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
|---|---|---|
| E. coli MDT45 (pMDT138) | NRRL B-41967 | Sep. 7, 2006 |
| E. coli MDT46 (pMDT156) | NRRL B-41968 | Sep. 7, 2006 |

The strains have been deposited under conditions that assure that access to the cultures will be available during the pendency of this patent application to one determined by the Commissioner of Patents and Trademarks to be entitled thereto under 37 C.F.R. § 1.14 and 35 U.S.C. § 122. The deposits represent substantially pure cultures of the deposited strains. The deposits are available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. An isolated DNA methyltransferase selected from the group consisting of:
   (a) a DNA methyltransferase comprising an amino acid sequence having at least 95% sequence identity with amino acids 1 to 381 of SEQ ID NO: 2;
   (b) a DNA methyltransferase encoded by a polynucleotide that hybridizes under high stringency conditions with nucleotides 1 to 1143 of SEQ ID NO: 1 or its full-length complementary strand, said high stringency conditions are hybridization at 42° C. in 5×SSPE, 0.3% SDS, 200 µg/ml sheared and denatured salmon sperm DNA, and 50% formamide, and washed three times each for 15 minutes using 2×SSC, 0.2% SDS at 65° C.,
   wherein the DNA methyltransferase of (a) or (b) catalyzes the methylation of cytosine in the sequence GCNGC; and
   (c) a DNA methyltransferase comprising or consisting of amino acids 1 to 381 of SEQ ID NO: 2, or a fragment thereof having DNA methyltransferase activity.

2. The DNA methyltransferase of claim 1, which is encoded by the polynucleotide contained in plasmid pMDT138 which is contained in *E. coli* NRRL B-41967.

3. A method of producing bacterial transformants, comprising:
   (a) methylating in vitro a DNA with the DNA methyltransferase of claim 1 to produce a methylated DNA;
   (b) introducing the methylated DNA into a bacterial host cell, wherein the bacterial host cell comprises a restriction endonuclease able to degrade the DNA but unable to degrade the methylated DNA; and
   (c) isolating transformants of the bacterial host cell comprising the methylated DNA.

4. A method of producing a polypeptide having biological activity, comprising:
   (a) cultivating a bacterial host cell comprising an introduced DNA encoding or involved in the expression of the polypeptide having biological activity under conditions conducive for production of the polypeptide; wherein the DNA is methylated in vitro prior to being introduced into the bacterial host cell by a DNA methyltransferase of claim 1;
   wherein the methylation prevents the introduced DNA from being digested by a restriction endonuclease of the bacterial host cell; and
   (b) recovering the polypeptide having biological activity.

5. A method of producing a mutant of a parent bacterial cell, which comprises:
   (a) introducing into a parent bacterial cell a DNA comprising a nucleic acid construct to inactivate a gene encoding a polypeptide in the parent bacterial cell, which results in a mutant cell producing less of the polypeptide than the parent cell when cultivated under the same conditions; wherein the DNA is methylated in vitro prior to being introduced into the bacterial host cell by a DNA methyltransferase of claim 1;
   wherein the methylation prevents the introduced DNA from being digested by a restriction endonuclease of the parent bacterial cell; and
   (b) isolating the mutant cell.

6. The isolated DNA methyltransferase of claim 1, which comprises an amino acid sequence having at least 95% sequence identity with amino acids 1 to 381 of SEQ ID NO: 2.

7. The isolated DNA methyltransferase of claim 6, which comprises an amino acid sequence having at least 97% sequence identity with amino acids 1 to 381 of SEQ ID NO: 2.

8. The isolated DNA methyltransferase of claim 1, which is encoded by a polynucleotide that hybridizes under high stringency conditions with nucleotides 1 to 1143 of SEQ ID NO: 1 or its full-length complementary strand.

9. The isolated DNA methyltransferase of claim 8, which is encoded by a polynucleotide that hybridizes under very high stringency conditions with nucleotides 1 to 1143 of SEQ ID NO: 1 or its full-length complementary strand, wherein very high stringency conditions are hybridization at 42° C. in 5×SSPE, 0.3% SDS, 200 µg/ml sheared and denatured salmon sperm DNA, and 50% formamide, and washed three times each for 15 minutes using 2×SSC, 0.2% SDS at 70° C.

10. The isolated DNA methyltransferase of claim 1, which comprises amino acids 1 to 381 of SEQ ID NO: 2, or a fragment thereof having DNA methyltransferase activity.

11. The isolated DNA methyltransferase of claim 1, which consists of amino acids 1 to 381 of SEQ ID NO: 2, or a fragment thereof having DNA methyltransferase activity.

* * * * *